(12) United States Patent
Menard et al.

(10) Patent No.: US 12,168,805 B2
(45) Date of Patent: Dec. 17, 2024

(54) METHODS AND REAGENTS FOR DETECTING PIPERAQUINE-RESISTANT PLASMODIUM FALCIPARUM MALARIA

(71) Applicants: INSTITUT PASTEUR, Paris (FR); INSTITUT PASTEUR DU CAMBODGE, Phnom Penh (KH); CENTRE NATIONAL DE LA RECHERCHE SCIENTIFIQUE, Paris (FR)

(72) Inventors: Didier Menard, Le Gâvre (FR); Frédéric Ariey, Chevilly Larue (FR); Benoit Witkowski, Montauban (FR); Valentine Duru, Le Pre Saint Gervais (FR); Nimol Khim, Kandal (KH); Johann Beghain, Conflans Sainte-Honorine (FR); Benjamin Saint Pierre, Versailles (FR); Eric Legrand, Le Blanc-Mesnil (FR)

(73) Assignees: INSTITUT PASTEUR, Paris (FR); INSTITUT PASTEUR DU CAMBODGE, Phnom Penh (KH); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 571 days.

(21) Appl. No.: 16/324,140

(22) PCT Filed: Aug. 4, 2017

(86) PCT No.: PCT/IB2017/001125
§ 371 (c)(1),
(2) Date: Feb. 8, 2019

(87) PCT Pub. No.: WO2018/029532
PCT Pub. Date: Feb. 15, 2018

(65) Prior Publication Data
US 2019/0218623 A1 Jul. 18, 2019

Related U.S. Application Data

(60) Provisional application No. 62/373,179, filed on Aug. 10, 2016.

(51) Int. Cl.
*C12Q 1/68* (2018.01)
*C12Q 1/6827* (2018.01)
*C12Q 1/6893* (2018.01)

(52) U.S. Cl.
CPC ......... *C12Q 1/6893* (2013.01); *C12Q 1/6827* (2013.01); *C12Q 2600/156* (2013.01); *C12Q 2600/158* (2013.01); *G01N 2333/445* (2013.01); *Y02A 50/30* (2018.01)

(58) Field of Classification Search
CPC .............. C12Q 1/6893; C12Q 1/6827; C12Q 2600/156; C12Q 2600/158; C12Q 1/6851; C12Q 1/686; C12Q 1/6837; C12Q 1/6844; C12Q 2600/106; C12Q 1/68; G01N 2333/445; A61P 33/06; A61P 33/00

See application file for complete search history.

(56) References Cited

FOREIGN PATENT DOCUMENTS

WO 2015071759 A1 5/2015

OTHER PUBLICATIONS

Westling et al. Protein Science, vol. 8, No. 10, pp. 2001-2009 (Year: 1999).*
Ribacke et al. Molecular and Biochemical Parasitology. vol. 155, No. 1, Jul. 2007, pp. 33-44. (Year: 2007).*
Klemba. The Journal of Cell Biology, vol. 164, No1 1, p. 47-56 (Year: 2004).*
Christian Michael Parobek, Dissecting the Effects of Selective Pressures on the Genomes of Co-Endemic Plasmodium Vivax and Plasmodium Falciparum in Cambodia, Jul. 22, 2016, ProQuest Dissertations and Theses Professional, 1806138051, 1-140 (Year: 2016).*
Chaorattanakawee et al. Evidence of Plasmodium falciparum malaria multidrug resistance to artemisinin and piperaquine in Western Cambodia: dihydroartemisinin-piperaquine open-label multicenter clinical assessment, Antimicrobial Agents and Chemotherapy, vol. 59, pp. 4719-4726. (Year: 2015).*
Duru et al., Plasmodium falciparum dihydroartemisinin-piperaquine failures in Cambodia are associated with mutant K13 parasites presenting high survival rates in novel piperaquine in vitro assays: restrospective and prospective investigations, BMC Medicine, vol. 13:305, pp. 1-11. (Year: 2015).*
International Search Report and Written Opinion for PCT/IB2017/001125 dated Dec. 22, 2017 (17 pages).
Ribacke et al., "Genome wide gene amplifications and deletions in Plasmodium falciparum," Molecular & Biochemical Parisitology, 155:33-44 (2007).
Amato et al., "Genetic markers associated with dihydroartemisinin-piperaquine failure in Plasmodium falciparum malaria in Cambodia: a genotype-phenotype association study," The Lancet, 17:164-173 (2017).
Witkowski et al., A surrogate marker of piperaquine-resistant Plasmodium falciparum malaria: a phenotype-genotype association study, The Lancet, 17:174-173 (2017).

(Continued)

*Primary Examiner* — Dana H Shin
(74) *Attorney, Agent, or Firm* — Arrigo, Lee, Guttman & Mouta-Bellum LLP

(57) ABSTRACT

A method for genotyping a *Plasmodium* comprising: (a) providing a sample containing a *Plasmodium*; and (b) detecting the presence of an increased copy number of the genomic plasmepsin2-3 cluster. A method for the detection of a *Plasmodium* infection in a patient comprising: (a) providing a blood sample from a patient and (b) detecting the presence or absence of an increased copy number of the genomic plasmepsin2-3 cluster in the blood sample. Kits for genotyping a *Plasmodium* and/or detection of a *Plasmodium* infection. Methods of treating a *Plasmodium* infection.

17 Claims, 33 Drawing Sheets
Specification includes a Sequence Listing.

(56) References Cited

OTHER PUBLICATIONS

Imwong et al., "The spread of artemisinin-resistant Plasmodium falciparum in the Greater Mekong subregion: a molecular epidemiology observational study," The Lancent, 17:491-498 (2017).
Mukherjee et al., "Artemisinin resistance without pfkelch13 mutations in Plasmodium falciparum isolates from Cambodia," Malaria Journal, 16(195):1-12 (2017).
Westling et al., "Active site specificity of plasmepsin II," Protein Science, 8:2001-2009 (1999).
Klemba et al., "Trafficking of plasmepsin II to the food vacuole of the malaria parasite Plasmodium falciparum," The Journal of Cell Biology, 164(1):47-56 (2004).

* cited by examiner

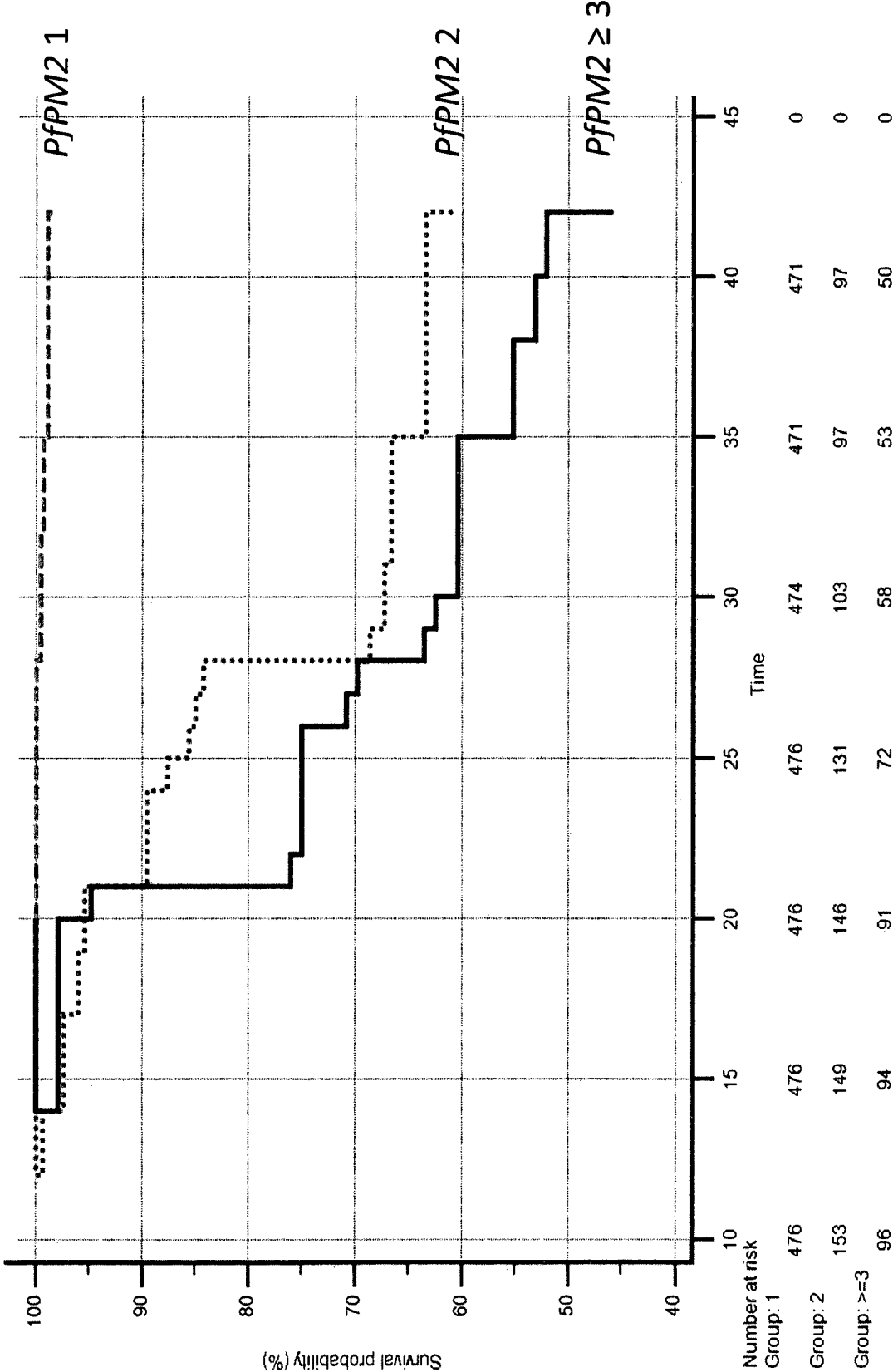

(Figure contents are a large data table that is rotated and too dense to transcribe reliably.)

| Parasite line ID | 307 | 6273 | 6337 | 6267 | 6403 | 6349 | 6237 | 6410 | 6369 | 6395 | 6341 | 6280 | 6246 | 6293 | 6391 | 6272 | 6218 | 6302 | 6229 | 6443 | 6430 | 6365 | 6429 | 6394 | 6219 | 6408 | 6224 | 6431 | 6320 | 6261 | 6411 | 6427 |
|---|---|---|---|---|---|---|---|---|---|---|---|---|---|---|---|---|---|---|---|---|---|---|---|---|---|---|---|---|---|---|---|---|
| in-vitro PSA survival rate (%) | | | | | | | | | | | | | | | | | | | | | | | | | | | | | | | | |
| | 0.1 | 0.2 | 0.4 | 0.5 | 0.6 | 0.8 | 6.0 | 6.4 | 19.2 | 25.8 | 28.9 | 36.9 | 39.3 | 39.4 | 40.0 | 40.8 | 42.5 | 46.6 | 49.6 | 51.3 | 51.8 | 51.8 | 56.7 | 58.6 | 58.7 | 61.4 | 61.5 | 62.1 | 70.5 | 71.6 | 77.4 |
| Mean Coverage (x) | | | | | | | | | | | | | | | | | | | | | | | | | | | | | | | | |
| Position on chromosome 4 | 272 | 232 | 214 | 132 | 325 | 242 | 203 | 198 | 131 | 203 | 237 | 121 | 143 | 132 | 179 | 169 | 127 | 88 | 125 | 117 | 109 | 167 | 146 | 152 | 150 | 31 | 209 | 109 | 67 | 250 | 104 | 172 |
| 908749 | T | T | T | W | T | T | W | W | W | W | W | T | W | W | W | W | W | W | W | T | W | W | W | W | W | W | W | T | W | W | T | W |
| 908755 | C | M | M | M | M | M | M | M | M | M | M | M | M | M | M | M | M | M | M | M | M | M | M | M | M | M | M | M | M | M | M | M |
| 908762 | T | W | W | W | W | W | W | W | W | W | W | W | W | W | W | W | W | W | W | W | W | W | W | W | W | W | W | W | W | W | W | W |
| 908772 | G | W | R | R | R | R | R | R | R | R | A | R | R | G | R | R | G | G | R | G | R | R | R | R | R | R | R | R | R | G | G | R |
| 908773 | T | T | T | T | W | T | T | T | T | T | T | T | T | T | T | T | T | T | T | T | W | T | T | T | T | T | T | T | T | T | G | T |
| 908774 | T | T | T | T | T | T | T | T | T | T | T | T | T | T | W | T | W | T | T | T | T | T | T | T | T | T | T | T | T | T | T | T |
| 908776 | T | T | T | W | T | T | T | T | T | T | T | T | T | T | T | T | T | T | T | T | T | T | T | T | T | T | T | T | T | T | T | T |
| 908778 | G | G | R | G | G | G | G | G | G | G | G | G | G | G | G | G | G | G | G | G | G | G | G | G | G | G | G | G | G | G | G | G |
| 908780 | G | R | R | R | R | R | R | R | R | R | R | R | R | R | R | R | R | R | R | R | R | R | R | R | R | R | R | R | R | R | R | R |
| 908785 | T | W | W | W | W | W | T | W | W | W | W | W | W | W | W | W | W | W | W | W | W | W | W | W | W | W | W | W | W | W | W | W |
| 908786 | A | W | W | W | W | W | W | A | A | A | A | A | A | A | A | A | A | A | A | A | A | A | A | A | A | A | A | A | A | A | A | A |
| 908792 | T | T | W | W | W | W | T | W | W | T | T | W | T | T | W | T | W | T | T | T | T | T | T | T | T | T | T | W | T | T | T | T |
| 908793 | T | W | W | W | W | W | W | W | W | W | T | T | T | T | T | T | T | T | T | T | T | T | T | T | T | T | T | T | T | T | T | T |
| 908794 | A | A | A | A | A | A | A | A | A | A | A | A | A | A | A | A | A | A | A | A | A | A | A | A | A | A | A | A | A | A | A | A |
| 908796 | T | H | Y | M | H | M | Y | Y | Y | T | T | T | T | T | T | T | T | T | T | T | T | T | T | T | T | T | T | T | T | T | T | T |
| 908797 | T | W | W | W | W | T | W | W | W | W | W | W | W | W | W | W | W | W | W | W | W | W | W | W | W | W | W | W | W | W | W | W |
| 908799 | T | W | W | W | W | T | W | W | W | W | W | W | W | W | W | W | W | W | W | W | W | W | W | W | W | W | W | W | W | W | T | W |

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: Plasmodium falciparum

<400> SEQUENCE: 1
tggtgatgca gaagttggag                                              20

<210> SEQ ID NO 2
<211> LENGTH: 21
<212> TYPE: DNA
<213> ORGANISM: Artificial Sequence
<220> FEATURE:
<223> OTHER INFORMATION: Plasmodium falciparum

<400> SEQUENCE: 2
tgggacccat aaattagcag a                                            21

<210> SEQ ID NO 3
<211> LENGTH: 23
<212> TYPE: DNA
```

```
<213> ORGANISM: Artificial Sequence
<220> FEATURE:
<223> OTHER INFORMATION: Plasmodium falciparum

<400> SEQUENCE: 3
ggattcgaac caacttatac tgc                                              23

<210> SEQ ID NO 4
<211> LENGTH: 27
<212> TYPE: DNA
<213> ORGANISM: Artificial Sequence
<220> FEATURE:
<223> OTHER INFORMATION: Plasmodium falciparum

<400> SEQUENCE: 4
aattggatct actgaaccta ttgataa                                          27

<210> SEQ ID NO 5
<211> LENGTH: 33
<212> TYPE: DNA
<213> ORGANISM: Artificial Sequence
<220> FEATURE:
<223> OTHER INFORMATION: Plasmodium falciparum

<400> SEQUENCE: 5
caacatttga tggtatcctt ggtttaggat gga                                   33

<210> SEQ ID NO 6
<211> LENGTH: 33
<212> TYPE: DNA
<213> ORGANISM: Artificial Sequence
<220> FEATURE:
<223> OTHER INFORMATION: Plasmodium falciparum

<400> SEQUENCE: 6
caacatttga tggtatcctt ggtttaggat gga                                   33

<210> SEQ ID NO 7
<211> LENGTH: 19
<212> TYPE: DNA
<213> ORGANISM: Artificial Sequence
<220> FEATURE:
<223> OTHER INFORMATION: Plasmodium falciparum

<400> SEQUENCE: 7
tgatgtgcgc aagtgatcc                                                   19

<210> SEQ ID NO 8
<211> LENGTH: 22
<212> TYPE: DNA
<213> ORGANISM: Artificial Sequence
<220> FEATURE:
<223> OTHER INFORMATION: Plasmodium falciparum

<400> SEQUENCE: 8
tcctttgtgg acattcttcc tc                                               22

<210> SEQ ID NO 9
<211> LENGTH: 25
<212> TYPE: DNA
<213> ORGANISM: Artificial Sequence
<220> FEATURE:
<223> OTHER INFORMATION: Plasmodium falciparum

<400> SEQUENCE: 9
tgcatctata aaacgatcag acaaa                                            25
```

-continued

```
<210> SEQ ID NO 10
<211> LENGTH: 21
<212> TYPE: DNA
<213> ORGANISM: Artificial Sequence
<220> FEATURE:
<223> OTHER INFORMATION: Plasmodium falciparum

<400> SEQUENCE: 10
tcgtgtgttc catgtgactg t                                              21

<210> SEQ ID NO 11
<211> LENGTH: 19
<212> TYPE: DNA
<213> ORGANISM: Artificial Sequence
<220> FEATURE:
<223> OTHER INFORMATION: Plasmodium falciparum

<400> SEQUENCE: 11
tgatgtgcgc aagtgatcc                                                 19

<210> SEQ ID NO 12
<211> LENGTH: 22
<212> TYPE: DNA
<213> ORGANISM: Artificial Sequence
<220> FEATURE:
<223> OTHER INFORMATION: Plasmodium falciparum

<400> SEQUENCE: 12
tcctttgtgg acattcttcc tc                                             22

<210> SEQ ID NO 13
<211> LENGTH: 192
<212> TYPE: DNA
<213> ORGANISM: Artificial Sequence
<220> FEATURE:
<223> OTHER INFORMATION: Plasmodium falciparum

<400> SEQUENCE: 13
aggtagttca aatgataata tcgaattagt agatttccaa aatataatgt tttatggtga    60
tgcagaagtt ggagataacc aacaaccatt tacatttatt cttgatacag gatctgctaa   120
tttatgggtc ccaagtgtta aatgtacaac tgcaggatgt ttaactaaac atctatatga   180
ttcatctaaa tc                                                       192

<210> SEQ ID NO 14
<211> LENGTH: 208
<212> TYPE: DNA
<213> ORGANISM: Artificial Sequence
<220> FEATURE:
<223> OTHER INFORMATION: Plasmodium falciparum

<400> SEQUENCE: 14
tcaacaatac agagccttaa ctgtgccgga gttaacacaa caaatgttcg acgcaaaaaa    60
tatgatgtgc gcaagtgatc caagacatgg aagatattta acggcatgtg ctatgtttag   120
aggaagaatg tccacaaagg aagttgacga acaaatgtta aacgttcaaa ataaaaactc   180
atcttatttt gtcgaatgga ttcctcac                                      208

<210> SEQ ID NO 15
<211> LENGTH: 203
<212> TYPE: DNA
<213> ORGANISM: Artificial Sequence
<220> FEATURE:
```

<223> OTHER INFORMATION: Plasmodium falciparum

<400> SEQUENCE: 15
ctattgtaga tattaaagat aaagctgaca aaactattat tactattgcc cacagaattg    60
catctataaa acgatcagac aaaattgtgg tatttaataa ccctgatcga aatggaacct   120
ttgtacagtc acatggaaca cacgatgaat tattatcagc acaagatgga atatataaaa   180
aatatgtaaa attagctaaa tga                                          203

<210> SEQ ID NO 16
<211> LENGTH: 20
<212> TYPE: DNA
<213> ORGANISM: Artificial Sequence
<220> FEATURE:
<223> OTHER INFORMATION: Plasmodium falciparum

<400> SEQUENCE: 16
tggaacaatg gtagctgcac                                               20

<210> SEQ ID NO 17
<211> LENGTH: 20
<212> TYPE: DNA
<213> ORGANISM: Artificial Sequence
<220> FEATURE:
<223> OTHER INFORMATION: Plasmodium falciparum

<400> SEQUENCE: 17
ggcgcaattt ttcaggaact                                               20

<210> SEQ ID NO 18
<211> LENGTH: 32
<212> TYPE: DNA
<213> ORGANISM: Artificial Sequence
<220> FEATURE:
<223> OTHER INFORMATION: Plasmodium falciparum

<400> SEQUENCE: 18
tgtcttcttg aaaattatca aaacggcgaa gg                                 32

<210> SEQ ID NO 19
<211> LENGTH: 30
<212> TYPE: DNA
<213> ORGANISM: Artificial Sequence
<220> FEATURE:
<223> OTHER INFORMATION: Plasmodium falciparum

<400> SEQUENCE: 19
tgaatcagct gtgaatagct ctacatttaa                                    30

<210> SEQ ID NO 20
<211> LENGTH: 30
<212> TYPE: DNA
<213> ORGANISM: Artificial Sequence
<220> FEATURE:
<223> OTHER INFORMATION: Plasmodium falciparum

<400> SEQUENCE: 20
caattcaaca tttgatggat taaacattga                                    30

<210> SEQ ID NO 21
<211> LENGTH: 30
<212> TYPE: DNA
<213> ORGANISM: Artificial Sequence
<220> FEATURE:
<223> OTHER INFORMATION: Plasmodium falciparum

```
<400> SEQUENCE: 21
tgaagaatcc tttaacacgt ttcgagtaac                                   30

<210> SEQ ID NO 22
<211> LENGTH: 30
<212> TYPE: DNA
<213> ORGANISM: Artificial Sequence
<220> FEATURE:
<223> OTHER INFORMATION: Plasmodium falciparum

<400> SEQUENCE: 22
tgcttcagca tttgatcgat tgaaattagg                                   30
```

METHODS AND REAGENTS FOR DETECTING PIPERAQUINE-RESISTANT PLASMODIUM FALCIPARUM MALARIA

INTRODUCTION

Antimalarial efficacy of artemisinin-based combination therapies (ACTs), the first-line treatment for uncomplicated *Plasmodium falciparum* malaria, relies on both fast-acting artemisinin (ART) derivatives and long-lasting partner drugs. Resistance to ARTS, which is now fixed in western Cambodia and observed across Southeast Asia, increases the proportion of parasites surviving a 3-day course of an ACT. Resistance to the partner drug is a greater risk when more parasites survive ARTs. The reduced efficacy of ARTs and partner drugs translates into late treatment failures and prolonged parasite carriage, thereby increasing the transmission potential of drug-resistant infections.

In Cambodia, the artesunate-mefloquine ACT was chosen as the first-line drug in 2001. By 2008, the high frequency of treatment failures in western provinces, the epicentre of *P. falciparum* multidrug resistance, led to its replacement by dihydroartemisinin-piperaquine (DHA-PPQ) in 2008, and later throughout Cambodia in 2010. In recent years the spread of ART-resistant *P. falciparum*, from western Cambodia to neighboring provinces,[1-5] has been followed by a spectacular increase in DHA-PPQ failure rates. Failures are currently estimated to reach 60%,[6-10] indicating a dramatic expansion of piperaquine (PPQ) resistance. Until now, the detection of PPQ resistance has been based on logistically demanding 42-day follow up studies of DHA-PPQ treated patients.[11] The recently developed in-vitro Piperaquine Survival Assay (PSA)[7] has been shown with in-vitro culture-adapted parasites and freshly collected ex-vivo patient isolates to detect PPQ-resistance and treatment failure more reliably than classic dose-response assays.[7] The in-vitro PSA therefore provides a reliable tool to identify molecular signatures associated with resistance.

Here, the inventors used in-vitro PSA-based phenotypic information to compare whole-genome sequences of Cambodian *P. falciparum* lines dichotomized as PPQ-susceptible or -resistant based on their in-vitro PSA results.[7] The exomes of culture-adapted ART-resistant parasite lines (all harboring the K13-C580Y mutation) were compared for single nucleotide polymorphisms (SNPs) and copy number variations (CNVs). The inventors observed a highly significant association between an increased copy number of Pfplasmepsin2 (PF3D7_1408000) and Pfplasmepsin3 PF3D7_1408100) (encoded in tandem on chromosome 14) and in-vitro PPQ resistance. Increased Pfplasmepsin2 (PfPM2) gene copy number was then assessed as a candidate resistance marker in 134 isolates with known ex-vivo PSA survival rates and in 725 blood samples collected during the years 2009-2015 from Cambodian patients treated with DHA-PPQ and followed up for 42 days. These data provide compelling evidence that amplification of the PfPM2 locus is a molecular marker of PPQ resistance, which can be used to predict the risk of DHA-PPQ treatment failure in ART-resistant areas. The inventors also provide novel insights into the possible role of the digestive vacuole in PPQ resistance and the stepwise selection process that has resulted in multidrug resistance in Cambodian *P. falciparum* parasites.

SUMMARY

Methods for genotyping a *Plasmodium* are provided. In some embodiments the methods comprise (a) providing a sample containing a *Plasmodium*; and (b) detecting the presence of an increased copy number of the genomic plasmepsin2-3 cluster. In variant methods of the invention, said methods comprise in a sample containing a *Plasmodium*, detecting the presence of an increased copy number of the genomic plasmepsin2-3 cluster. In some embodiments the sample is a biological sample previously obtained from a patient. In some embodiments the *Plasmodium* is *Plasmodium falciparum*. In some embodiments the presence of increased copy number of the genomic plasmepsin2-3 cluster in the sample is detected by sequencing. In some embodiments the presence of increased copy number of the genomic plasmepsin2-3 cluster in the sample is detected by PCR. In a preferred embodiment the PCR is quantitative PCR (qPCR). In some embodiments the method comprises determining the copy number of at least one of the Pfplasmepsin2 (PF3D7_1408000) gene (PfPM2) and the Pfplasmepsin3 (PF3D7_1408100) gene (PfPM3). In some embodiments the method comprises determining the level of at least one mRNA selected from a PfPM2 mRNA and a PfPM3 mRNA. In some embodiments the method comprises determining the level of at least one protein selected from a PfPM2 protein and a PfPM3 protein. In some embodiments 2, 3, or 4 copies of the genomic plasmepsin2-3 cluster are detected. In some embodiments the methods further comprise detecting the presence of a mutated K-13 propeller nucleic acid or protein in the sample. In some embodiments the methods further comprise detecting the presence of no more than a single copy of a Pfmdr1 nucleic acid in the sample.

Methods for detecting a *Plasmodium* infection in a patient are also provided. In some embodiment the methods comprise: (a) providing a blood sample from a patient and (b) detecting the presence or absence of an increased copy number of the genomic plasmepsin2-3 cluster in the blood sample. In another embodiment the methods comprise: on a blood sample previously obtained from a patient, in vitro detecting the presence or absence of an increased copy number of the genomic plasmepsin2-3 cluster. In some embodiments the *Plasmodium* is *Plasmodium falciparum*. In some embodiments the presence or absence of increased copy number of the genomic plasmepsin2-3 cluster in the sample is detected by sequencing. In some embodiments the presence or absence of an increased copy number of the genomic plasmepsin2-3 cluster in the sample is detected by PCR. In some embodiments the presence of increased copy number of the genomic plasmepsin2-3 cluster in the sample is detected by quantitative PCR (qPCR). In some embodiments the method comprises determining the copy number of at least one of the Pfplasmepsin2 (PF3D7_1408000) gene (PfPM2) and the Pfplasmepsin3 (PF3D7_1408100) gene (PfPM3). In some embodiments the method comprises determining the level of at least one mRNA selected from a PfPM2 mRNA and a PfPM3 mRNA. In some embodiments the method comprises determining the level of at least one protein selected from a PfPM2 protein and a PfPM3 protein. In some embodiments 2, 3, or 4 copies of the genomic plasmepsin2-3 cluster are detected. In some embodiments the methods further comprise detecting the presence or absence of a mutated K-13 propeller nucleic acid or protein in the sample. In some embodiments the methods further comprise detecting the presence or absence of no more than a single copy of a Pfmdr1 nucleic acid in the sample. In some embodiments the presence of an increased copy number of the genomic plasmepsin2-3 cluster indicates that the *Plasmodium* is resistant to piperaquine. In some embodiments the presence of a mutated K13 propeller nucleic acid or protein indicates that the *Plasmodium* is also resistant to artemisinin derivatives. In some embodiments the methods further comprise administering to said patient infected with a *Plasmodium* resistant to piperaquine a treatment based on artemisinin derivatives for longer than the routine protocol, and/or another anti-malarial drug.

Kits for detecting a *Plasmodium* infection are also provided. In some embodiments the kits comprise primers for the amplification of a plasmepsin2-3 cluster nucleic acid and reagents for the detection of the amplified product. In some embodiments the kit contains a probe for detecting a plasmepsin2-3 cluster nucleic acid. In some embodiments the probe is labeled with a fluorescent, radioactive or enzymatic label. In some embodiments the kit detects a PfPM2 nucleic acid. In some embodiments the kit detects a PfPM3 nucleic acid. In some embodiments the kit comprises at least one of the following primers: 5'-TGGTGATGCAGAAGTTG-GAG-3' ID (SEQ NO.1); 5'-TGGGACCCATAAATT-AGCAGA-3' (SEQ ID NO.2); 5'-GGATTCGAACCAACT-TATACTGC-3' (SEQ ID NO.3); and 5'-AATTGGATCTACTGAACCTATTGATAA-3' (SEQ ID NO.4). In some embodiments the kit comprises at least one probe comprising the sequence 5'-CAACATTT-GATGGTATCCTTGGTTTAGGATGGA-3' (SEQ ID NO.5). In some embodiments the kit comprises the following probe: 5'-FAM-CAACATTTGATGGTATCCTTGGTT-TAGGATGGA-BHQ1-3' (SEQ ID NO.6). In some embodiments the kit further comprises primers for the amplification of a K-13 propeller nucleic acid and reagents for the detection of the amplified product. In some embodiments the kit further comprises primers for the amplification of a Pfmdr1 nucleic acid and reagents for the detection of the amplified product.

BRIEF DESCRIPTION OF THE DRAWINGS

FIGS. 4A and 4B show cumulative proportion of non-recrudescent patients treated with a 3-day course of DHA-PPQ according to (A) PfPM2 gene copy number (Logrank test: overall p<0.0001; p<0.0001 for single copy vs. 2 copies; p<0.0001 for single copy vs. ≥3 copies; p=0.017 for 2 copies vs. ≥3 copies) and (B) PfPM2 gene copy number and K13 genotype (Logrank test: overall p<0.0001; p<0.0001 for K13 wild-type/PfPM2 single copy vs. K13 wild-type/PfPM2 multi-copy; p=0.002 for K13 wild-type/PfPM2 single copy vs. K13 mutant/PfPM2 single copy; p<0.0001 for K13 wild-type/PfPM2 single copy vs. K13 mutant/PfPM2 multi-copy; p=0.001 (HR=6.9 [95% CI: 0.5-96.6]), for K13 wild-type/PfPM2 multicopy vs. K13 mutant/PfPM2 single copy; p=0.07 (HR=2.6 [95% CI: 1.3-5.5]), for K13 wild-type/PfPM2 multicopy vs. K13 mutant/PfPM2 multi-copy; p<0.0001 (HR=17.5 [95% CI: 12.2-25.2]), for K13 mutant/PfPM2 single copy vs. K13 mutant/PfPM2 multi-copy) detected in isolates collected at the time of enrollment, prior to treatment. In graph: K13 wild-type/PfPM2 single copy: $1^{st}$ line from the top, K13 wild-type/PfPM2 multicopy: $3^{rd}$ line from the top, K13 mutant/PfPM2 single copy: $2^{nd}$ line from the top, and K13 mutant/PfPM2 multicopy: 4th line from the top.

Figure 8B.1:
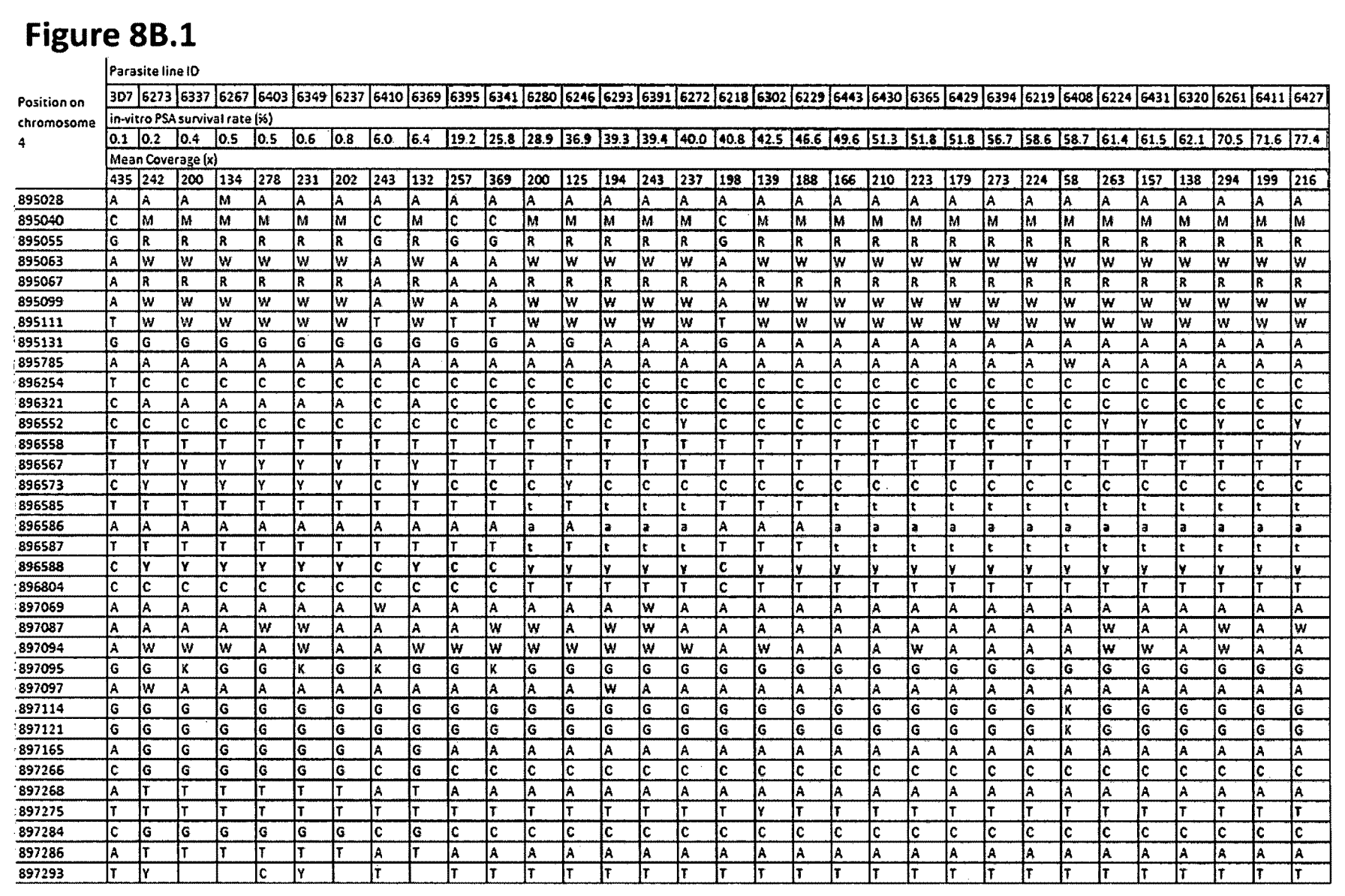
Figure 8B.2:
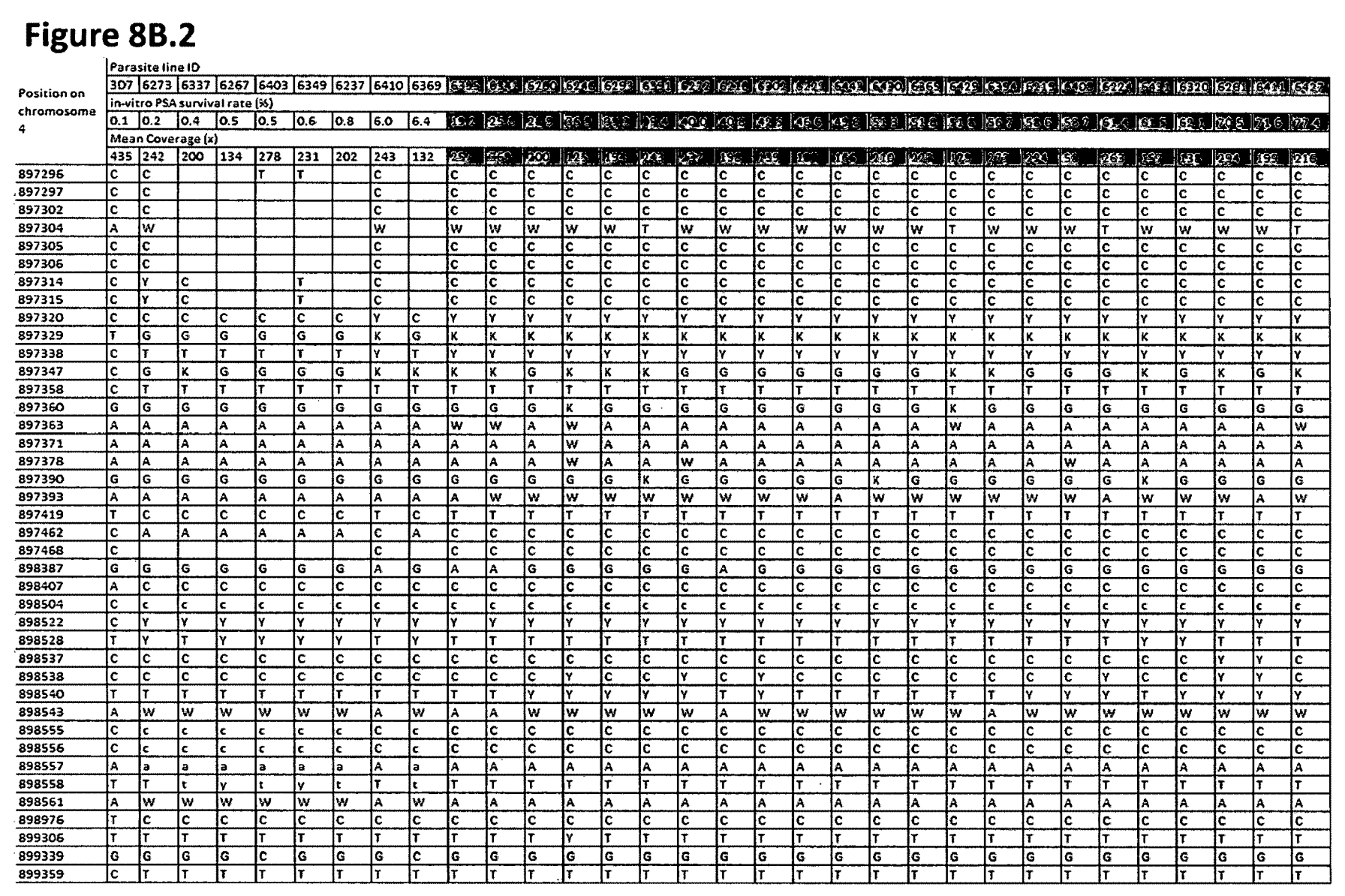
Figure 8B.4:
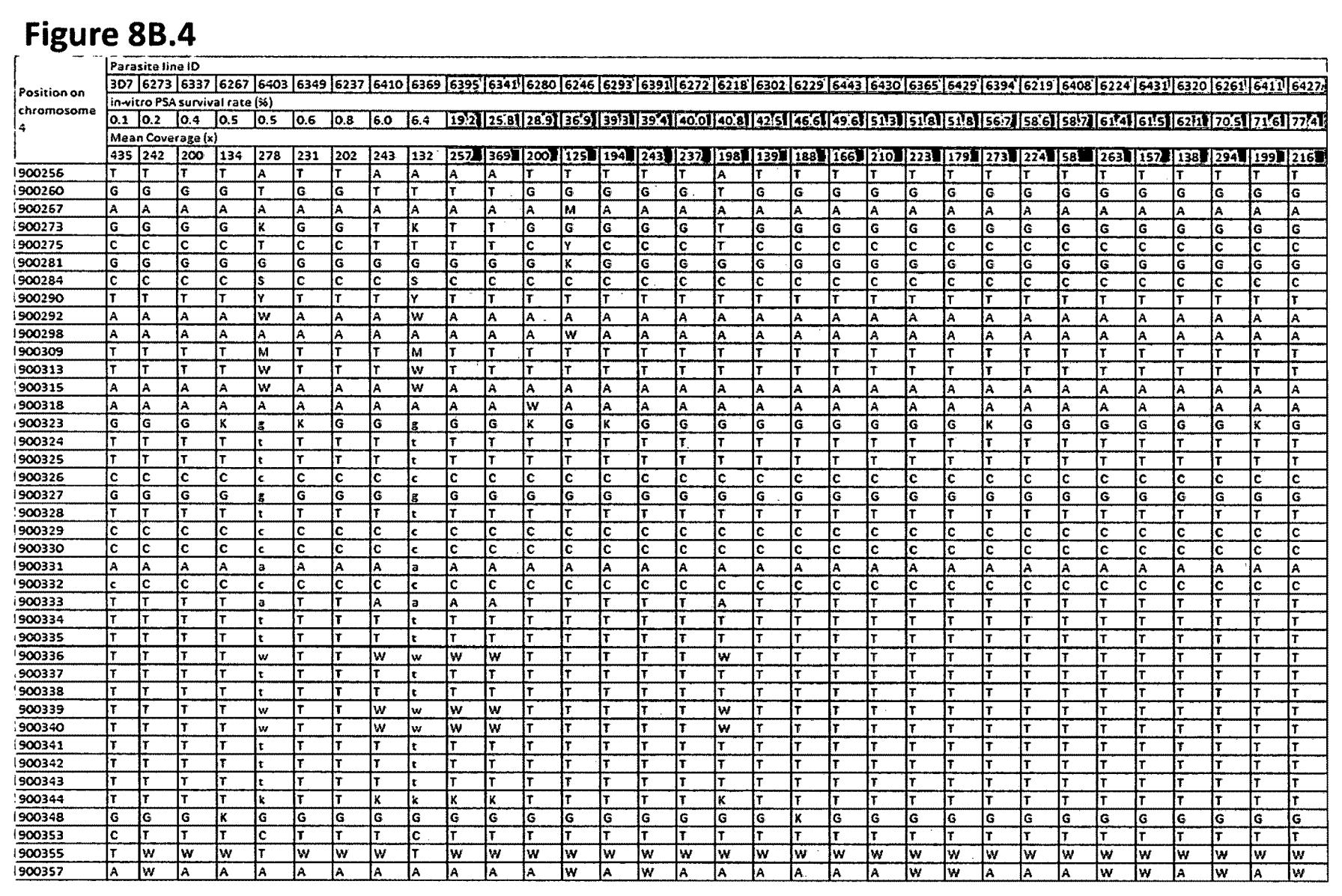
Figure 8B.5:
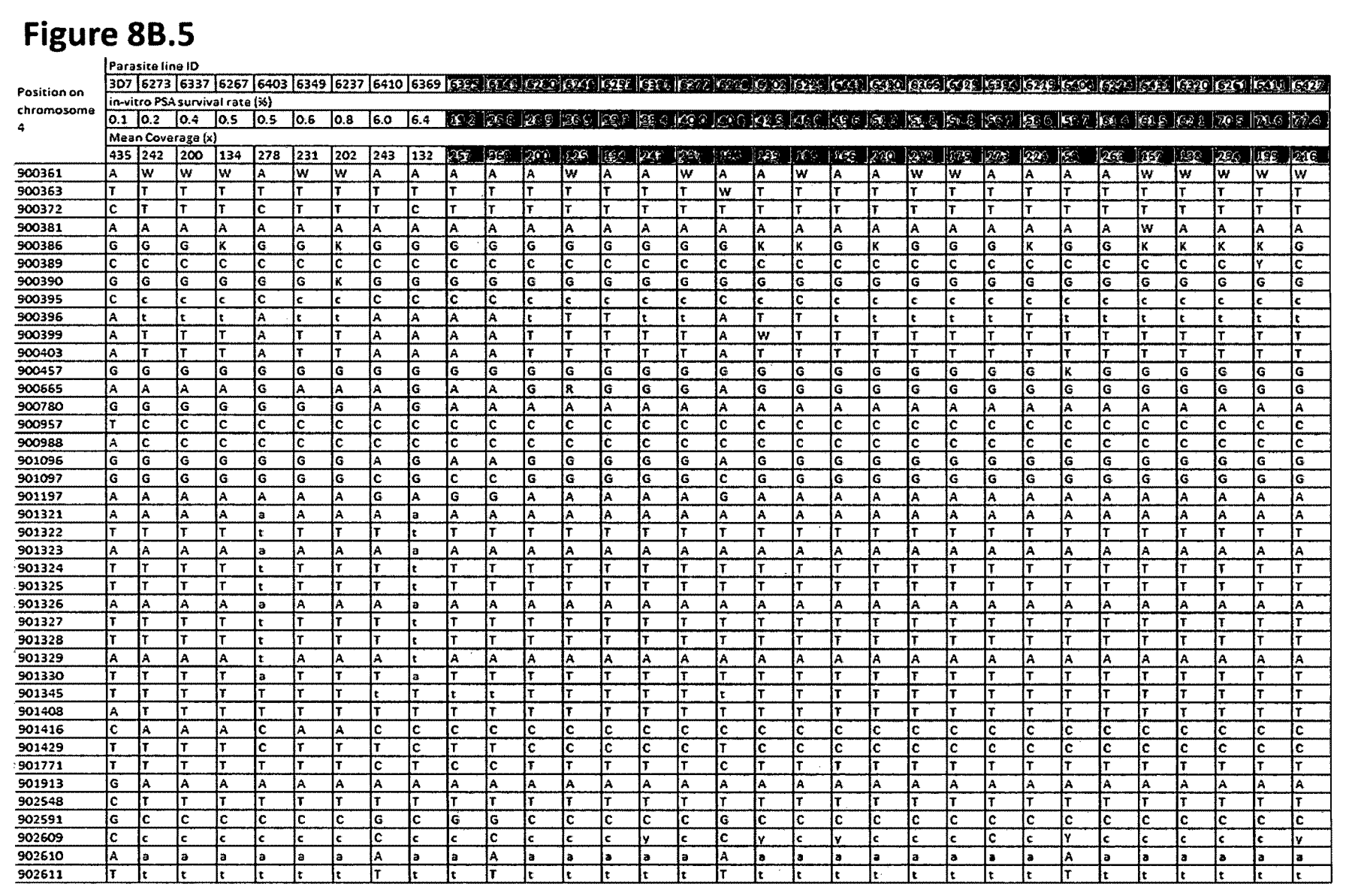
Figure 8B.6:
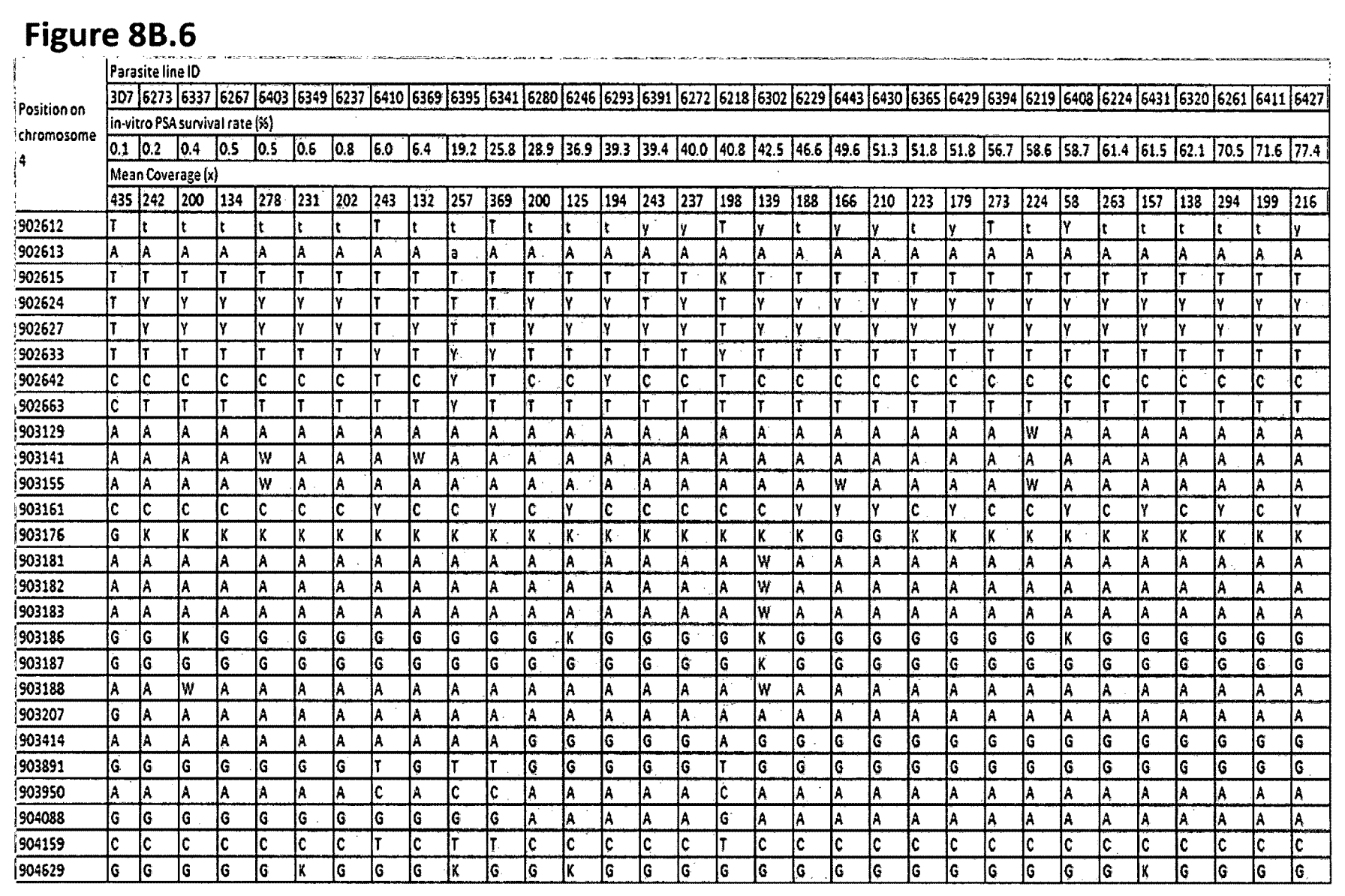
Figure 8C.1:
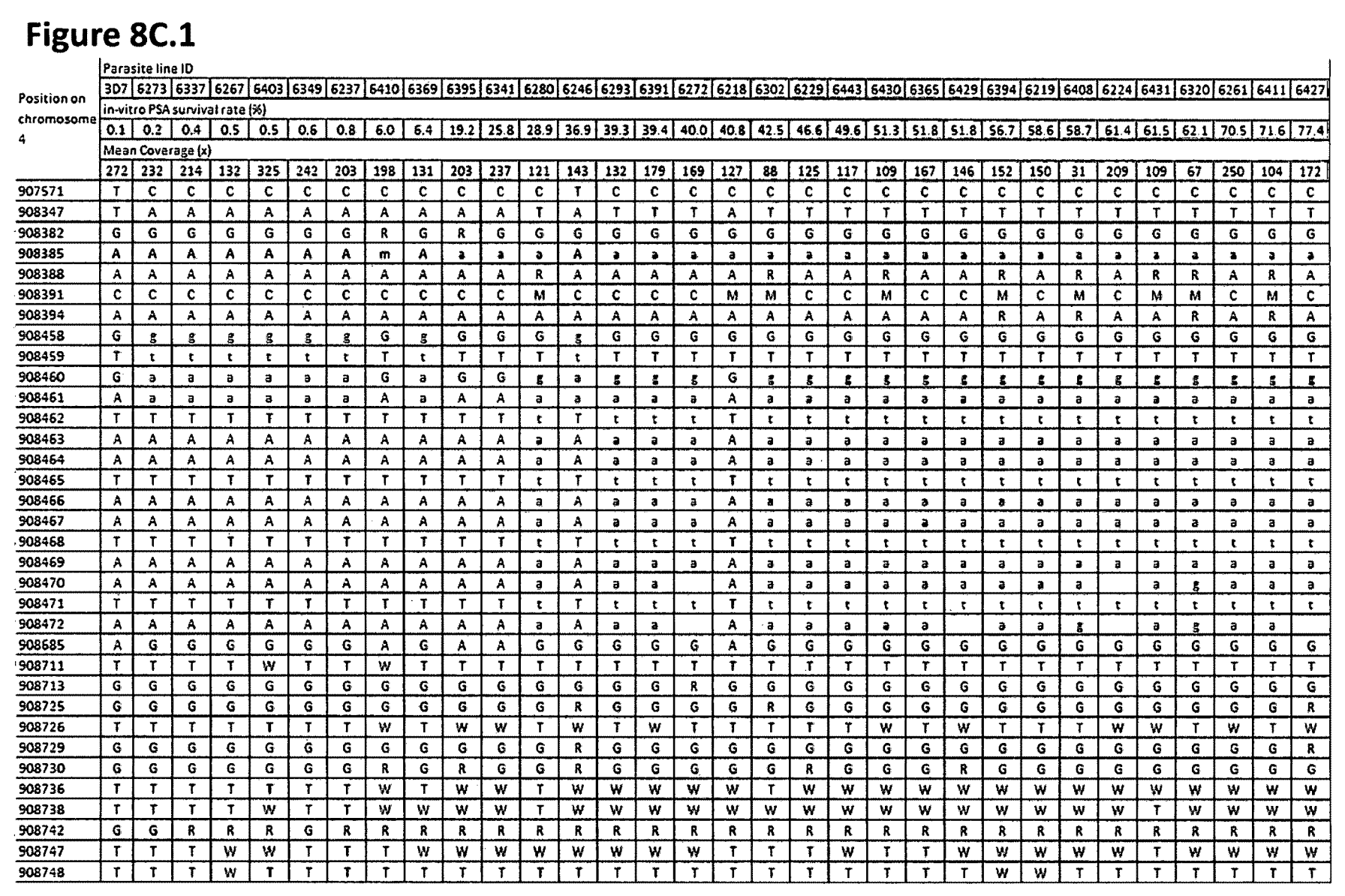

FIGS. 8B.1 to 8B.6, and 8C.1 to 8C.2 show a list of the positions with variable proportions of wild type and mutant nucleotides of PF3D7_0420000 (encoding a putative zinc finger protein) (8B.1 to 8B.6) and PF3D7_0420100 (encoding the Rio2 serine/threonine protein kinase) (8C.1 to 8C.2) sequences of 23 piperaquine-resistant and 8 piperaquine-sensitive culture-adapted lines phenotyped using in-vitro PSA. List of the positions with variable proportions of wild type and mutant nucleotides of PF3D7_0420000 (encoding a putative zinc finger protein) and PF3D7_0420100 (encoding the Rio2 serine/threonine protein kinase) sequences of 23 piperaquine-resistant (lines 6395, 6341, 6280, 6246, 6293, 6391, 6272, 6218, 6302, 6229, 6443, 6430, 6365, 6429, 6394, 6219, 6408, 6224, 6431, 6320, 6261, 6411, 6427) and 8 piperaquine-sensitive (lines 3D7, 6273, 6337, 6267, 6403, 6349, 6237, 6410, 6369) culture-adapted lines phenotyped using in-vitro PSA (Multalin online software). SNP (position 896588) in PF3D7_0420000 gene (encoding a putative zinc finger protein) ($p<3.5\times10^{-7}$, Fisher's exact test) and SNP (position 908385) in PF3D7_0420100 gene (encoding the Rio2 serine/threonine protein kinase) ($p<3.5\times10^{-7}$, Fisher's exact test) detected as significant between piperaquine-resistant and piperaquine-sensitive parasite lines are shown in bold font. Nucleotide code (IUPAC nomenclature): A: Adenine, C: Cytosine, G: Guanine, T: Thymine, R: A or G, Y: C or T, S: G or C, W: A or T, K: G or T, M: A or C, B: C or G or T, D: A or G or T, H: A or C or T, V: A or C or G, N: any base. If an indel is observed (>20% of the genome-wide mean coverage), letters are shown in lowercase.

DETAILED DESCRIPTION

A. Introduction

Figure 1A:
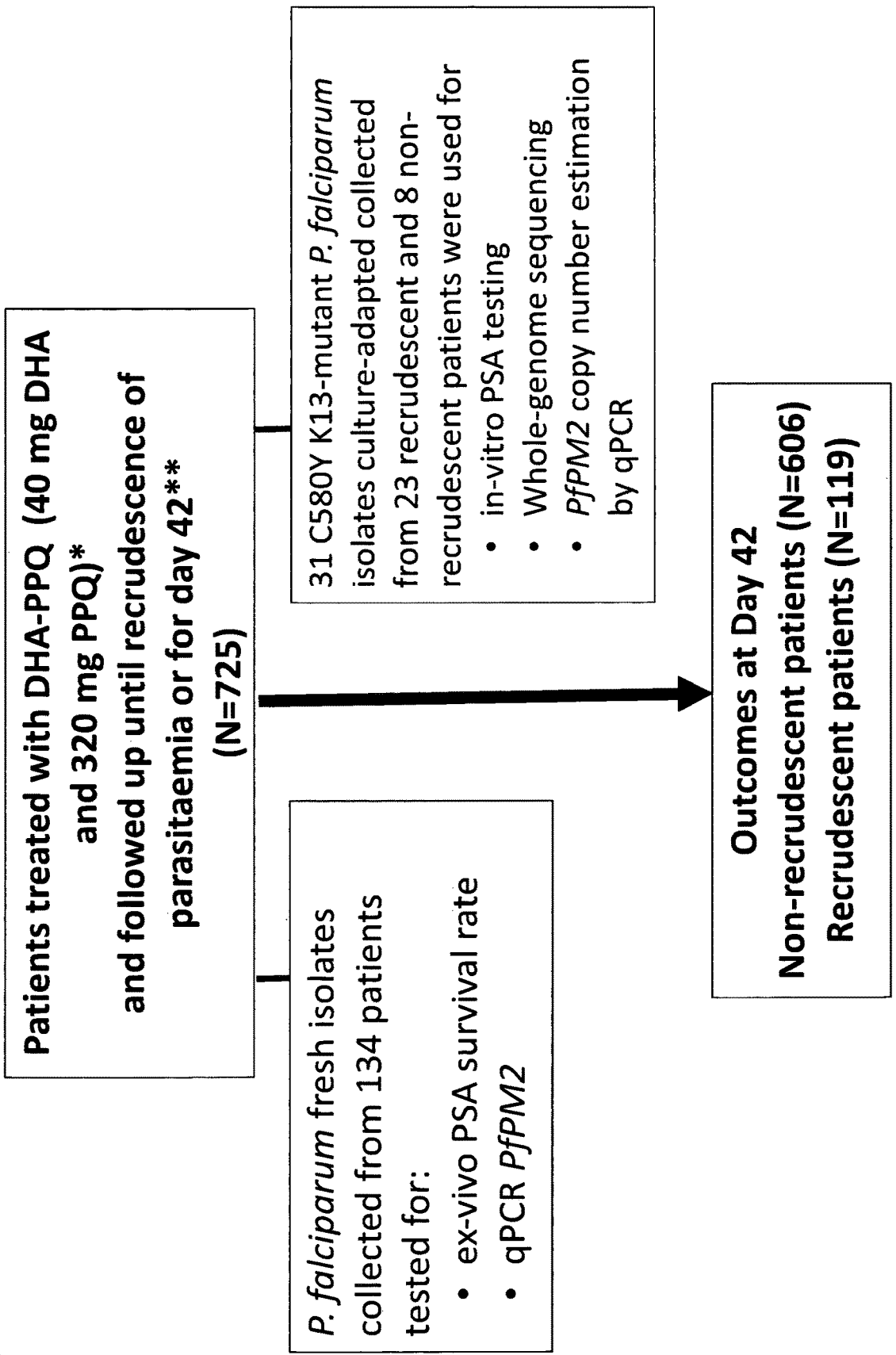
FIG. 1 shows a flow chart of patients enrolled in clinical studies conducted in 2009-2015 in 12 provinces across Cambodia to evaluate the efficacy of 3-day DHA-PPQ regimen, and isolates used to detect molecular signatures associated with in-vitro PSA resistance and DHA-PPQ clinical failure. * Supervised DHA-PP was administered once daily for 3 days (day 0, 24 h, 48 h). Dosing was based on body weight, as follows: (i) <19 kg=40 mg DHA-320 mg PPQ/day; (ii) 19-29 kg-60 mg DHA-480 mg PPQ/day; (iii) 30-39 kg=80 mg DHA-640 mg PPQ/day; (iv) >40 kg=120 mg DHA-960 mg PPQ/day, For children unable to swallow tablets, DHA-PP was dissolved in 5 ml of water. Patients were observed for 1 h post-dosing and were re-dosed with a full or half dose if vomiting occurred within 30 min or between 31 and 60 min, respectively. Those who vomited after the second dose were withdrawn from the study and were given parenteral rescue treatment (intramuscular artemether). Patients with axillary temperatures of 37.5° C. were treated with paracetamol. Patients were seen daily to day 3 and then weekly for 6 weeks (day 42) for clinical examinations (axillary temperature, symptom check) and malaria blood films. Home visits were conducted if patients failed to come back for their follow-up appointments. ** Were excluded from the analysis, withdrawn patients, patients lost to follow-up, patients classifies as reinfected (based on msp1, msp2 and glurp genotypes).

Western Cambodia, the epicentre of *Plasmodium falciparum* multidrug resistance, is currently facing high rates of dihydroartemisinin-piperaquine (DHA-PPQ) treatment failures, indicating resistance to both artemisinin derivatives and piperaquine. Genetic tools to detect these multidrug-resistant parasites are needed. Artemisinin resistance can be tracked using the K13 molecular marker, but no marker exists for piperaquine resistance.

Using blood samples from *P. falciparum*-infected Cambodian patients treated with DHA-PPQ during the years 2009-2015 in-vitro and ex-vivo susceptibility profiles for a subset using piperaquine survival assays (PSA) were created. Whole-genome sequences were determined by Illumina paired-reads sequencing, copy number variations by qPCR, RNA levels by qRT-PCR, and protein levels by immunoblotting.

Whole-genome exon sequences of 31 culture-adapted parasite lines associated amplification of the plasmepsin2-3 cluster (PfPM2, PF3D7_1408000 and PfPM3, PF3D7_1408100) with in-vitro piperaquine resistance. Increased PfPM2 gene copy number correlated with ex-vivo PSA profiles of 134 isolates. In 725 blood samples collected from patients before DHA-PPQ treatment and followed-up for 42 days, multicopy PfPM2 was associated with an adjusted hazard ratio for treatment failures of 20.4 (95% CI 9.1-45.5, p<0.0010). Multicopy PfPM2 predicted DHA-PPQ failures with 0.94 (95% CI 0.88-0.98) sensitivity and 0.77 (95% CI 0.74-0.81) specificity. The proportion of multicopy PfPM2 parasites steadily increased from 2009 to 2015 in western Cambodia and in 2014-2015 for eastern Cambodia, correlating with increasing DHA-PPQ treatment failure rates in both areas. DHA-PPQ efficacy at day 42 fell below 90% when the proportion of multicopy PfPM2 parasites exceeded 22%.

The data indicate that piperaquine resistance in Cambodia is associated with amplification of PfPM2-3, encoding hemoglobin-digesting aspartic proteases. Multicopy PfPM2 constitutes a surrogate molecular marker to track piperaquine resistance. Used alone or in combination with K13 and Pfmdr1, PfPM2 provides critical information for antimalarial treatment policies and containment measures.

Based in part on these data, this invention provided methods and reagents for detecting and treating piperaquine-resistant *Plasmodium falciparum* malaria.

B. Methods of Genotyping a *Plasmodium* and/or for Detecting a *Plasmodium* Infection The invention encompasses methods for genotyping a *Plasmodium* and/or detecting a *Plasmodium* infection, particularly *Plasmodium falciparum*. In a preferred embodiment, the method comprises providing a sample containing a *Plasmodium* and detecting the presence or absence of an increased copy number of the genomic plasmepsin2-3 cluster in the sample. The presence or absence of an increased copy number of the genomic plasmepsin2-3 cluster is detected by routine techniques in the art. For example, the techniques described in the examples, or elsewhere herein, can be used.

An increased copy number of the genomic plasmepsin2-3 cluster can be detected by numerous techniques known in the art, such as sequencing, hybridization, or amplification assays. The data in the examples indicates that an increase in copy number of the genomic plasmepsin2-3 cluster results in an increase in PfPM2 mRNA level. Therefore, an assay that measures the level of PfPM2 mRNA may be used to detect the presence or absence of an increase in copy number of the genomic plasmepsin2-3 cluster. The data in the examples indicates that an increase in copy number of the genomic plasmepsin2-3 cluster results in an increase in PfPM2 protein level. Therefore, an assay that measures the level of PfPM2 protein may be used to detect the presence or absence of an increase in copy number of the genomic plasmepsin2-3 cluster. A skilled artisan will appreciate that these examples are not limiting.

Within the context of this invention, a "an increase in copy number of the genomic plasmepsin2-3 cluster" means more than one copy of the genomic plasmepsin2-3 cluster in each haploid genome of a *Plasmodium*. In some embodiments a total of two copies are present. In some embodiments a total of three copies are present. In some embodiments a total of four copies are present. In some embodiments a total of from two to four copies are present. In some embodiments more than four copies are present.

Figure 9A:
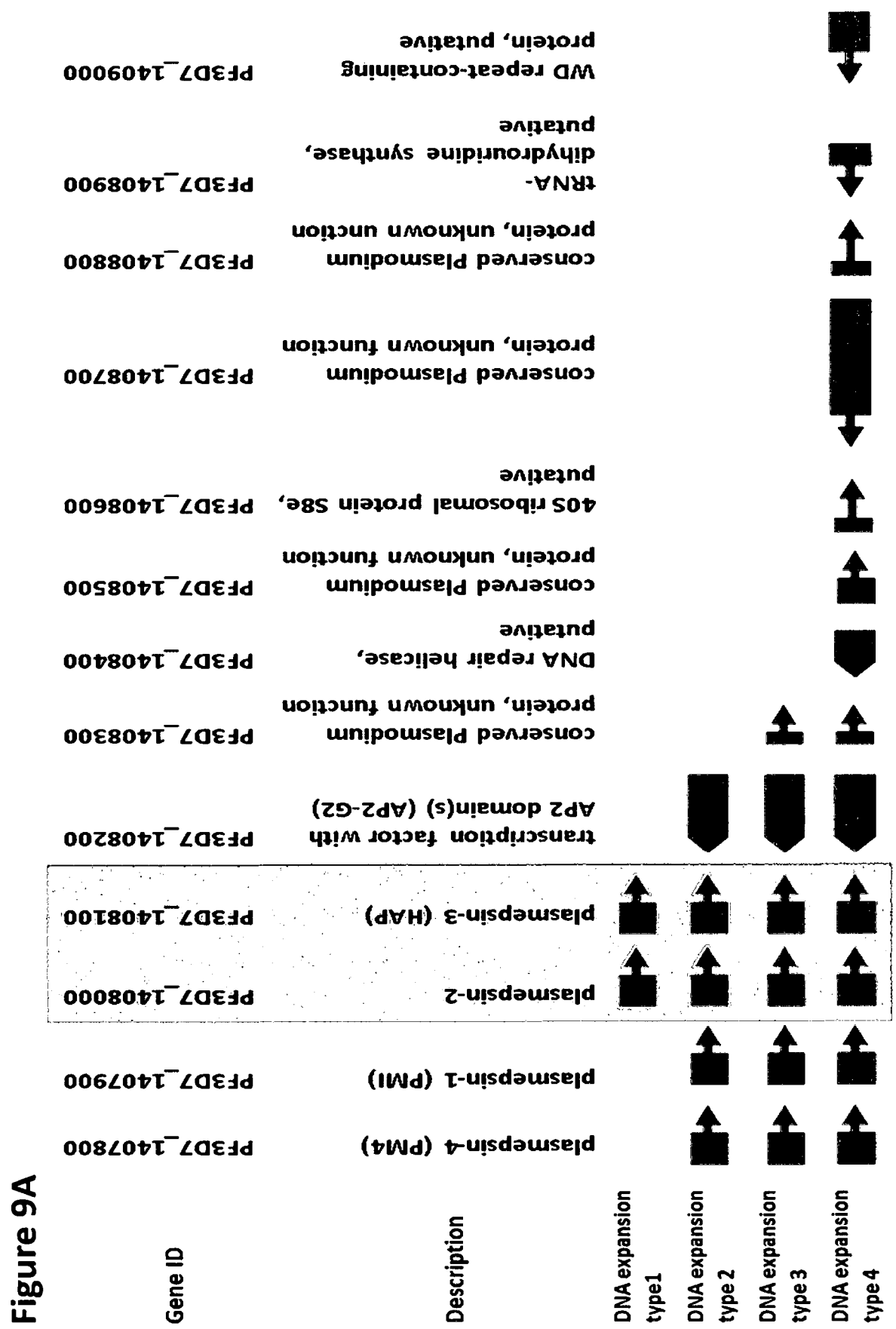
FIGS. 9A to 9E show profiles of DNA expansion in the region of genes encoding proteins involved in hemoglobin-degrading activities positively associated with in vitro piperaquine resistance and methodology developed to confirm the four DNA expansion profiles. (A) shows four observed types of DNA expansion. (B) shows DNA expansion type 1. (C) shows DNA expansion type 2. (D) shows DNA expansion type 3. (E) shows DNA expansion type 4.

Within the context of this invention, "the genomic plasmepsin2-3 cluster" means a fragment of *Plasmodium* genomic DNA that includes at least the PfPM2 and PfPM3 coding sequences and the intervening genomic DNA. In some embodiments the genomic plasmepsin2-3 cluster comprises the plasmepsin-4 (PfPM4), plasmepsin-1 (PfPM1), PfPM2, PfPM3, and transcription factor with AP2 domains(s) (AP2-G2) coding sequences and the intervening genomic DNA. In some embodiments the genomic plasmepsin2-3 cluster is selected from DNA expansion type 1, DNA expansion type 2, DNA expansion type 3, and DNA expansion type 4, as shown in FIG. 9A. In some embodiments the genomic plasmepsin2-3 cluster is no more than 10 kb or no more than 5 kb in size.

In some embodiments the presence of increased copy number of the genomic plasmepsin2-3 cluster in the sample is detected by sequencing. In some embodiments the presence of increased copy number of the genomic plasmepsin2-3 cluster in the sample is detected by PCR. In a preferred embodiment the PCR is quantitative PCR (qPCR).

In some embodiments the method comprises determining the copy number of at least one of the Pfplasmepsin2 (PF3D7_1408000) gene (PfPM2) and the Pfplasmepsin3 (PF3D7_1408100) gene (PfPM3). As shown in the examples, the copy number of the PfPM2 gene can serve as a proxy for the copy number of the genomic plasmepsin2-3 cluster. The data in the examples also indicate that the copy number of the PfPM3 gene can serve as a proxy for the copy number of the genomic plasmepsin2-3 cluster.

In some embodiments the method comprises determining the level of at least one mRNA selected from a PfPM2 mRNA and a PfPM3 mRNA. In some embodiments the method comprises determining the level of at least one protein selected from a PfPM2 protein and a PfPM3 protein.

Within the context of this invention, a "mutant *P. falciparum* K-13 propeller nucleic acid" means a nucleic acid sequence having one or more difference from the wild type sequence of *P. falciparum* K-13 propeller nucleic acid that results in a difference of at least one amino acid from the wild type amino acid sequence of the encoded protein. Within the context of this invention, a "mutant *P. falciparum* K-13 propeller protein" means an amino acid sequence having one or more difference from the wild type *P. falciparum* K-13 propeller protein.

In various embodiments, the method comprises detecting the presence or absence of a wild-type or mutated K-13 propeller protein in the cell sample. This can be performed by using specific antibodies that discriminate between wild-type and mutant K-13 propeller proteins. These antibodies can be contacted with patient samples and the presence or absence of a wild-type or mutated K-13 propeller proteins can be determined by detecting the presence or absence of an immunological reaction. Preferably, the method comprises an ELISA assay.

In a preferred embodiment, the method comprises providing a sample containing a *Plasmodium* and detecting the presence of a mutated K-13 propeller nucleic acid or protein in the sample. Preferably, the presence of a mutated K-13 propeller nucleic acid in the sample is detected by sequencing or by PCR. For example, the presence of a mutated K13-propeller nucleic acid in a sample is detected according to anyone of the methods disclosed in WO 2015/071759 A1.

In a particular embodiment the method comprises detecting the number of copies (in particular detecting 2 copies) of PfPM2 gene disclosed herein, and detecting a C580Y K13 allele.

Preferably, the *Plasmodium* is selected from *Plasmodium falciparum, Plasmodium vivax, Plasmodium ovale curtisi, Plasmodium ovale wallikeri, Plasmodium malariae, Plasmodium knowlesi, Plasmodium brasilianum, Plasmodium cynomolgi, Plasmodium cynomolgi bastianellii, Plasmodium imi, Plasmodium rhodiani, Plasmodium schweitzi, Plasmodium semiovale, Plasmodium simium, Plasmodium berghei, Plasmodium yoelii,* and *Plasmodium chabaudi.*

The invention encompasses methods for the detection of a *Plasmodium* infection and diagnosis of the infection in a patient suspected to be infected. Patients can be diagnosed by providing a cell sample from a patient. In a preferred embodiment, the method comprises providing a cell sample from a patient and detecting the presence or absence of an increased copy number of the genomic plasmepsin2-3 cluster in the sample.

The cell sample can be any cell sample obtained from patient that contains *Plasmodium*. Preferably, the cell sample is generated by drawing blood. The cell sample is preferably a blood sample. The blood sample can be further processed to culture the *Plasmodium* in the sample in vitro. For example, the techniques described in van Schalkwyk et al. Malaria Journal 2013, 12:320 can be used.

In one embodiment, the method comprises providing a blood sample from patient; optionally culture the *Plasmodium* in the sample in vitro, and detecting the presence or absence of an increased copy number of the genomic plasmepsin2-3 cluster in the sample.

In one embodiment, the method comprises providing a blood sample from a patient and detecting the presence or absence of an increased copy number of a plasmepsin2-3 nucleic acid or protein in the sample.

Preferably, PCR (and more preferable qPCR), nucleic acid hybridization, or nucleic acid sequencing is used to detect the presence or absence of an increased copy number of the genomic plasmepsin2-3 cluster in a cell sample. Any sequencing method known in the art can be employed. As used herein, the term "sequencing" is used in a broad sense and refers to any technique known by the skilled person including but not limited to Sanger dideoxy termination sequencing, whole-genome sequencing, sequencing by hybridization, pyrosequencing, capillary electrophoresis, cycle sequencing, single-base extension sequencing, solid-phase sequencing, high-throughput sequencing, massively parallel signature sequencing (MPSS), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLID® sequencing, MS-PET sequencing, mass spectrometry, and a combination thereof. In specific embodiments, the method of the invention is adapted to run on ABI PRISM® 377 DNA Sequencer, an ABI PRISM® 310, 3100, 3100-Avant, 3730, or 3730×1 Genetic Analyzer, an ABI PRISM® 3700 DNA Analyzer, or an Applied Biosystems SOLID™ System (all from Applied Biosystems), a Genome Sequencer 20 System (Roche Applied Science). Any nucleic acid hybridization method known in the art can be employed, see, e.g. Kim, Ji Hun; Kalitsis, Paul; Pertile, Mark D; Magliano, Dianna; Wong, Lee; Choo, Andy; and Hudson, Damien F (August 2012) Nucleic Acids: Hybridisation. In: eLS. John Wiley & Sons, Ltd: Chichester.DOI: 10.1002/9780470015902.a0003148.pub2). In a preferred embodiment at least one of the following hybridization probes is used for hybridization: 5'-caattcaacatttgatggattaaacattga-3' (SEQ ID NO.20) for PfPM2; 5'-tgaagaatcctt-taacacgtttcgagtaac-3' (SEQ ID NO.21) for PfPM3.

In one embodiment, the method comprises detecting an amplified nucleic acid product. The starting nucleic acid that is amplified may be DNA and/or RNA. Any suitable method known in the art may be used.

For example, the amplification method can be RCA, MDA, NASBA, TMA, SDA, LCR, b-DNA, PCR (all forms including RT-PCR), RAM, LAMP, ICAN, SPIA, QB-replicase, or Invader. A preferred amplification method is the polymerase chain reaction (PCR) amplification. See, e.g., PCR Technology: Principles and Applications for DNA Amplification (Ed. H. A. Erlich, Freeman Press, NY, N.Y., 1992); PCR Protocols: A Guide to Methods and Applications (Eds. linis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675. More preferred PCR methods is real-time PCR, PCR-HRM (High-Resolution DNA Melting) (see Andriantsoanirina et al. Journal of Microbiological Methods, 78:165 (2009)) and PCR coupled to ligase detection reaction based on fluorescent microsphere (Luminex® microspheres). This last method permits to perform a multiplex assay to detect several locus in a same time.

Other preferred amplification methods include the ligase chain reaction (LCR) (e.g., Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), and nucleic acid based sequence amplification (NABSA) (U.S. Pat. Nos. 5,130,238, 5,409,818, 5,554,517, and 6,063,603). Other amplification methods that may be used are described in U.S. Pat. Nos. 5,242,794, 5,494,810, 4,988,617 and 6,582,938. The above references regarding amplification of nucleic acids are specifically incorporated by reference with respect to the disclosure therein of the specific reaction conditions used for amplification in each of the amplification methods.

In a preferred embodiment, at least one of the following primers is used for amplification: 5'-TGGT-GATGCAGAAGTTGGAG-3' ID (SEQ NO.1); 5'-TGGGACCCATAAATTAGCAGA-3' (SEQ ID NO.2);

5'-GGATTCGAACCAACTTATACTGC-3' (SEQ ID NO.3); and 5'-AATTGGATCTACTGAACCTATTGATAA-3' (SEQ ID NO.4)

In one embodiment, RNA is extracted and reverse-transcribed into cDNA. Amplification or sequencing is then performed on the cDNA. Otherwise northern hybridization can be performed directly on extracted RNA.

Thus, the method can comprise isolating RNA from a sample from a patient, reverse-transcribing the RNA into cDNA, amplifying or sequencing the cDNA, or northern hybridizing the RNA, and determining the presence or absence of an increased copy number of the genomic plasmepsin2-3 cluster in the sample.

In various embodiments, the method comprises detecting the presence or absence of an increased amount of a protein encoded by the plasmepsin2-3 cluster in the sample. As shown in the examples, this approach may be used to detect an increase in copy number of the plasmepsin2-3 cluster. This can be performed by using specific antibodies that detect the PfPM2 and/or PfPM3 proteins. These antibodies can be contacted with patient samples and the presence or absence of an increased amount of PfPM2 and/or PfPM3 proteins can be determined by detecting the presence or absence of an immunological reaction. Preferably, the method comprises an ELISA assay.

Antibodies can be synthetic, monoclonal, or polyclonal and can be made by techniques well known in the art. Such antibodies specifically bind via the antigen-binding sites of the antibody (as opposed to non-specific binding). PfPM2 and/or PfPM3 polypeptides, fragments, variants, fusion proteins, etc., can be employed as immunogens in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, Immuno Biology 3:9 (Garland Publishing Inc., 2nd ed. 1996)). Because folded proteins have complex surfaces, the number of epitopes available is quite numerous; however, due to the conformation of the protein and steric hinderances, the number of antibodies that actually bind to the epitopes is less than the number of available epitopes (C. A. Janeway, Jr. and P. Travers, Immuno Biology 2:14 (Garland Publishing Inc., 2nd ed. 1996)). Epitopes can be identified by any of the methods known in the art. Both polyclonal and monoclonal antibodies can be prepared by conventional techniques.

PfPM2 and/or PfPM3 peptides based on the amino acid sequence of wild-type and PfPM2 and/or PfPM3 proteins can be utilized to prepare antibodies that specifically bind to PfPM2 and/or PfPM3 proteins. The term "antibodies" is meant to include polyclonal antibodies, monoclonal antibodies, fragments thereof, such as F (ab') 2 and Fab fragments, single-chain variable fragments (scFvs), single-domain antibody fragments (VHHs or Nanobodies), bivalent antibody fragments (diabodies), as well as any recombinantly and synthetically produced binding partners.

Antibodies are defined to be specifically binding if they bind to their target protein with a Ka of greater than or equal to about 10⁷ Mol. Affinities of binding partners or antibodies can be readily determined using conventional techniques, for example those described by Scatchard et al., Ann. N.Y. Acad. Sci., 51:660 (1949).

Polyclonal antibodies can be readily generated from a variety of sources, for example, horses, cows, goats, sheep, dogs, chickens, rabbits, mice, or rats, using procedures that are well known in the art. In general, purified PfPM2 and/or PfPM3 proteins or a peptide based on the amino acid sequence of PfPM2 and/or PfPM3 proteins that is appropriately conjugated is administered to the host animal typically through parenteral injection. The immunogenicity of PfPM2 and/or PfPM3 proteins can be enhanced through the use of an adjuvant, for example, Freund's complete or incomplete adjuvant. Following booster immunizations, small samples of serum are collected and tested for reactivity to PfPM2 and/or PfPM3 proteins. Examples of various assays useful for such determination include those described in Antibodies: A Laboratory Manual, Harlow and Lane (eds.), Cold Spring Harbor Laboratory Press, 1988; as well as procedures, such as countercurrent immuno-electrophoresis (CIEP), radioimmunoassay, radio-immunoprecipitation, enzyme-linked immunosorbent assays (ELISA), dot blot assays, and sandwich assays. See U.S. Pat. Nos. 4,376,110 and 4,486,530.

Monoclonal antibodies can be readily prepared using well known procedures. See, for example, the procedures described in U.S. Pat. Nos. 4,902,614, 4,543,439, and 4,411,993; Monoclonal Antibodies, Hybridomas: A New Dimension in Biological Analyses, Plenum Press, Kennett, McKeam, and Bechtol (eds.), 1980.

For example, the host animals, such as mice, can be injected intraperitoneally at least once and preferably at least twice at about 3 week intervals with isolated and purified PfPM2 and/or PfPM3 proteins or conjugated PfPM2 and/or PfPM3 peptides, optionally in the presence of adjuvant. Mouse sera are then assayed by conventional dot blot technique or antibody capture (ABC) to determine which animal is best to fuse. Approximately two to three weeks later, the mice are given an intravenous boost of protein or peptide. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow for approximately eight days. Supernatants from resultant hybridomas are collected and added to a plate that is first coated with goat anti-mouse Ig. Following washes, a label, such as a labeled PfPM2 and/or PfPM3 polypeptide, is added to each well followed by incubation. Positive wells can be subsequently detected. Positive clones can be grown in bulk culture and supernatants are subsequently purified over a Protein A column (Pharmacia).

The monoclonal antibodies can be produced using alternative techniques, such as those described by Alting-Mees et al., "Monoclonal Antibody Expression Libraries: A Rapid Alternative to Hybridomas", Strategies in Molecular Biology 3:1-9 (1990), which is incorporated herein by reference. Similarly, binding partners can be constructed using recombinant DNA techniques to incorporate the variable regions of a gene that encodes a specific binding antibody. Such a technique is described in Larrick et al., Biotechnology, 7:394 (1989).

Antigen-binding fragments of such antibodies, which can be produced by conventional techniques, can also be used for detecting the PfPM2 and/or PfPM3 proteins. Examples of such fragments include, but are not limited to, Fab and F(ab')2 fragments. Antibody fragments and derivatives produced by genetic engineering techniques are also provided.

The monoclonal antibodies include chimeric antibodies, e.g., humanized versions of murine monoclonal antibodies. Such humanized antibodies can be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment can comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (Nature 332:323, 1988), Liu et al. (PNAS 84:3439, 1987), Larrick et al. (Bio/Technology 7:934, 1989), and Winter and Harris (TIPS 14:139, May 1993). Procedures to generate antibodies transgenically can be found in GB 2,272,440, U.S. Pat. Nos. 5,569,825 and 5,545,806.

Antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in Robinson et al. International Publication No. WO 87/02671; Akira, et al. European Patent Application 0184187; Taniguchi, M., European Patent Application 0171496; Morrison et al. European Patent Application 0173494; Neuberger et al. PCT International Publication No. WO 86/01533; Cabilly et al. U.S. Pat. No. 4,816,567; Cabilly et al. European Patent Application 0125023; Better et al., Science 240:1041 1043, 1988; Liu et al., PNAS 84:3439 3443, 1987; Liu et al., J. Immunol. 139:3521 3526, 1987; Sun et al. PNAS 84:214 218, 1987; Nishimura et al., Canc. Res. 47:999 1005, 1987; Wood et al., Nature 314:446 449, 1985; and Shaw et al., J. Natl. Cancer Inst. 80:1553 1559, 1988); Morrison, S. L., Science 229: 1202 1207, 1985; Oi et al., BioTechniques 4:214, 1986; Winter U.S. Pat. No. 5,225,539; Jones et al., Nature 321:552 525, 1986; Verhoeyan et al., Science 239:1534, 1988; and Beidler et al., J. Immunol. 141:4053 4060, 1988.

In connection with synthetic and semi-synthetic antibodies, such terms are intended to cover but are not limited to antibody fragments, isotype switched antibodies, humanized antibodies (e.g., mouse-human, human-mouse), hybrids, antibodies having plural specificities, and fully synthetic antibody-like molecules.

In a preferred embodiment, the method comprises detecting a *Plasmodium* infection. The method can further comprise determining whether the *Plasmodium* has an increased copy number of the genomic plasmepsin2-3 cluster using any method of this disclosure.

Methods of Treating a *Plasmodium* Infection

The invention encompasses methods for treating a *Plasmodium* infection. In one embodiment, the method comprises determining whether a patient is infected by a *Plasmodium* containing an increased copy number of the genomic plasmepsin2-3 cluster and adjusting the anti-parasitic treatment based on whether patient is infected by a *Plasmodium* containing an increased copy number of the genomic plasmepsin2-3 cluster.

In a preferred embodiment, if the patient is infected by a *Plasmodium* that does not have an increased copy number of the genomic plasmepsin2-3 cluster, the patient is treated with piperaquine. In a more preferred embodiment the patient is treated with artemisinin or artemisinin derivatives and with piperaquine.

In a preferred embodiment, if the patient is infected by a *Plasmodium* that does have an increased copy number of the genomic plasmepsin2-3 cluster, the patient is treated with an anti-parasitic treatment without piperaquine.

Accordingly, the invention also relates to the use of piperaquine for the treatment of patients who have previously been submitted to a method of in vitro assessment of an increased copy number of the genomic plasmepsin2-3 cluster and wherein said assessment has revealed no such increase. Piperaquine may be used in association with artemisinin or artemisinin derivatives.

The invention also relates to the use of anti-parasitic (especially anti-malarial) treatment without piperaquine for the treatment of patients who have previously been submitted to a method of in vitro assessment of an increased copy number of the genomic plasmepsin2-3 cluster and wherein said assessment has revealed such increase.

Kits for Genotyping and/or Detecting and/or Treating a *Plasmodium* Infection

Kits for detecting a *Plasmodium* infection are also provided. In some embodiments the kits comprise primers for the amplification of a plasmepsin2-3 cluster nucleic acid and reagents for the detection of the amplified product. In some embodiments the kit comprises a probe for detecting a plasmepsin2-3 cluster nucleic acid. In some embodiments the probe is labeled with a fluorescent, radioactive or enzymatic label. In some embodiments the kit detects a PfPM2 nucleic acid. In some embodiments the kit detects a PfPM3 nucleic acid. In some embodiments the kit comprises at least one of the following primers: 5'-TGGT-GATGCAGAAGTTGGAG-3' (SEQ ID NO.1); 5'-TGGGACCCATAAATTAGCAGA-3' (SEQ ID NO.2); 5'-GGATTCGAACCAACTTATACTGC-3' (SEQ ID NO.3); and 5'-AATTGGATCTACTGAACCTATTGATAA-3' (SEQ ID NO.4). In some embodiments the kit comprises at least one probe comprising the sequence 5'-CAACATTT-GATGGTATCCTTGGTTTAGGATGGA-3' (SEQ ID NO.5). In some embodiments the kit comprises the following probe: 5'-FAM-CAACATTTGATGGTATCCTTGGTT-TAGGATGGA-BHQ1-3' (SEQ ID NO.6). In some embodiments the kit further comprises primers for the amplification of a K-13 propeller nucleic acid and reagents for the detection of the amplified product. In some embodiments the kit further comprises primers for the amplification of a Pfmdr1 nucleic acid and reagents for the detection of the amplified product.

Preferably, the kit comprises a probe for detecting a plasmepsin2-3 cluster nucleic acid. Preferably, the probe is labeled with a fluorescent or enzymatic label. In a preferred embodiment the probe is labeled with a combination of FAM and BAQ1 labels.

EXAMPLES

Example 1: Materials and Methods

A. Study sites and patients

Figure 5:
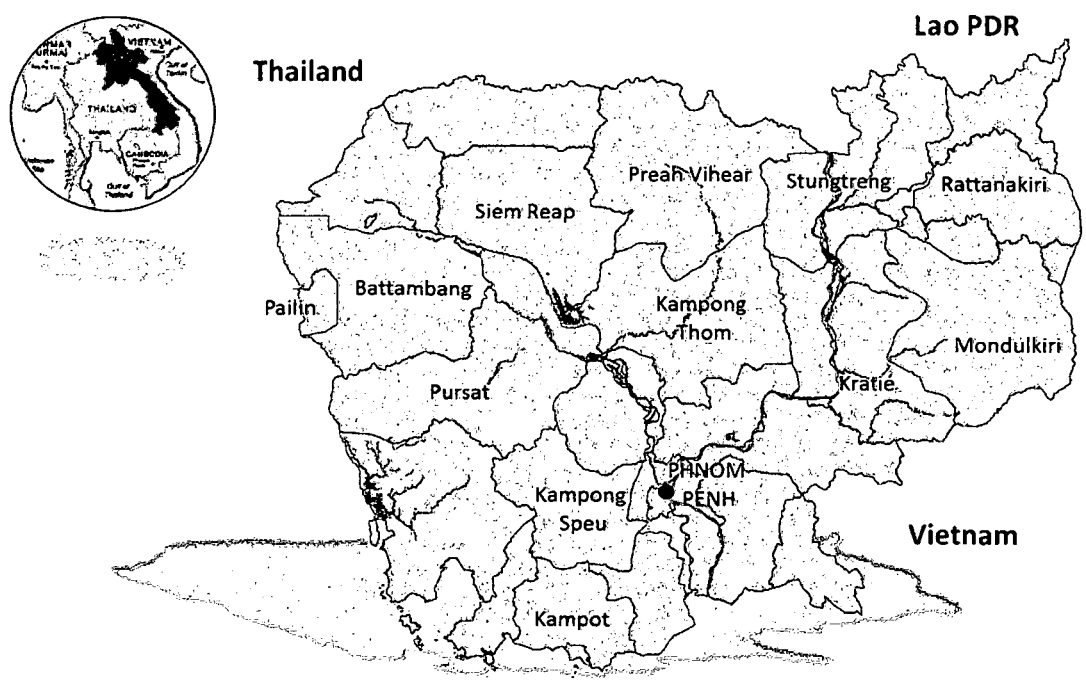
FIG. 5 shows a map of Cambodia showing the location of the study sites (provinces) where dihydroartemisinin-piperaquine (DHA-PPQ) clinical efficacy studies (42-day follow-up) were conducted in 2009-2015.

Patients with *P. falciparum* malaria were enrolled in clinical studies conducted at health centers located across Cambodia during the years 2009-2015 (FIG. 5). After obtaining written informed consent, patients were treated with DHA-PPQ (Duo-Cotecxin®, dihydroartemisinin 40 mg and piperaquine 320 mg, Zhejiang Holley Nanhu Pharamaceutical Co. Ltd, China) and followed up for 42 days as previously described.[7,8,10] The endpoint to evaluate DHA-PPQ efficacy was the proportion of PCR-corrected recrudescent *P. falciparum* infections at day 42.[11] All studies were approved by the Ethical Committee for Health Research of the Cambodian Ministry of Health. Clinical trials were registered at the Australian New Zealand Clinical Trials Registry (ACTRN 12615000793516, 12612000184875, 12612000183886, 12612000181808 and 12614000344695).

B. Sample Collection

Blood samples were collected into acid-citrate-dextrose tubes (Becton-Dickinson, USA) before treatment and sent to Institut Pasteur in Cambodia within 24 hours. A sub-set of freshly collected samples was used to perform the ex-vivo PSA.[7] All samples were cryopreserved in glycerolyte. Red cell pellets were stored at −20° C. for molecular studies. Blood spots were prepared on day 0 and when applicable on the day of recrudescence.

C. Laboratory Investigations

Cryopreserved parasites were culture-adapted as described.[12] Susceptibility to PPQ was investigated using in-vitro PSA for culture-adapted parasites and ex-vivo PSA for fresh isolates. Survival rates were assessed microscopically and parasites with a survival rate ≥10% were considered PPQ-resistant.[7] msp1, msp2 and glurp polymorphisms were determined to distinguish recrudescent from new infections.[13] Sequencing of the K13-propeller domain was used to screen for ART-resistance.[1] Whole-genome sequencing was performed using Illumina paired-reads sequencing.[1] Data were integrated into the Whole-genome Data Manager (WDM) database[14] and exomes of PPQ-resistant and -sensitive lines were compared after excluding low-coverage positions (i.e., lower than 25% of the genome-wide mean coverage). Genes from highly variable multigene families (var, rifin, phist and stevor) were excluded.[1] CNVs and SNPs were investigated using PlasmoCNVScan and Phen2gen software (see below). 1+PfPM2 and Pfmdr1 copy number was determined by qPCR (see below). Steady-state PfPM2 mRNA levels were measured by RT-qPCR (see below) and PfPM2 protein expression by immunoblotting (see below).

D. Piperaquine Survival Assays (PSA)

In-vitro susceptibility to PPQ was investigated using the in-vitro or the ex-vivo PSA, which is based on exposing very early ring-stage parasites to 200 nM PPQ for 48 hours, washing away the drug, and assessing parasite growth after a further 24 hours of culture. Survival rates at the 72 hour time point were assessed microscopically by counting the proportion of viable parasites in exposed and non-exposed cultures that developed into second-generation rings or trophozoites with normal morphology. Parasites with a survival rate ≥10% were considered PPQ-resistant.[5]

E. DNA, RNA and Protein Extraction.

Parasite DNA was extracted from blood spots with Instagen matrix (Bio-Rad, Marnes-la-Coquette, France), and from whole blood or cultured parasites with QIAamp DNA Blood MiniKit (Qiagen, Valencia, CA). Total RNA was isolated from cultured parasites using a Trizol reagent-based protocol (Life Technologies, Courtaboeuf, France) and purified with the RNeasy Mini Kit (Qiagen, Valencia, CA). Samples were DNase-treated (Life Technologies) to remove any contaminating genomic DNA. Proteins were extracted from cultured parasites that had been lysed with 0.15% saponin in PBS. The parasite pellet was washed four times with PBS, resuspended at 400,000 parasites per µL of PBS with 1× protease inhibitor cocktail (Sigma-Aldrich, St. Louis, MO, USA) and lysed with a BioRuptor Twin (10 cycles of 10 seconds each, low intensity).

F. Whole-Genome Sequencing

Image analysis, base calling and error estimation used the Illumina Analysis Pipeline version 1.7. Raw sequence files were filtered using Fqquality tool. Trimmed reads from controlled Fastq files were mapped onto the *P. falciparum* 3D7 reference genome with the Burrows-Wheeler Alignment (BWA), generating BAM files (binary files of tab-delimited format SAM). Samtools was used to prepare pileup files, which were formatted using in-house software to integrate the data into the Whole-genome Data Manager (WDM) database.[15] Exomes of PPQ-resistant and -sensitive culture-adapted lines were compared after excluding positions with coverage lower than 25% of the genome-wide mean. SNPs were explored after excluding genes from highly variable multi-gene families (var, rifin, phist and stevor), as described.1

Copy Number Variations (CNVs) and Single Nucleotide Polymorphisms (SNPs) (after excluding indels) were investigated using PlasmoCNVScan and Phen2gen software's, respectively. 15

PlasmoCNVScan, a C/C++ software was used to normalize read depth along the genome and by-pass the risk of a non-uniform sequencing process (i.e., the number of reads mapped to a region is assumed to follow a Poisson distribution and is proportional to the number of copies) and the need to mapped reads with a well-annotated reference genome. The underlying concept of read depth-based methods is that the depth of coverage in a genomic region is correlated with the copy number of the region. Firstly, we computed the average frequency for each motif found across the whole exome: this is the theoretical coverage for a motif. We defined the observed coverage as the local coverage for a motif for each position (extracted from pileup file). Then, for each gene (except genes with nucleotide sequence lengths less than 500 bp which were excluded), we used a sliding window and computed the ratio between observed coverage and theoretical coverage for each gene/position. This ratio gave the estimated copy number variation for this region. We considered CNV as a continuous variable and used the Student t-test to compare CNVs in genes of PPQ-resistant and -sensitive parasite lines. CNVs were also classified according to their Wilcoxon rank-sum values to detect amplification or de amplification events. For each analysis, a Bonferroni threshold (0.05/number of genes analyzed) was used to evaluate genome-wide significance.

Phen2gen is a program developed with Perl and R software's. We conducted SNP-wise analysis and used the exact Fisher's exact test to identify significant SNPs differences between PPQ-resistant and -sensitive parasite lines. A Bonferroni threshold (0.05/number of SNPs analyzed) was used to evaluate genome-wide significance.

G. Immunoblotting.

Parasite lysates (synchronized trophozoite-stage cultures; 24-30 hours post invasion), were mixed with complete Laemmli buffer and boiled for 10 minutes at 95 C. Samples were run on a 10% Tris-Gly-SDS precast gel (BioRad) at 120V for 2 h with a Precision Kaleidoscope protein marker (Biorad). The gel contents were transferred to a nitrocellulose membrane (315 mA 90 minutes). Membranes were blocked with 2% nonfat dry milk and 1% BSA in TBS for 90 minutes at room temperature. Membranes were probed with antibody diluted in the blocking buffer at 4° C. overnight. Dilutions used were 1:2,000 for anti-Plasmepsin2 (gift from Dan Goldberg) and 1:5000 for anti-beta actin (Novus-Bio). Membranes were washed in TBST, then probed with the appropriate 1:10,000 secondary antibody in blocking buffer for one hour at room temperature. Membranes were washed with TBS, then treated with ECL (Pierce) and exposed to film.

H. PfPM2 and Pfmdr1 Copy Number Determination

PfPM2 (PF3D7_1408000) and Pfmdr1 (PF3D7_0523000) copy numbers were measured by qPCR using a CFX96 real-time PCR machine (Bio-Rad). As a reference, we used the single copy β-tubulin (PF3D7_1008700) gene. Listing of primers, protocols and PCR amplification efficiencies are provided in the table below.

| qPCR | Primer Sequence | Sequences | Tm (° C.) | Product size (bp) |
|---|---|---|---|---|
| PfPM2 | PfPM2_CN_F | 5'-TGGTGATGCA GAAGTTGGAG-3' (SEQ ID NO: 1) | 59.8 | 79 |
|  | PfPM2_CN_R | 5'-TGGGACCCAT AAATTAGCAGA-3' (SEQ ID NO. 2) | 59.4 |  |
|  | Pf β-tubulin_CN_F | 5'-TGATGTGCGC AAGTGATCC-3' (SEQ ID NO. 7) | 61.9 | 79 |
|  | Pf β-tubulin_CN_R | 5'-TCCTTTGTGGA CATTCTTCCTC-3' (SEQ ID NO. 8) | 60.5 |  |
| Pfmdr1 | Pfmdr1_CN_F | 5'-TGCATCTATAAAA CGATCAGACAAA-3' (SEQ ID NO. 9) | 60.0 | 87 |
|  | Pfmdr1_CN_R | 5'-TCGTGTGTTCC ATGTGACTGT-3' (SEQ ID NO. 10) | 60.0 |  |
|  | Pf β-tubulin_CN_F | 5'-TGATGTGCGC AAGTGATCC-3' (SEQ ID NO. 11) | 61.9 | 79 |
|  | Pf β-tubulin_CN_R | 5'-TCCTTTGTGGAC ATTCTTCCTC-3' (SEQ ID NO. 12) | 60.5 |  |

PfPM2 Copy Number

Quantitative PCR (qPCR) was carried out in 20 μl volumes in a 96-well plate containing 5× HOT FIREPol EvaGreen qPCR Mix ROX (Solis BioDyne, Estonia), 0.25 μM of each forward and reverse primer and 4 μl of template DNA. Final MgCl$_2$ concentrations were 2.5 mM and 4 mM for PfPM2 and Pfβ-tubulin, respectively. Amplifications were performed under the following conditions: 95° C. for 15 min, followed by 45 cycles of 95° C. for 15 s, 58° C. for 20 s, and 72° C. for 20 s.

PfPM2 copy number of each sample was measured in triplicate relative to a standard curve using five standards of mixed synthetic gene fragments (Eurofins Genomics, Ebersberg, Germany). The lengths of the synthetic fragments for PfPM2 and Pfβ-tubulin, including gene locations are for PfPM2 (PF3D7_1408000, from position 367 to 560, 193 bp): 367-aggtagttcaaatgataatatcgaattagtagattc-caaaatataatgttttat<u>ggtgatgcagaagttggagataa ccaacaaccattta-catttattcttgatacaggatctgctaatttatgggtcccaagtgttaaatgta-caactgcaggatgtttaacta</u> aacatctatatgattcatctaaatc-560 (SEQ ID NO.13); and for Pfβ-tubulin (PF3D7_1008700): from positions 1183 to 1391 (208 bp): 1183-tcaacaatacagagcct-taactgtgccggagttaacacaacaaatgttcgacgcaaaaaatat-<u>gatgtgcgcaagtgatccaagaca</u> <u>tggaagatatttaacggcatgtgctatgtttagaggaagaatgtc-cacaaaggaagttgacgaacaaatgttaaacgttcaaaata</u> aaaactcatcttat-tttgtcgaatggattcctcac-1391 (SEQ ID NO.14) (shown in bold font, the qPCR amplified portion).

The five standards of mixed synthetic gene fragments were: standard 1 (1:1 molar ratio of PfPM2 & β-tubulin), standard 2 (2:1 molar ratio of PfPM2 & β-tubulin), standard 3 (3:1 molar ratio of PfPM2 & β-tubulin), standard 4 (4:1 molar ratio of PfPM2 & β-tubulin) and standard 5 (5:1 molar ratio of PfPM2 & β-tubulin).

Figure 6A:
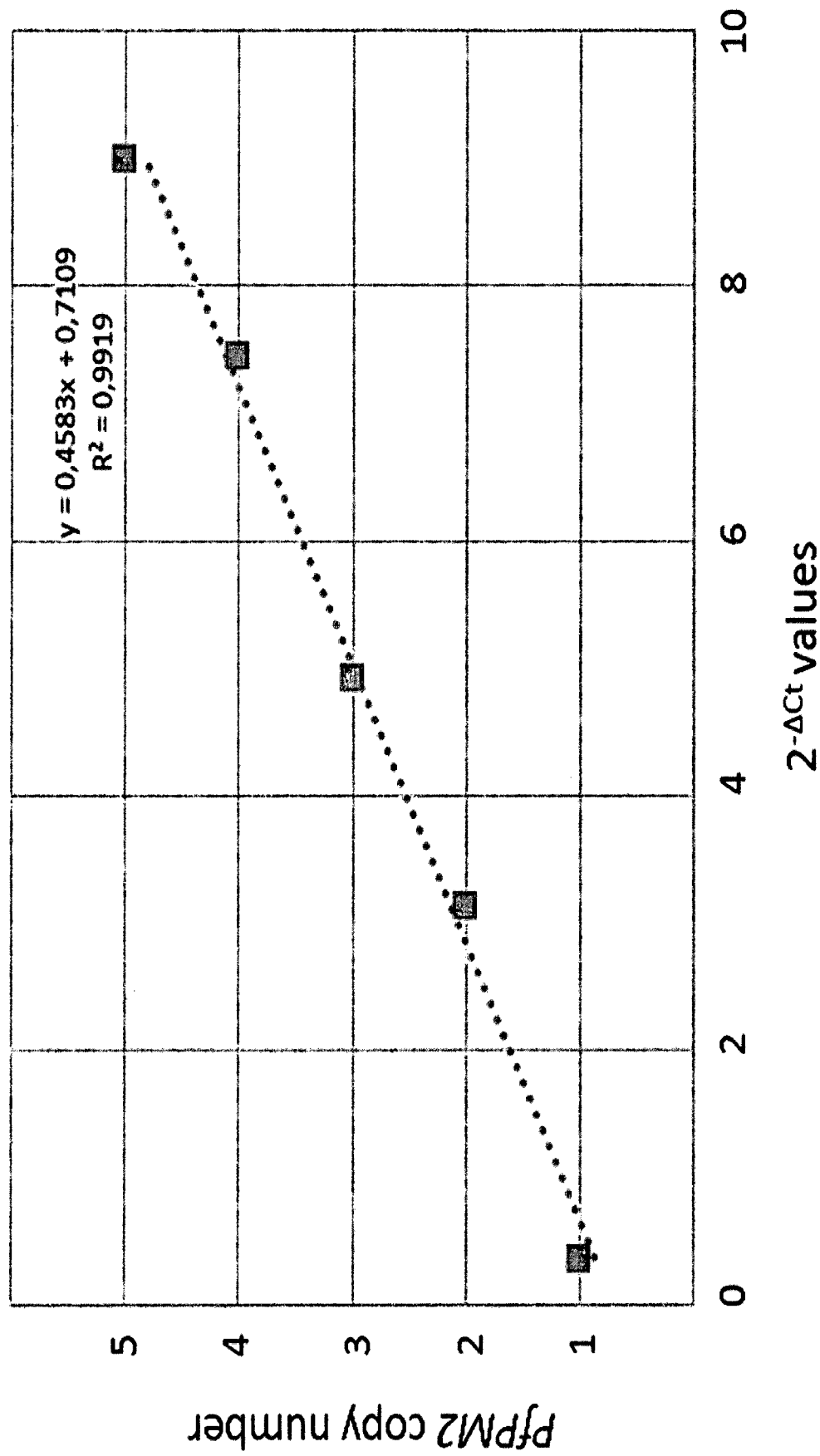
FIGS. 6A to 6D show PfPM2 and Pfmdr1 copy number determination, with listing of primers, protocols and PCR amplification efficiencies.
Figure 6B:
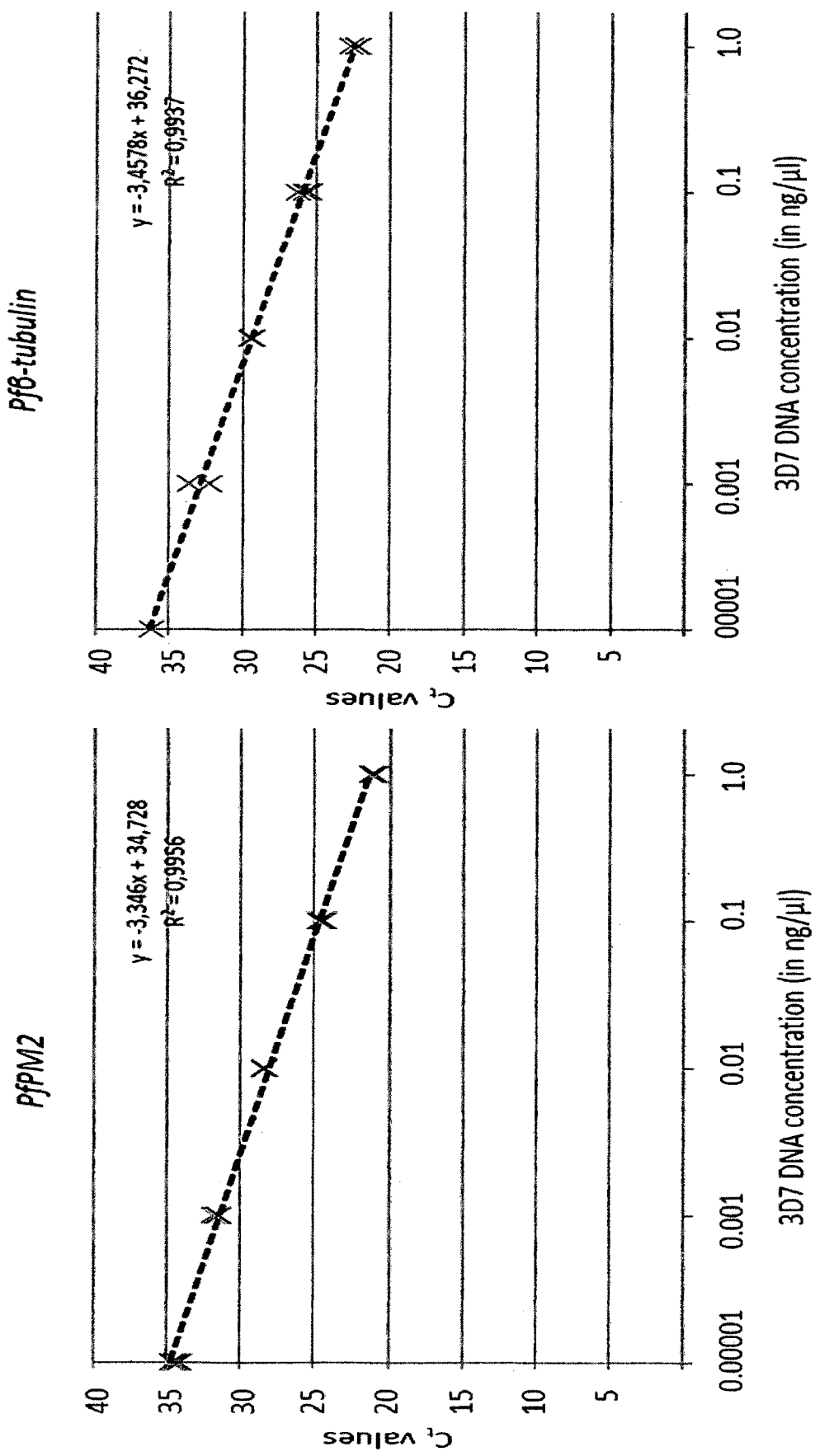

The 3D7 (Africa) line was included in each run as control (one copy of PfPM2). PfPM2 copy number was calculated by the $2^{-\Delta Ct}$ method ($\Delta C_t = C_{t\, PfPM2} - C_{t\, Pf\beta\text{-}tubulin}$ where $C_t$ is the threshold cycle) and deduced from the standard curve. (FIG. 6A.) A PfPM2 copy number >1.6 was defined as an amplification of the gene. Amplification efficiencies of the PfPM2 and the Pfβ-tubulin genes, measured using ten-fold dilutions of 3D7 DNA, were similar (99% and 95%, respectively). (FIG. 6B.)

Figure 6C:
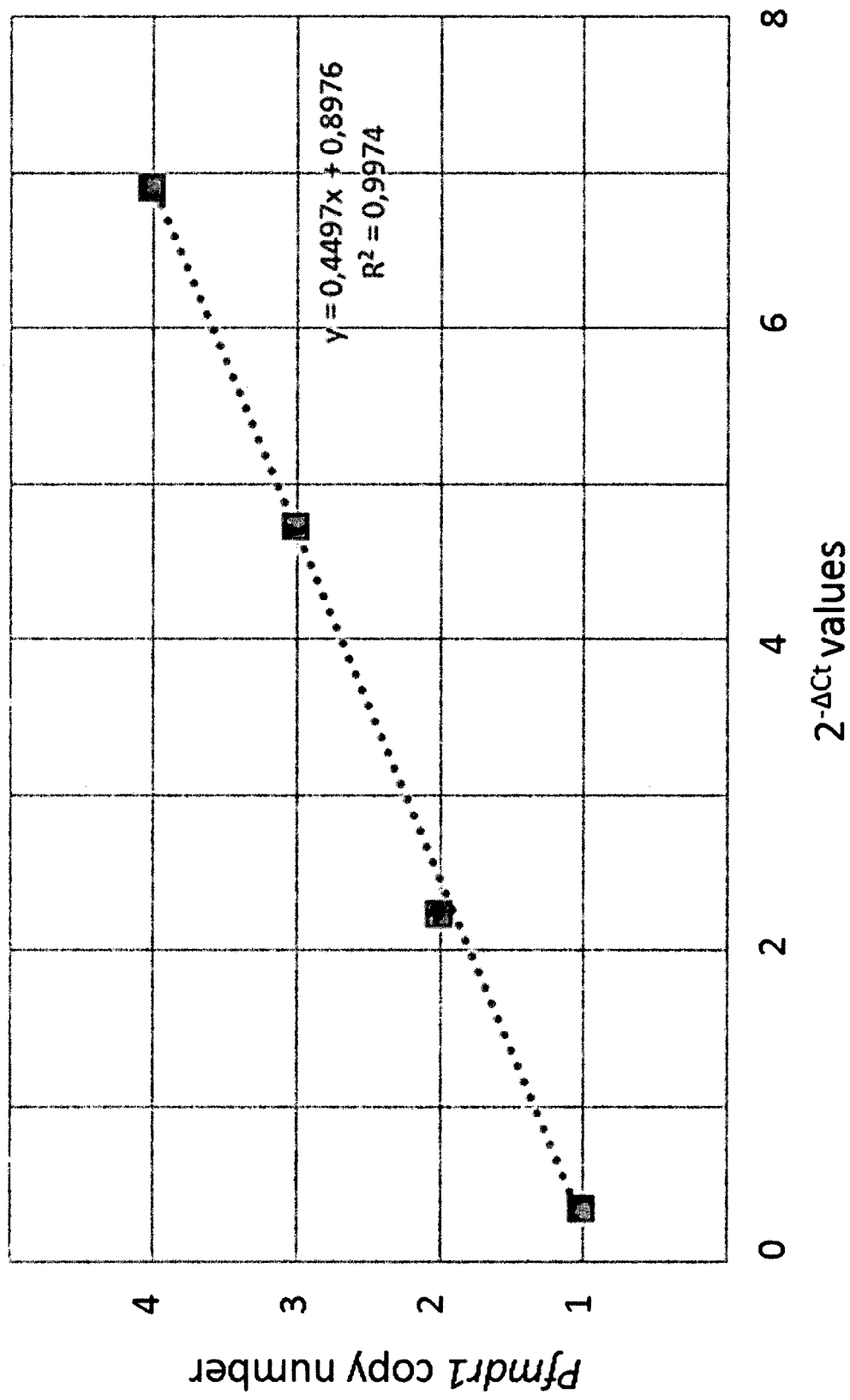

Pfmdr1 Copy Number qPCRs were carried out in 25 μl volumes in a 96-well plate containing 5× HOT FIREPol EvaGreen qPCR Mix Plus (Solis BioDyne, Estonia), 0.3 μM concentrations of each forward and reverse primers, and 4 μl of template DNA. Amplifications were performed under the following conditions: 94° C. for 15 min, followed by 40 cycles of 94° C. for 15s, 58° C. for 20s, and 72° C. for 20s. For each run, the Pfmdr1 copy number of each sample was measured in triplicate relative to a standard curve (FIG. 6C) using four standards of mixed synthetic gene fragments (Eurofins Genomics, Ebersberg, Germany). The lengths of the synthetic fragments for Pfmdr1 (F3D7_0523000), including gene location are for PfPM2 (PF3D7_1408000), from position 3981 to 4260 (204 bp): 3981-ctattgtagatattaaaga-taaagctgacaaaactattattactattgcccacagaatt<u>gcatctataaaacgatca-gacaaaattgtgg</u> <u>tatttaataaccctgatcgaaatggaacctttgtacagtcacatggaacacacgat-gaattattatcagcacaagatggaatatata</u> aaaaatatgtaaaattagctaaatga-4260 (SEQ ID NO.15) (shown in bold font, the qPCR amplified portion).

The four standards of mixed synthetic gene fragments were: from standard 1 (1:1 molar ratio of Pfmdr1 and β-tubulin) to standard 4 (4:1 molar ratio of Pfmdr-1 and β-tubulin). The 3D7 Africa line (which has one copy of Pfmdr1) and the Dd2 line (which has three copies of Pfmdr1) were included in each run as controls.

Figure 6D:
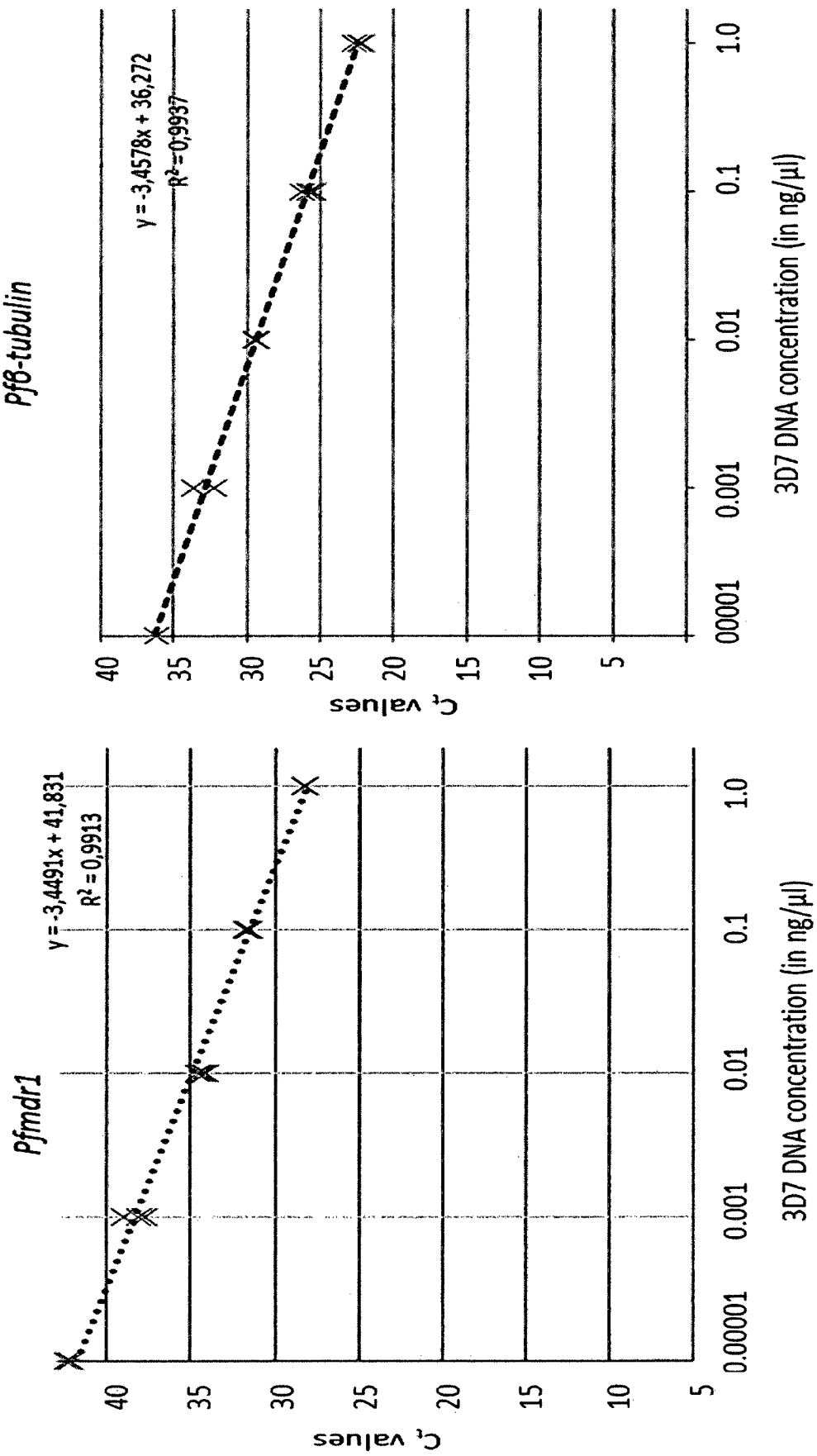

Pfmdr1 copy number was calculated by the $2^{-\Delta Ct}$ method ($\Delta C_t = C_{t\, Pfmdr1} - C_{t\, Pf\beta\text{-}tubulin}$ where $C_t$ is the threshold cycle) and deduced from the standard curve. A Pfmdr1 copy number >1.6 was defined as an amplification of the gene. Amplification efficiencies of the Pfmdr1 and the Pfβ-tubulin genes measured by using ten-fold dilutions of 3D7 DNA, were similar (95% and 95%, respectively). (FIG. 6D.)

I. PfPM2 mRNA Expression Profile

One step reverse transcriptase (RT)-qPCRs were carried out using a CFX96 real-time PCR machine (Bio-Rad) in 25 μl volumes in a 96-well plate containing 2× SuperScript™ III Platinum One step qRT-PCR kit (Life Technologies, Courtaboeuf, France), 0.2 μM concentrations of each forward and reverse primers, 0.1 μM concentrations of specific probes (FAM-BHQ1) and 3 μl of DNase-treated RNA. Listing of primers, protocols and PCR amplification efficiencies are provided in the table below.

| | Primer Sequence | Sequences | Tm (° C.) | Product size (bp) |
|---|---|---|---|---|
| RT-PCR | PfPM2_RTPCR_F | 5'-GGATTCGAACCA ACTTATACTGC-3' (SEQ ID NO. 3) | 59.1 | |
| | PfPM2_RTPCR_R | 5'-AATTGGATCTACTG AACCTATTGATAA-3' (SEQ ID NO. 4) | 57.9 | 90 |
| | PfPM2_RTPCR_Probe | 5'-FAM-CAACATTTG ATGGTATCCTTGGTTT AGGATGGA-BHQ1-3' (SEQ ID NO. 6) | 71.3 | |
| | Pfserine-tRNA ligase_RTPCR_F | 5'-TGGAACAATG GTAGCTGCAC-3' (SEQ ID NO. 16) | 59.7 | |
| | Pfserine-tRNA ligase_RTPCR_R | 5'-GGCGCAATTT TTCAGGAACT-3' (SEQ ID NO. 17) | 61.5 | 92 |
| | Pfserine-tRNA ligase_RTPCR_Probe | 5'-FAM-TGTCTTCTT GAAAATTATCAAAAC GGCGAAGG-BHQ1-3' (SEQ ID NO. 18) | 71.6 | |

Amplifications were performed under the following conditions: 50° C. for 15 min, and 95° C. for 2 min, followed by 35 cycles of 95° C. for 15s, 60° C. for 30s and a final cycle at 35° C. for 30s. Fluorescence data were collected during the 60° C. annealing-extension steps.

For each run, PfPM2 and Pfserine-tRNA ligase mRNAs expression were measured in triplicate for each sample. DNase-treated RNA from 3D7 parasites (collected at trophozoite stage, 24h post-invasion) was included in each run as control. PfPM2 mRNA expression, normalized to Pfserine-tRNA ligase mRNA expression, was calculated by the $2^{-\Delta\Delta C_t}$ method, using the following formula:

$$\Delta\Delta_{Ct} = [(C_{t\ PfPM2} - C_{t\ Pfserine\text{-}tRNA\ ligase})_{sample} - (C_{t\ PfPM2} - C_{t\ Pfserine\text{-}tRNA\ ligase})_{3D7}],$$

where $C_t$ is the threshold cycle.

Figure 7:
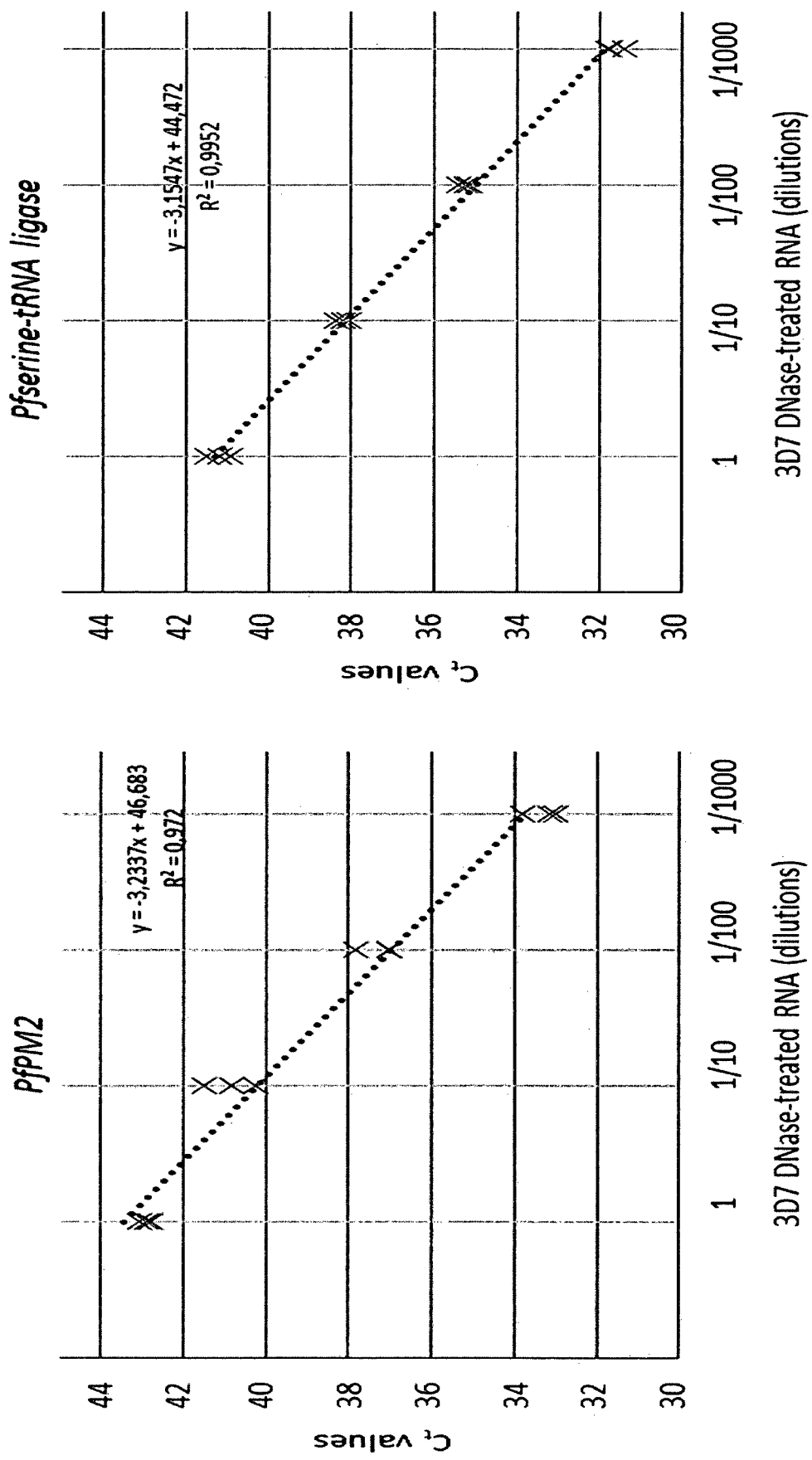
FIG. 7 shows PfPM2 mRNA expression profile, with listing of primers, protocols and RT-qPCR amplification efficiencies.
Figure 8A:
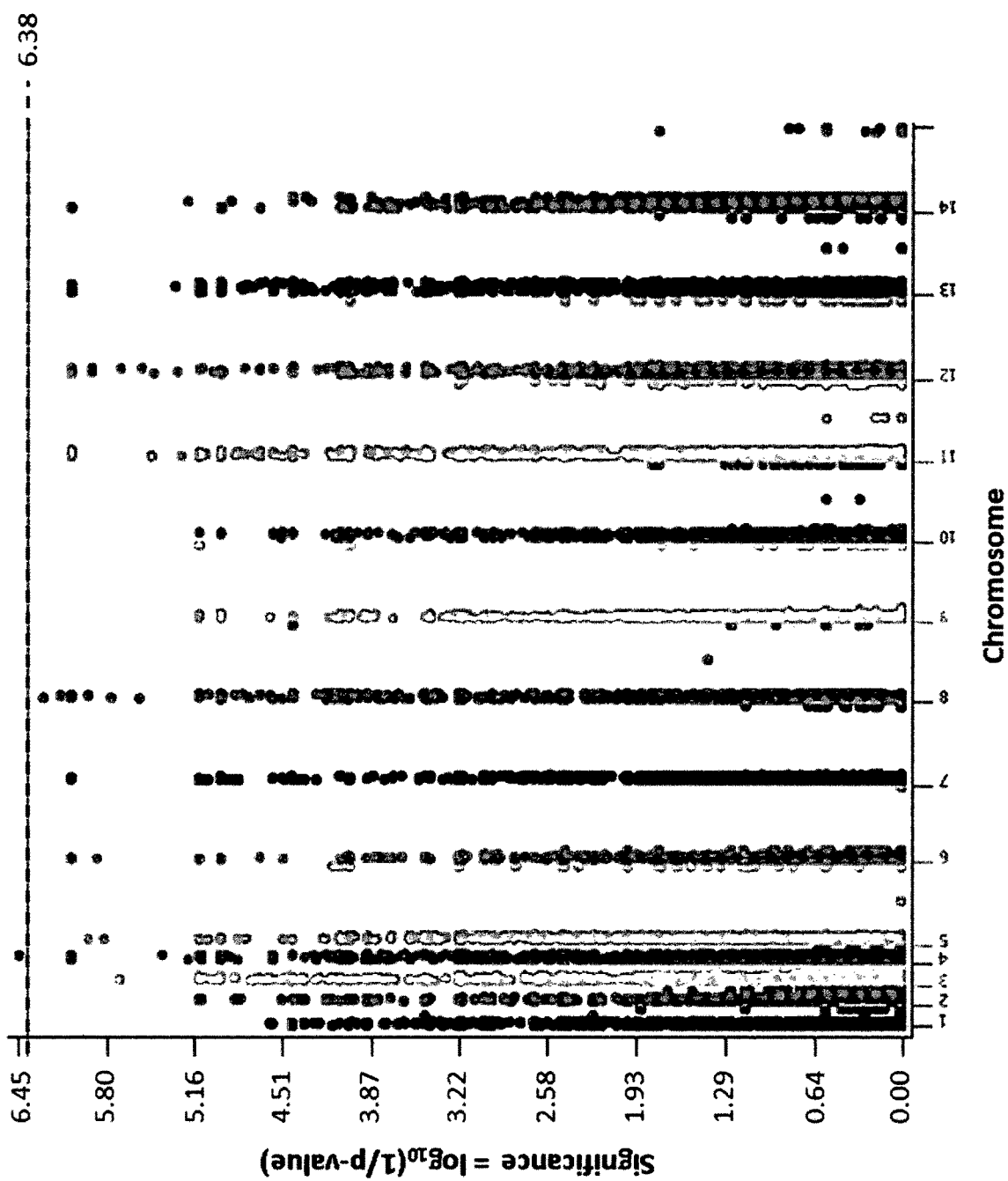
FIG. 8A shows a Manhattan plot showing the significance of single nucleotide polymorphisms (SNPs) between whole-genome exome sequences of 23 piperaquine-resistant and 8 piperaquine-sensitive culture-adapted lines phenotyped using in-vitro PSA. Each dot represents a SNP in a set of 31 culture-adapted parasites, according to chromosome. The x axis represents genomic location, and the y axis represents the $\log_{10}$ transformed Fischer exact test's p-values. After Bonferroni correction at level 5%, only 2 SNPs in 2 genes, PF3D7_0420000 (zinc finger protein, putative) (position 896588) and its neighbor PF3D7_0420100 (serine/threonine protein kinase RIO2) (position 908385) achieved genome-wide significance between the resistant and sensitive lines ($p<3.5\times10^{-7}$ for both SNP, Fisher's exact test) [$>6.38=\log_{10}(120691/0.05)$].

RT-qPCR amplification efficiencies of Pfplasmepsin2 and Pfserine-tRNA ligase, measured using ten-fold dilutions of DNase-treated 3D7 RNA, were similar (104% and 107%, respectively). (FIG. 7.)

J. Statistical Analysis

Data were analyzed with MedCalc version 12 (Mariakerke, Belgium). Kruskal-Wallis or Mann-Whitney tests were used for non-parametric comparisons and the Student's t-test or one-way analysis of variance were used for parametric comparisons. For proportions (expressed with percentages and 95% confidence intervals), chi-squared or Fisher's exact tests were performed. Manhattan plots were generated using the SNPEVG software.[15] We tested CNV for differential distribution between piperaquine-resistant and sensitive parasite lines using: 1) a parametric Student t-test for difference in means; 2) a non-parametric Wilcoxon rank-sum test. We conducted SNP-wise analysis and used the exact Fisher's exact test to identify significant SNPs differences between PPQ-resistant and -sensitive parasite lines. A Bonferroni threshold (0.05/number of SNPs or genes analyzed) was used to evaluate genome-wide significance and adjust p-values when statistical tests were performed simultaneously on a single data set (see methods section for details). Relative risks were estimated using the Mantel-Haenszel test. Relationships between a cumulative risk of failure at day 42 and molecular signatures associated with PPQ resistance were assessed by survival analysis. Curves were compared with the Mantel-Haenszel log-rank test. The Cox proportional-hazards regression model was used to evaluate association between parasite genotypes (K13 mutations, PfPM2 and Pfmdr1 copy number) and treatment responses. A linear regression analysis was used to evaluate the relationship between DHA-PPQ efficacy and the proportion of parasites with multicopy PfPM2. We deemed p-values of less than 0.05 as significant.

Example 2: Patients

Figure 1B:
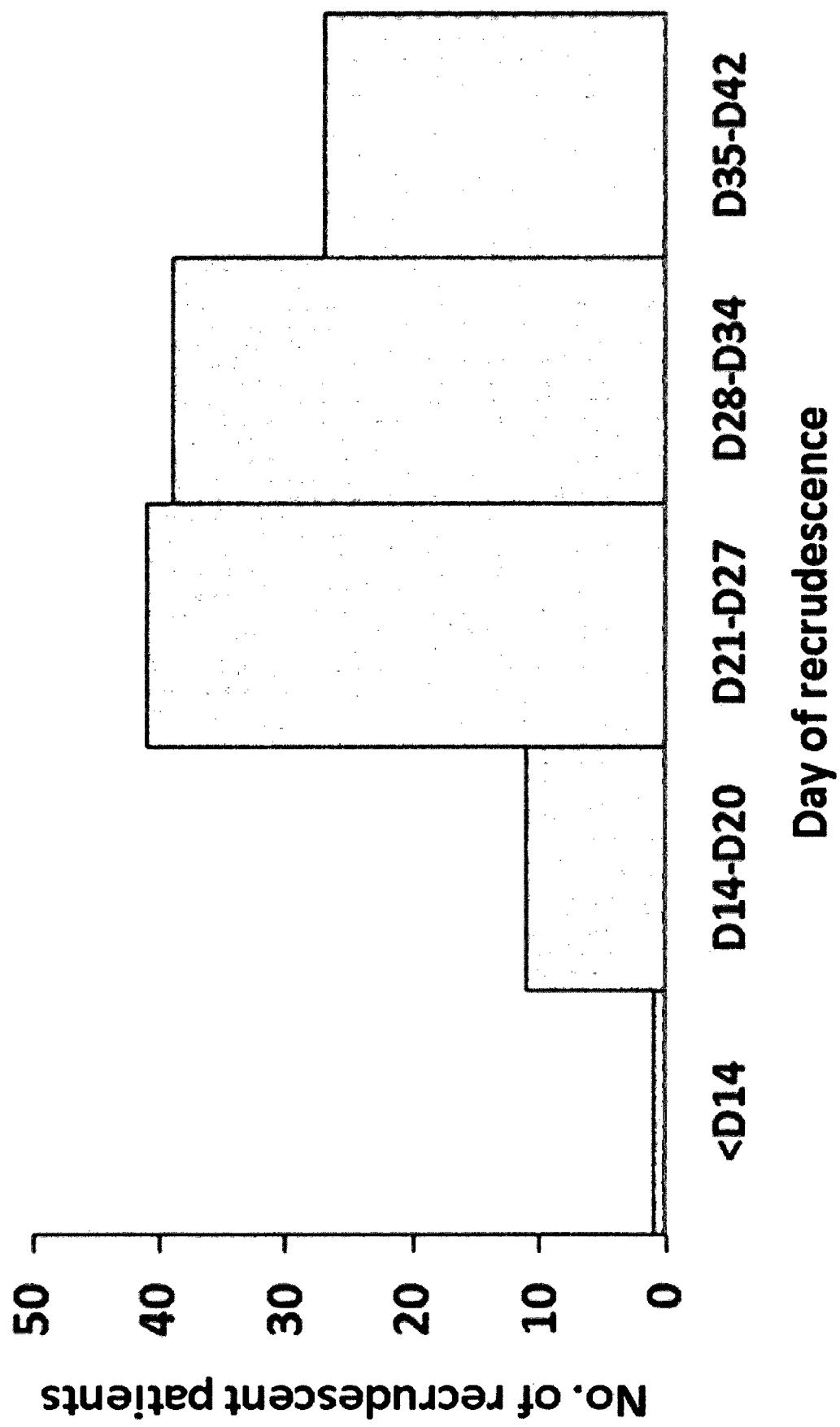
Figure 2:
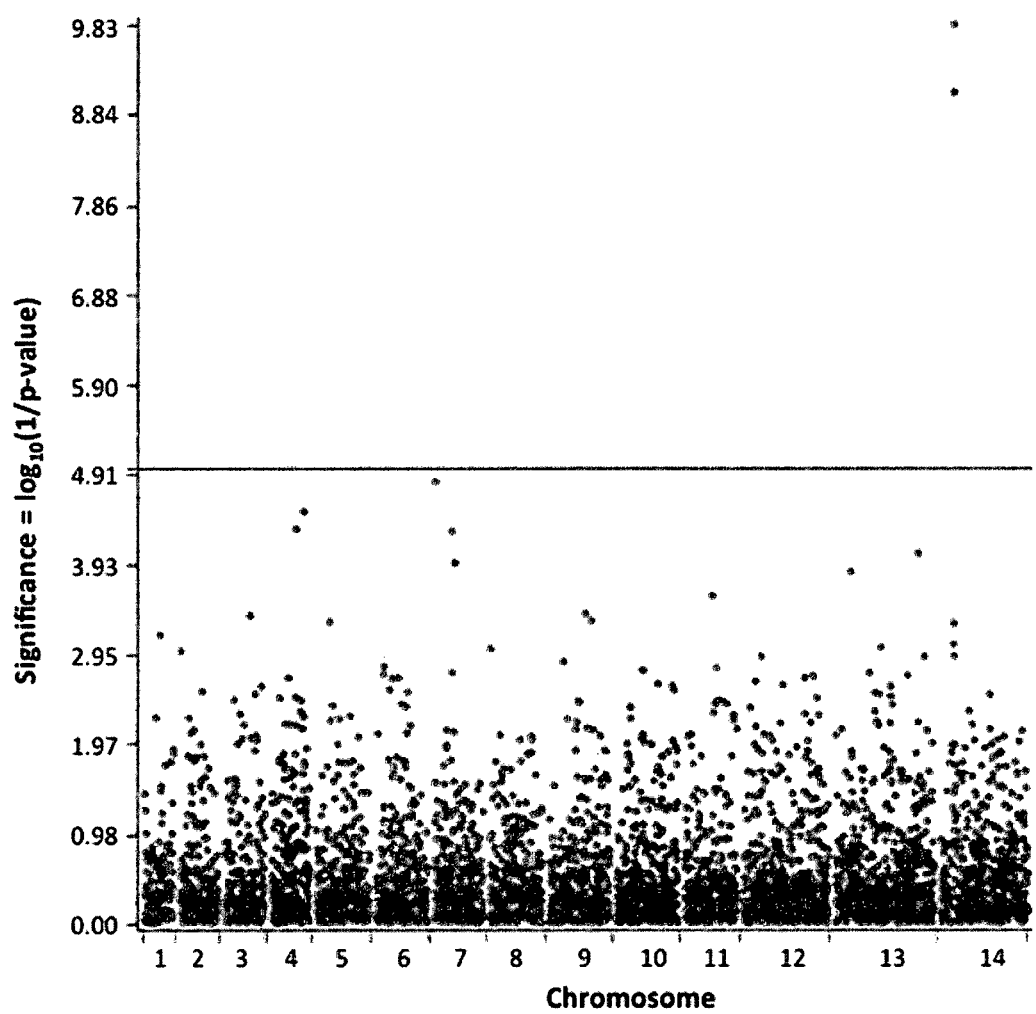
FIG. 2 shows a Manhattan plot showing the significance of copy number variations between whole-genome exome sequences of 23 PPQ-resistant and 8-sensitive culture-adapted lines collected in western Cambodia in 2012 and phenotyped using in-vitro PSA. Each dot represents a gene in the set of 31 culture-adapted parasites, according to chromosome. The x-axis represents genomic location, and the y-axis represents the $\log_{10}$ transformed Student t-test's p-values. After Bonferroni correction, only 2 genes, PF3D7_1408000 (plasmepsin2) and PF3D7_1408100 (plasmepsin3) achieved genome-wide significance (>4.97=log 10 (4616/0.05.
Figure 3:
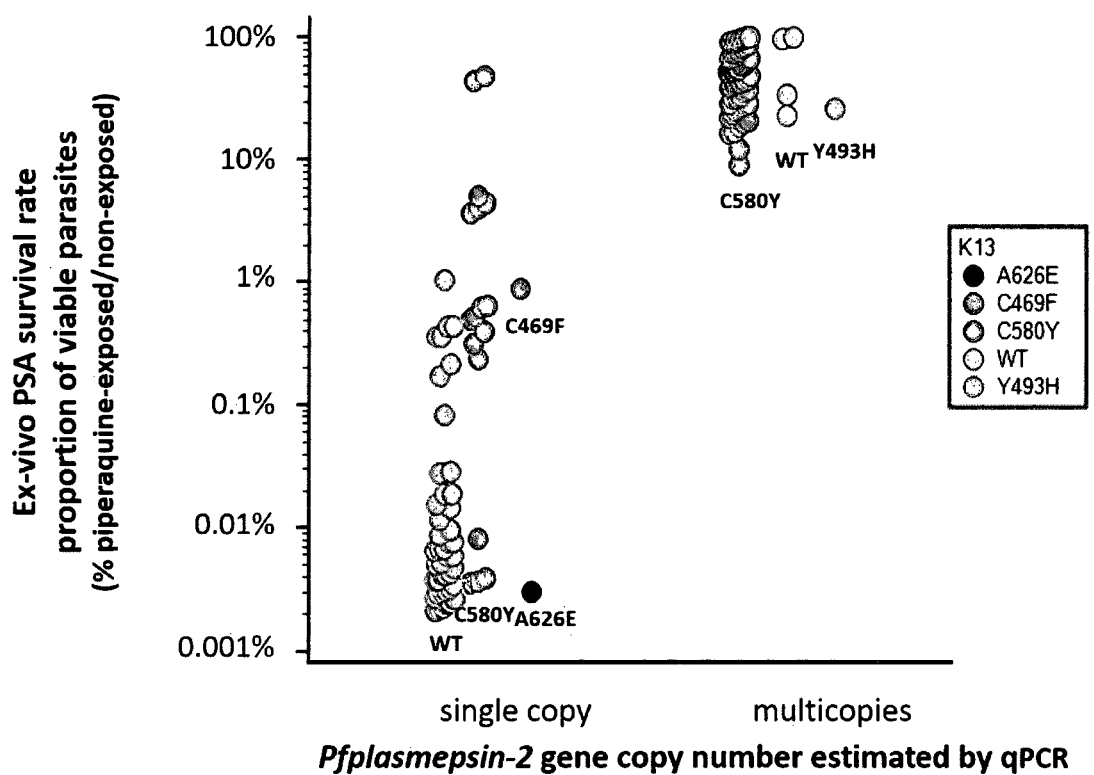
FIG. 3 shows ex-vivo PSA survival rates and single (n=67) and multicopy PfPM2 (n=67) as estimated by qPCR in isolates collected before DHA-PPQ treatment stratified by K13 genotype. Patients were enrolled in clinical studies conducted in 2014-2015 in Mondulkiri, Rattanakiri, Siem Reap and Stung Treng provinces, stratified by K13 genotypes. K13 polymorphisms were detected in 65/69 PPQ-resistant (64 C580Y, 1 Y493H) and 17/65 PPQ-susceptible isolates (15 C580Y, 1 C469F and 1 A626E). Three parasite lines with discordant data were observed: two resistant lines with non-amplified PfPM2 and PfPM3 loci (6246 and 6395) and one sensitive line with 2 PfPM2 copies (6369, DNA expansion type 1) (see Table 2).

From 2009-2015, 725 patients were enrolled in clinical studies to assess the efficacy of the 3-day DHA-PPQ treatment. By 2015, the cumulative proportion of *P. falciparum* recrudescence at day 42 after PCR correction was 16.4% (119/725), ranging from 0 to 62.5% depending on the site and the year of study (Table 1, FIG. 1).

Example 3: Molecular Signatures Associated with PPQ-Resistance

Whole-genome sequences were obtained from 31 ART-resistant (K13 C580Y) culture-adapted parasite lines collected in western Cambodia in 2012, including 23 PPQ-resistant and 8 PPQ-sensitive lines as defined by their in-vitro PSA survival rates (Table_2). We observed a total of 120,691 exomic (coding sequence) SNPs. After Bonferroni correction, genome-wide association analyses identified significant differences between resistant and sensitive lines at two genes: one being a SNP in the PF3D7_0420000 gene (encoding a putative zinc finger protein) ($p<3.5\times10^{-7}$, Fisher's exact test) and the other being a SNP in the PF3D7_0420100 gene (encoding a Rio2 serine/threonine protein kinase) ($p<3.5\times10^{-7}$, Fisher's exact test). However, the sequences of both genes showed numerous ambiguous positions with variable proportions of wild type and mutant nucleotides, precluding identification of specific resistance-associated alleles (FIGS. 8A, 8B1-6, and 8C1-2). It was unclear whether this heterogeneity reflected purifying selection affecting these adjacent genes or selection of a nearby locus (that we were unable to identify) and whether such selection was associated with PPQ resistance or loss of mefloquine resistance.

In contrast, strong signals of gene amplification were detected in the PPQ-resistant group in a region located on chromosome 14 that encodes hemoglobin-digesting proteases known as plasmepsins (PfPMs) ($p<10-9$, Student t-test with Bonferroni correction Figure_2). All sequences in piperaquine-resistant and -sensitive lines showed a Q442H PfPM2 polymorphism (at the nucleotide level g1326c), whereas all PfPM3 sequences were wild-type. Of note, Q442H PfPM2 polymorphism is frequently observed in reference laboratory lines (such as Dd2, GB4, and HB3) or wild isolates (obtained from PlasmoDB). The correlation between in-vitro PSA survival rates and PfPM2 PfPM3 copy number was highly significant (r=0.83 [95% Confidence Interval (CI) 0.67-0.91], p<0.0001 and r=0.85 [95% CI 0.71-0.93], p<0.0001). We observed four different profiles of DNA expansion (See FIGS. 9A-9E).

We used the PlasmoCNVScan software to evaluate gene copy number variation in piperaquine-resistant and -sensitive parasite lines. Sequences of genes encoding PfPM1-4 are quite different from each other but to confirm accurately PfPM2 and PfPM3 gene amplification, we identified for each gene, a 30 base specific nucleotide sequence: tgaatcagctgtgaatagctcacatttaa (SEQ ID NO.19) for PfPM1; caattcaacatttgatggattaaacattga (SEQ ID NO.20) for PfPM2; tgaagaatcctttaacacgtttegagtaac (SEQ ID NO.21) for PfPM3 and tgcttcagcatttgatcgattgaaattagg (SEQ ID NO.22) for PfPM4. We then counted the number of occurrences of these sequences in the 31 whole-genome sequences and standardized the number of occurrences of each specific PfPM sequence by normalizing against the mean of Pfβtubulin specific sequences (tgatgtgegcaagtgatcc (SEQ ID NO.7) and tcctttgtggacattcttcctc (SEQ ID NO.8)). We confirmed the specificity of the amplifications observed with PlasmoCNVScan and the four types of DNA expansion. Each type of DNA expansion presents a specific signature in the WDM package (see below). Based on our data set, we are not able to differentiate between multiple emergence events that gave rise to the four DNA expansion types and a single event corresponding to type 4, which was followed by distinct losses of gene amplifications in the other expansion types.

Figure 9B:
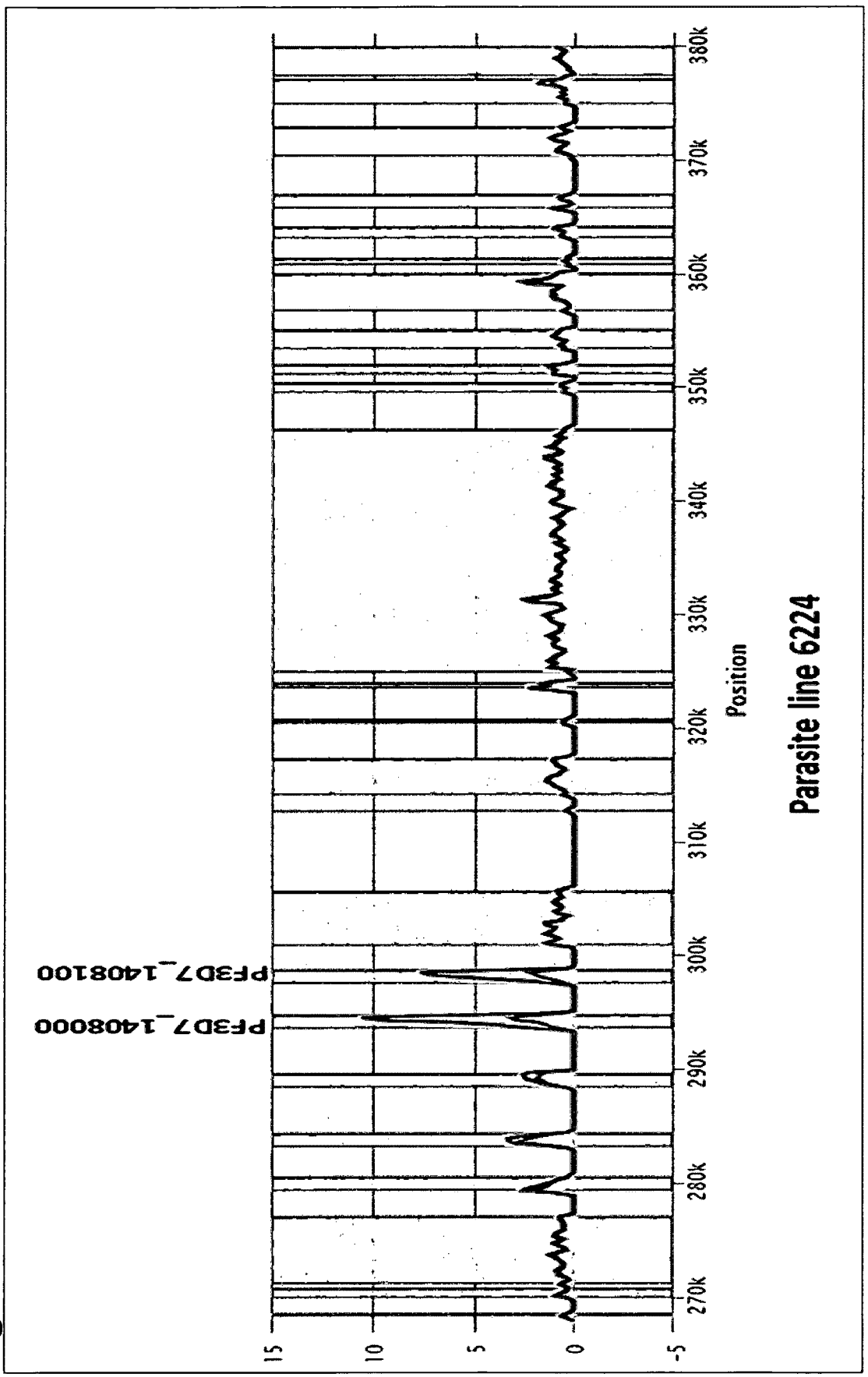
Figure 9C:
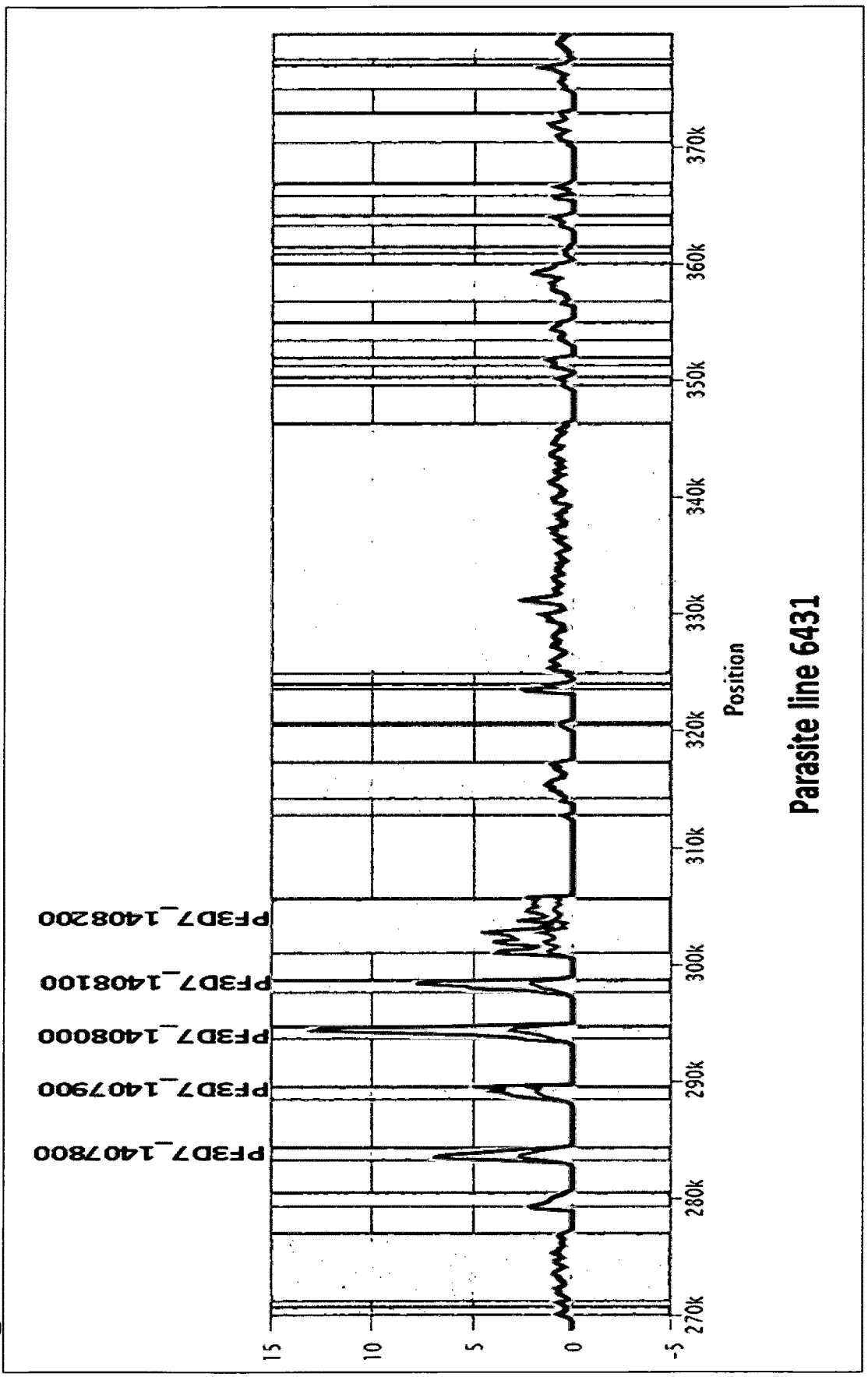
Figure 9D:
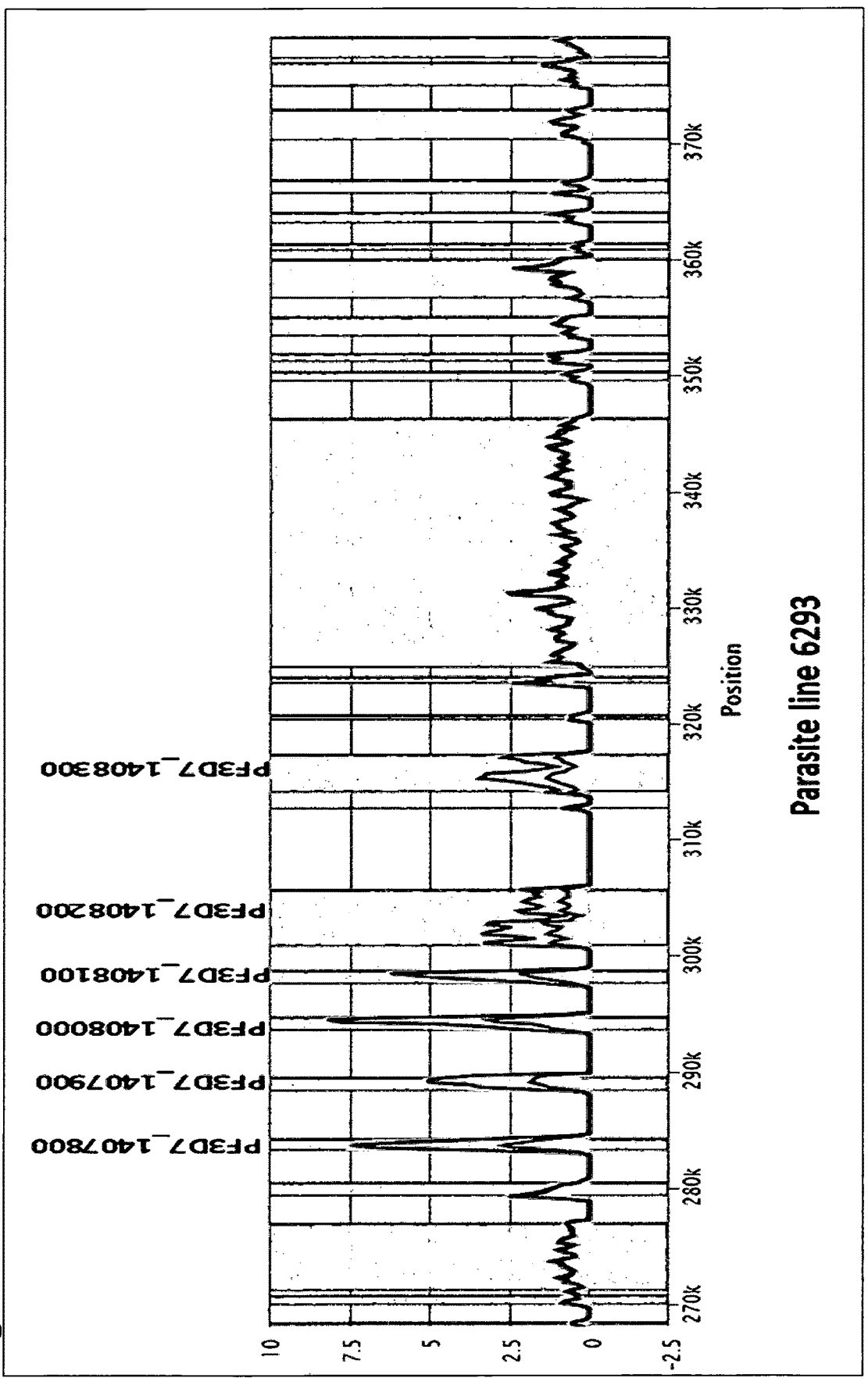
Figure 9E:
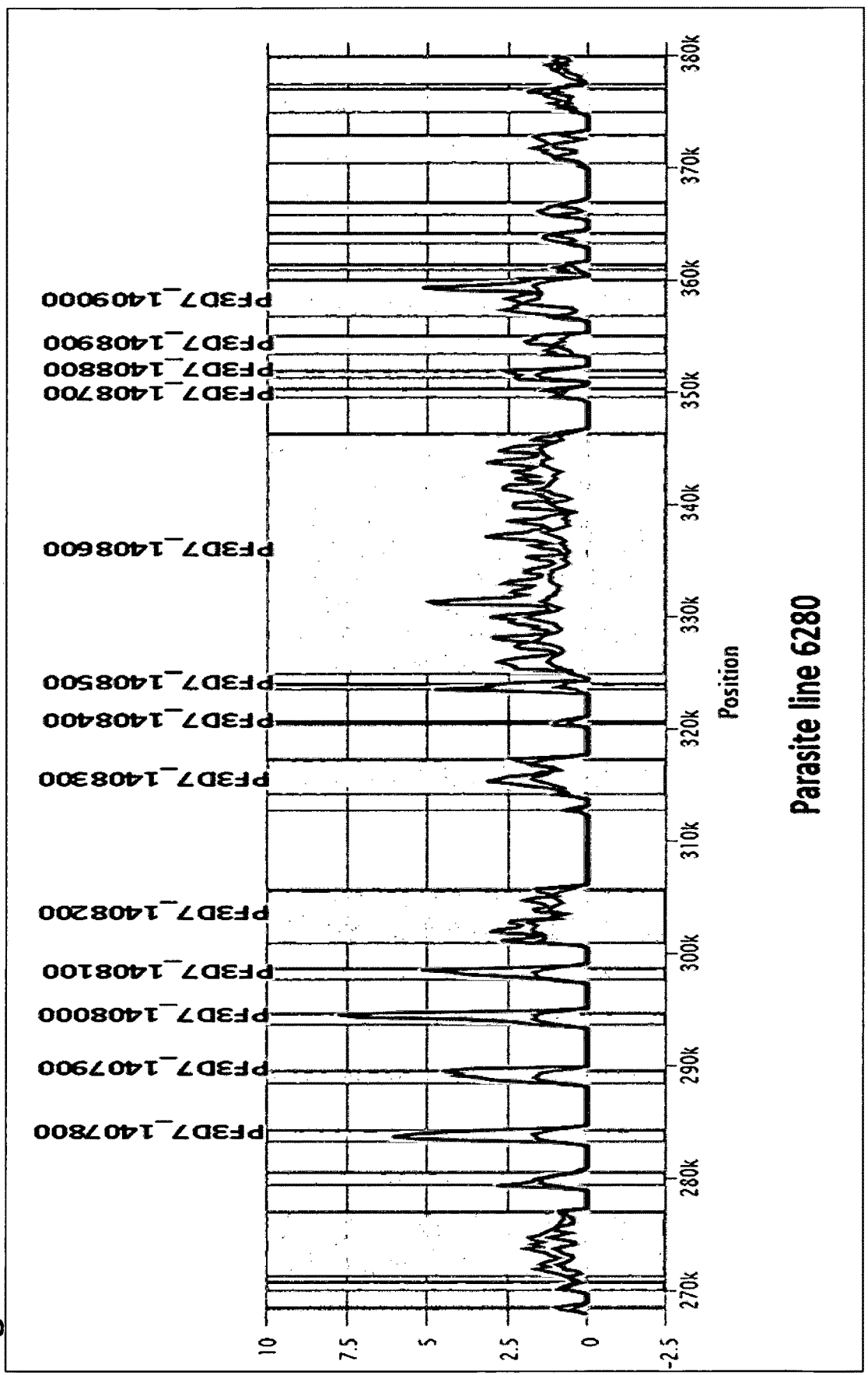

The specific signature of each type of DNA expansion observed with the WDM package is shown in FIGS. 9B-9E. (the x-axis represents the gene position, and the y-axis represents the ratio between observed coverage and theoretical coverage for each gene/position giving an estimated copy number variation for each region). DNA expansion type 1 (approx. 10 kb-long segment amplified) was the most frequent (13/22), and included PfPM2 and PfPM3 genes. Specific signature of the parasite line ID 6224 is given as example (see Table 2 for details). (FIG. 9B.) DNA expansion type 2 (6/22), approx. 18 kb-long, included the upstream PfPM4 and the downstream AP2-G2 genes. Specific signature of the parasite line ID 6224 is given as example (see Table 2 for details). (FIG. 9C.) DNA expansion type 3 (observed once) 26 kb-long, included an additional downstream gene. Specific signature of the parasite line ID 6293 is given as example (see Table 2 for details). (FIG. 9D.) DNA expansion type 4 (observed in two samples) spanned 72 kb from PfPM-4 and extending downstream up to a WD-repeat containing protein. Specific signature of the parasite line ID 6280 is given as example (see Table 2 for details). (FIG. 9E.)

In-vitro PSA survival rates were significantly higher in parasites harboring DNA expansion type 2 (N=6, PSA mean value=64.9%, SD=7.7%) compared to those harboring DNA expansion type 1 (N=13, PSA mean value=44.8%, SD=16.1%, p=0.0103) or type 4 (N=2, PSA mean value=16.2%, SD=16.2%, p=0.0206, two-sample t tests with equal variances). Only one sequence had the DNA expansion type 3 (PSA mean value=39.3%).

Figure 10:
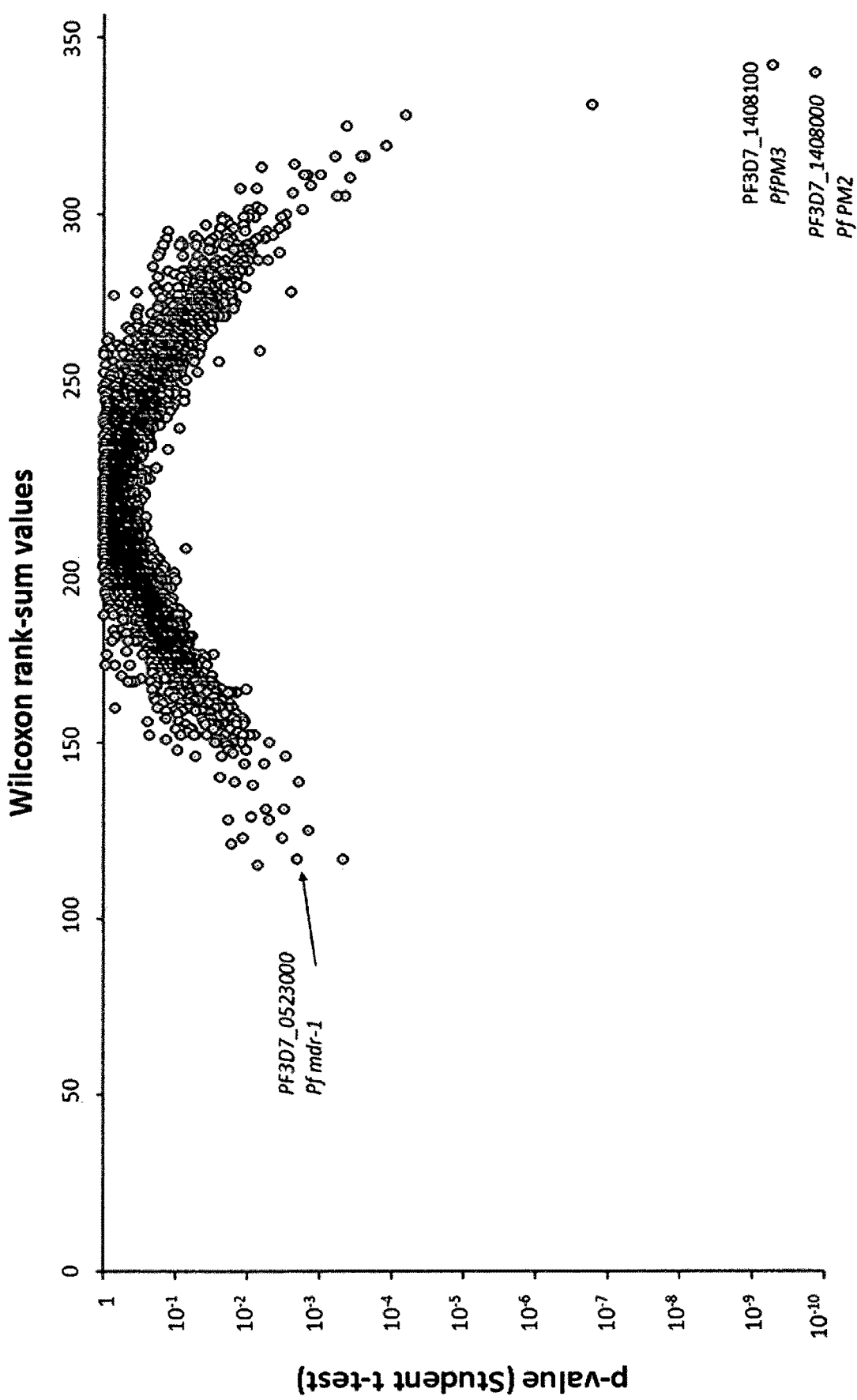
FIG. 10 shows distribution of the Wilcoxon Rank-Sum test p-values ranking the significance of CNVs of the 4,616 genes screened between whole-genome exome sequences of 23 piperaquine-resistant and 8 piperaquine-sensitive culture-adapted lines phenotyped using in-vitro PSA. Each dot represents a CNV. The x-axis represents the Wilcoxon rank-sum values, and the y-axis represents the p-values (Student t-test). PF3D7_1408000 (PfPM2) and PF3D7_1408100 (PfPM3) ranked in the first and second positions ($p=5.4\times10^{-10}$ and $p=1.4\times10^{-10}$, respectively). PF3D7_0523000 (Pfmdr1) was classified at the 4676th/4678 position ($p=0.007$).

Using the Wilcoxon rank-sum two-sided test, PfPM2 PfPM3 copy numbers were confirmed to be significantly increased in resistant lines (p<10-5). Conversely, a cluster of 5 genes on chromosome 5 (PF3D7_0531700, PF3D7_0522900, PF3D7_0523000, PF3D7_0523100, PF3D7_0523200), which included Pfmdr1, presented increased copy numbers in sensitive lines. Pfmdr1 was amplified in 5 of 8 PPQ-sensitive lines but 0 of 23 PPQ-resistant lines (p=0.007) (FIG. 10).

Example 4: PfPM2 CNV and Ex-Vivo PPQ Susceptibility

To examine associations between PfPM CNV and ex-vivo PSA survival rate, we focused on PfPM2, used as an amplicon reporter. First, we optimized a qPCR method to assess PfPM2 gene copy number (See FIGS. 6A-6D).

PfPM2 copy number detected by qPCR was 100% concordant with the whole-genome sequencing estimates for the 31 culture-adapted parasites (p<0.0001, Fisher test). From a set of 134 isolates with known ex-vivo PSA profiles, PfPM2 was amplified in 67 of 69 PPQ-resistant parasites (50, 15 and 2 isolates with 2, 3 or 4 PfPM2 copies, respectively), and 0 of 65 PPQ-susceptible parasites (Figure_3). The median ex-vivo PSA survival rate was significantly higher in isolates with ≥2 PfPM2 copies compared to those with unamplified (single copy) PfPM2 (51.7% [IQR 29.7-75.1%] vs. 0.004% [IQR 0.003-0.39%], p<0.0001, Mann-Whitney test). An increased PfPM2 copy number predicted ex-vivo PPQ resistance with a sensitivity of 0.97 (95% CI 0.90-0.99 and specificity of 1.0 (95% CI 0.65-1). K13 polymorphisms were detected in 65 PPQ-resistant and 17 PPQ-susceptible isolates (Figure_3). Only 4 of 69 PPQ-resistant isolates harbored a wild-type K13 sequence. In a multiple regression analysis, increased PfPM2 copy number was more strongly associated than K13 mutations with in-vitro PPQ resistance ($r_{partial}$=0.94, p<0.0001 and $r_{partial}$=0.25, p=0.004, respectively).

Example 5: mRNA and Protein Levels in Single and Multicopy PfPM2 Parasites

Figure 11A:
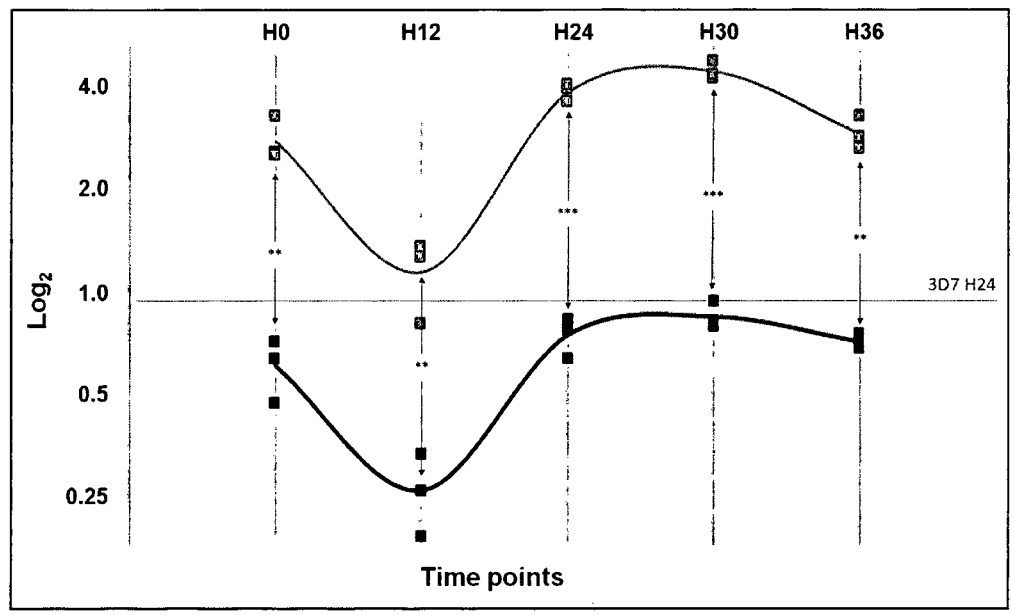
FIG. 11A shows PfPM2 mRNA transcript levels, relative to Pfserine-tRNA ligase mRNA in early ring stages (H0: 0-3h post invasion), late ring stages (H12: 12-15 h post invasion), early trophozoite stages (H24: 24-27h post invasion) and mature trophozoites (H36: 36-39h post invasion) of the in-vitro culture-adapted piperaquine-resistant ID_6320 line (PSA survival rate=62.1%, 2 copies PfPM2, C580Y K13 allele, solid grey line) and piperaquine-sensitive ID_6267 line (PSA survival rate=0.5%, single copy PfPM2, C580Y K13 allele, solid black line) (see table 2 for details). The x axis represents different time points post invasion, and the y axis represents log 2 transformed $2^{-\Delta\Delta C t}$ values (see methods section for details). The horizontal solid line corresponds to the PfPM2 mRNA level of 3D7 trophozoites (24h post invasion), used as a control. Black arrows indicate significant differences in PfPM2 mRNA level (* $p<0.05$-0.011,  $p<0.01$-0.0011 and * $p<0.001$) between the 2 strains at each time point.
Figure 11B:
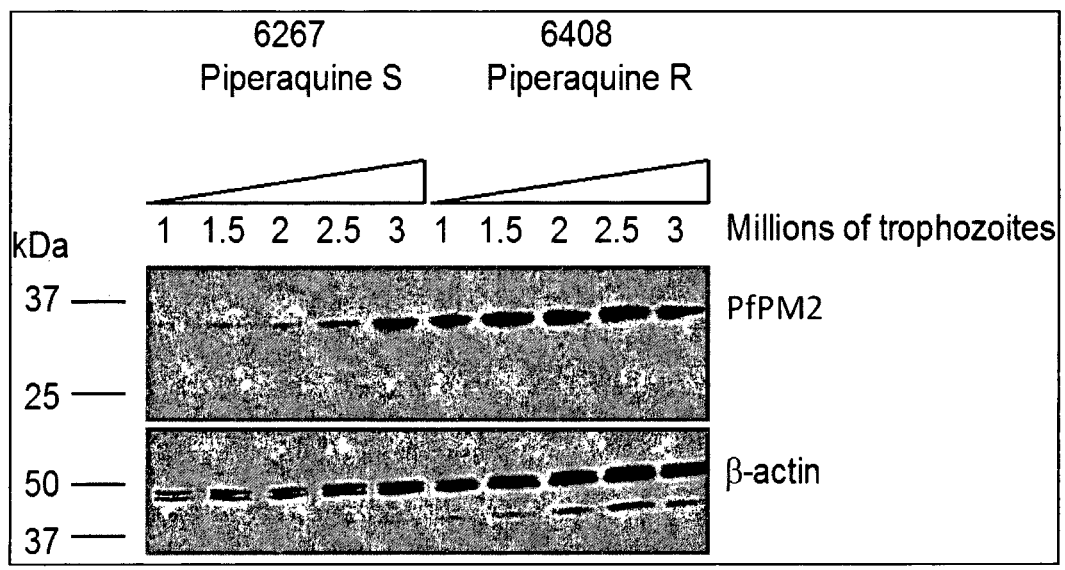
FIG. 11B shows PfPM2 expression in *Plasmodium falciparum* synchronized trophozoite-stage of piperaquine-resistant (6408, PSA survival rate=58.7%, multicopy PfPM2) and piperaquine-sensitive parasite lines (6267, PSA survival rate=0.5%, single copy PfPM2) detected by western immunoblot. The piperaquine-resistant parasite line 6408 has higher PfPM2 protein levels than the sensitive line 6267. Synchronized trophozoite-stage cultures (24-30 hours post invasion) were probed with anti-PfPM2 (gift of Daniel Goldberg) and anti-beta-actin (NovusBio) antibodies. The resistant line has approximately twice as much PfPM2 as the sensitive line.

PfPM2 transcript levels were 4.1- to 5.3-fold higher in the PPQ-resistant line (ID_6320) as compared to the PPQ-sensitive line (ID_6267) at all time points of the intra-erythrocytic cycle investigated. PfPM2 protein levels were at least two-fold higher in PPQ-resistant parasites (ID_6408) compared to the sensitive line (ID_6267) (FIG. 11). However, further work is required to expand this analysis to further lines.

Example 6: PfPM2 CNV and DHA-PPQ Treatment Outcome

We next explored the relationship between PfPM2 CNV and DHA-PPQ treatment outcome in the isolates from 725 patients collected before DHA-PPQ treatment, of whom 119 experienced a recrudescence between day 12 and day 42 (Figure_1). PfPM2 was unamplified, 2-copy or ≥3-copy in 476/725 (65.7%), 153/725 (21.1%) or 96/725 (13.2%) isolates, respectively. Only 7 of 476 patients (1.5%) with unamplified PfPM2 parasites had recrudesced by day 42 compared with 112/249 (45.0%) patients infected with multicopy PfPM2 parasites (RR=22.8 [95% CI: 10.7-48.6]; p<0.0001). Recrudescence was more frequent for isolates with ≥3 compared with 2 PfPM2 copies (52/96, 54.2% vs. 60/153, 39.2%, p=0.02).

The cumulative incidence of DHA-PPQ treatment failure increased with increasing PfPM2 gene copies: unamplified vs. 2 copies (HR=32.2 [95% CI: 17.9-58.0], p<0.0001), unamplified vs. 3 copies (HR=49.0 [95% CI: 23.0-104.2], p<0.0001), or 2 copies vs. ≥3 copies (HR=1.53 [95% CI: 1.04-2.25], p=0.02) (Figure_4A). The mean time to recrudescence decreased with increasing PfPM2 copy number:

41.9 days (95% CI: 41.8-42.0) for patients with unamplified PfPM2, 36.0 days (95% CI: 34.6-37.4) for those with 2 copies, or 34.0 days (95% CI: 32.1-35.9) for those with >3 copies. An increased PfPM2 copy number predicted DHA-PPQ treatment failures with a sensitivity of 0.94 (95% CI: 0.88-0.98) and a specificity of 0.77 (95% CI: 0.74-0.81). The AUC (area under the ROC curve) was 0.86 (95% CI 0.83-0.88), significantly different from 0.5 (p<0.0001).

Example 7: K13 Propeller Polymorphism and Pfmdr1 Gene Amplification

Figure 4B:
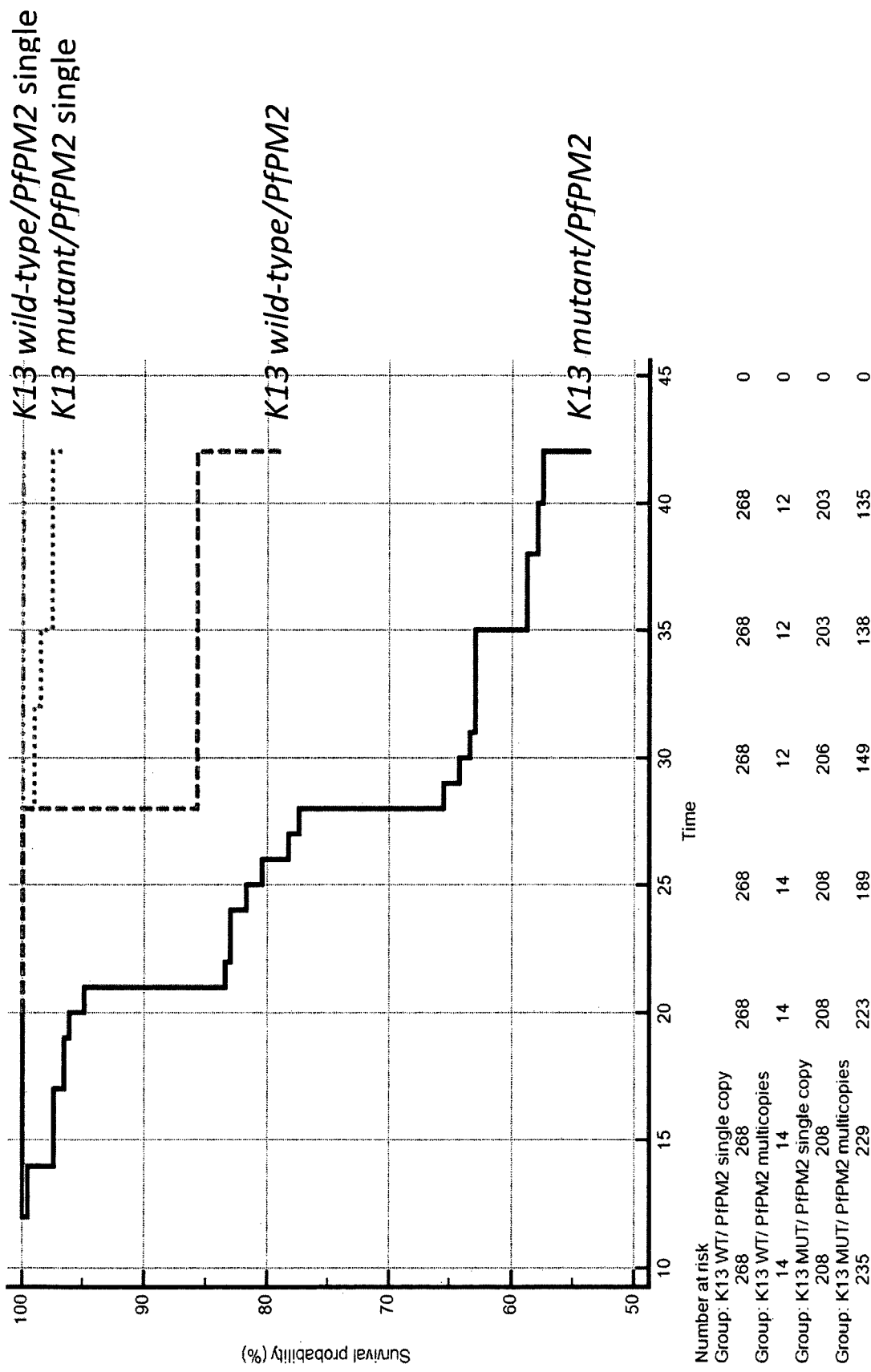

Among the 725 patients treated with DHA-PPQ, K13 mutants were detected in 443/725 (61.1%) day 0 isolates (FIG. 4B). Of these, 116/443 (26.2%) were from patients who failed DHA-PPQ treatment by day 42 compared to 3 of 282 (1.1%) from patients harboring K13 wild-type parasites (RR=24.6 [95% CI: 7.9-76.7], p<0.0001). A single Pfmdr1 gene copy was detected in 610/725 (84.1%) day 0 isolates. DHA-PPQ failures were observed in 112/610 patients (18.4%) infected with parasites harboring a single Pfmdr1 copy and 7/115 (6.1%) of patients infected with multicopy Pfmdr1 parasites (RR=3.0 [95% CI: 1.4-6.3]; p=0.003). We observed that the cumulative incidence of DHA-PPQ treatment failure did not increase with increasing age (stratified in 3 classes: 0-15, 16-30 and >30 years old, p=0.1809, Logrank test) or with increasing parasitemia measured in isolates collected before DHA-PPQ treatment (stratified in 4 classes: <5000, 5001-20000, 20001-50000 and >50000 parasites per µl, p=0.4612, Logrank test).

After controlling for K13 and Pfmdr1 genotypes in a Cox proportional-hazards regression model, PfPM2 copy number (any increase compared to non-amplification) was the most significant molecular signature associated with DHA-PPQ treatment failure (AHR=20.4 [95% CI: 9.1-45.5], p<0.0010) followed by K13 mutation (AHR=5.5 [95% CI: 1.7-18.3], p=0.005) and Pfmdr1 single copy (AHR=2.05 [95% CI: 0.95-4.42], p=0.06). The cumulative incidence of DHA-PPQ treatment failure among patients harboring ART-resistant parasites (K13-mutant) increased significantly with PfPM2 copy number: unamplified (3.3%, 7/208) vs. ≥2 copies (46.4% 109/235; HR=17.5 [95% CI: 12.2-25.2]).

Example 8: Spatio-Temporal Trends in DHA-PPQ Efficacy in Cambodia

Figure 12:
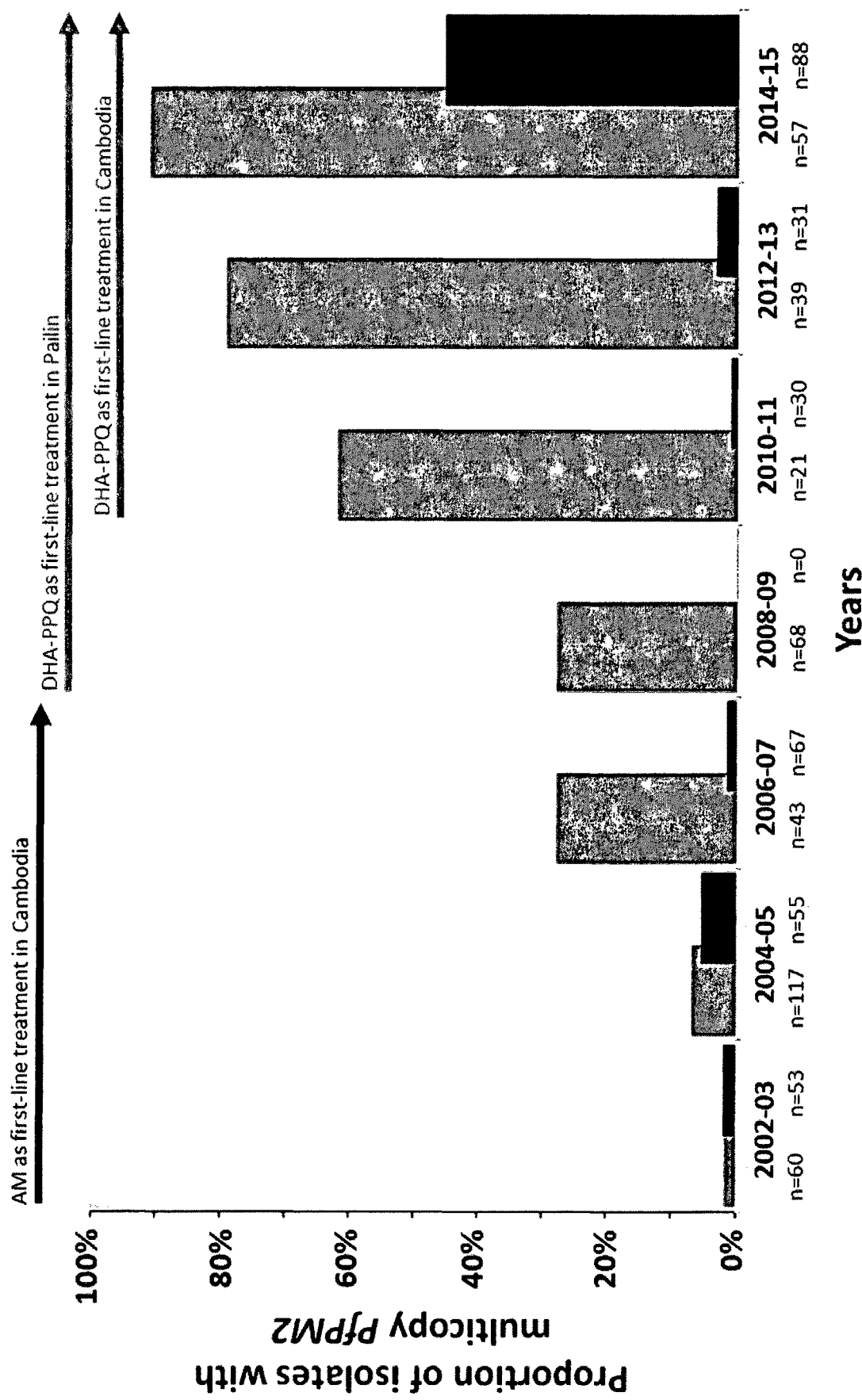
FIG. 12 shows spatio-temporal increase in frequency of parasites with multicopy PfPM2 in western Cambodia (grey histogram) and eastern Cambodia (black histogram) between 2002 and 2015. On the x-axis, sample sizes are given by site and year.

PfPM2 CNVs were investigated in samples collected in western (N=405) and eastern (N=324) provinces from 2002 to 2015 (i.e., before and after the introduction of DHA-PPQ). The proportion of multicopy PfPM2 parasites increased from 27.9% (19/68) in 2008-2009 to 91.2% (52/57) in 2014-2015 in western provinces. In eastern provinces, multicopy PfPM2 parasites were infrequent until 2012-13 (3.2%, 1/31) but increased to 45.5% (40/88) in 2014-2015 (FIG. 12).

Figure 13:
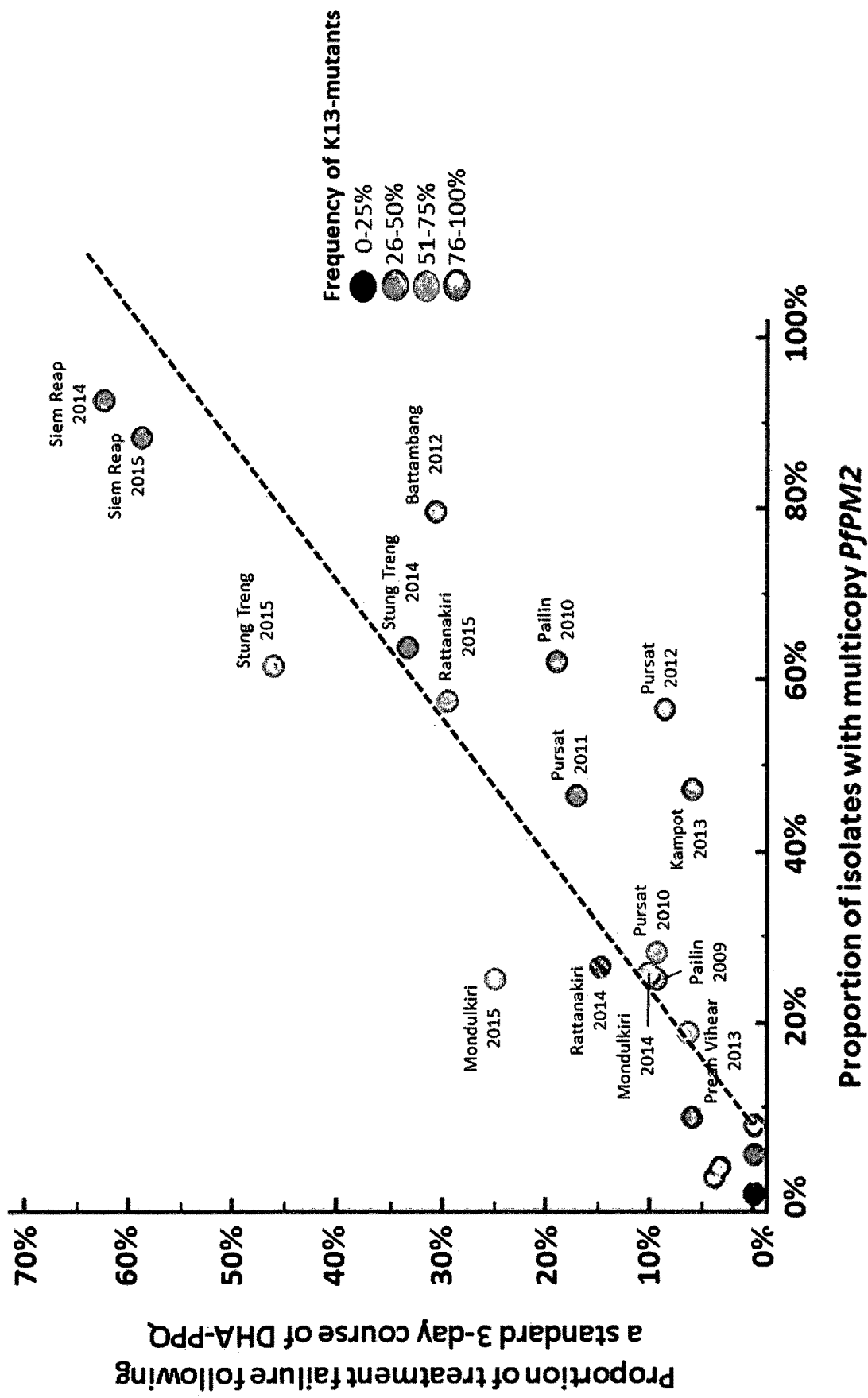
FIG. 13 shows correlation between the proportion of parasites with multicopy PfPM2 and DHA-PPQ treatment failure rates recorded in 12 sites across Cambodia from 2009 to 2015. Results from each clinical study (site and year) are represented by a colored dot. The position of the dot corresponds to the proportion of parasites with multicopy PfPM2 (x axis) and the DHA-PPQ treatment failure rate (y axis). The grey gradient code refers to the proportion of K13 mutant parasites in each site by year.

The association between the proportion of multicopy PfPM2 parasites and DHA-PPQ treatment failure rates was explored in the 12 sites where DHA-PPQ efficacy studies were conducted in 2009-2015. The proportion of multicopy PfPM2 isolates was negatively correlated with day 42 cure rates (r=0.89 [95% CI: 0.77-0.95]; p<0.0001) (FIG. 13). A linear regression model showed that DHA-PPQ clinical efficacy at day 42 fell below 90% when the proportion of multicopy PfPM2 parasites on K13-mutant genetic background rose above 22%.

Example 9: Discussion

Following reports of increasing failure of artesunate-mefloquine in western Cambodia, DHA-PPQ was adopted in 2008. Resistance to this combination has recently accelerated to levels that render it widely ineffective.[1] The dearth of alternatives creates a perilous situation whereby these multidrug-resistant infections might become untreatable and spread to other malaria-endemic regions.

The strategy used by the inventors to search for genetic associations with PPQ resistance relied on genome-wide sequence comparisons of ART-resistant parasite lines presenting in-vitro PSA survival rates indicative of PPQ resistance or susceptibility. Results identified amplification of the PfPM2-3 cluster as the most significant molecular event associated with PPQ resistance. To confirm this association, the inventors focused on PfPM2, located in the center of the amplicon and presenting the highest statistical association (FIGS. 9 and 10). PfPM2 amplification strongly correlated with ex-vivo PSA survival rates irrespective of ART susceptibility and was highly predictive of DHA-PPQ failures. PfPM2 amplification thus represents the first, robust informative marker for PPQ resistance.

Figure 14A:
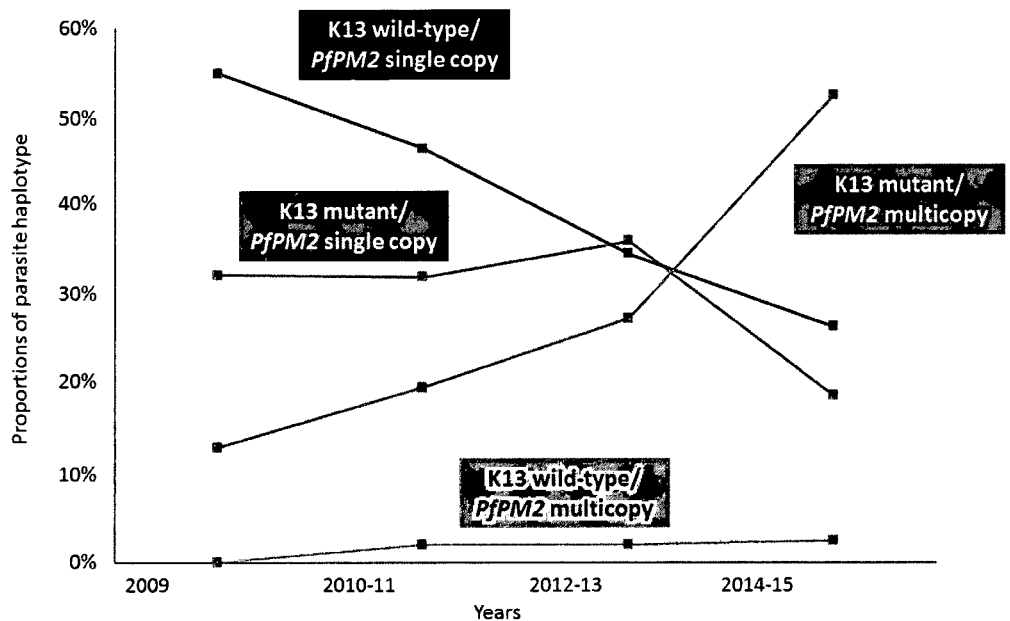
FIGS. 14A and 14B show proportions of isolates with different genetic background (K13 wild-type/PfPM2 single copy, K13 mutant/PfPM2 single copy, K13 mutant/PfPM2 multicopy and K13 wild-type/PfPM2 multicopy). (A) Over-time trends of the proportions of isolates with different genetic background (K13 wild-type/PfPM2 single copy, K13 mutant/PfPM2 single copy, K13 mutant/PfPM2 multicopy and K13 wild-type/PfPM2 multicopy) observed in Cambodia from 2009 to 2015. (B) Proposed scenario of the stepwise selection process for the emergence DHA-PPQ resistant parasites in Cambodia. The thickness of the arrow is proportional to the probability of the selection process.
Figure 14B:
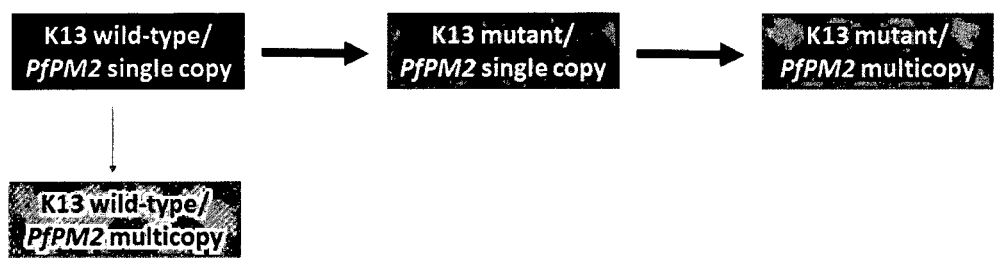

The strong association between K13 polymorphisms and PfPM2 amplification in the Cambodian parasites studied herein most likely reflects the history of drug selection in Cambodia. The proportion of isolates with different K13-PfPM2 combinations (FIG. 14) is consistent with a stepwise selection for ART resistance followed by PPQ resistance. This is in line with the delayed appearance of multicopy PfPM2 parasites in eastern provinces where the emergence of ART resistance was delayed compared to western provinces. Most (94.1%, 112/119) DHA-PPQ failures had a single gene copy of Pfmdr1, confirming earlier reports of DHA-PPQ failure cases.[6-9] The presence of single copy Pfmdr1 is consistent with data reported for in vitro-selected PPQ-resistant Dd2 parasites[16] and analysis of field samples from Cambodia, suggesting opposing resistance mechanisms against these molecules.[17] The inventors did not observe the Pfcrt C101F mutation observed in a PPQ-pressured parasite line selected in-vitro. Thus, the present data show that although the informative marker for PPQ-resistance is PfPM2 copy number, mutation of K13 alongside a single Pfmdr1 gene copy contribute to the DHA-PPQ failure phenotype.

Drug-selected gene amplification is a well-known phenomenon in malaria parasites.[18-21] The size of the amplicons on chromosome 14 varied depending on the isolate, as reported for Pfmdr1.[22] Gene amplification, which is more frequent than point mutation in *P. falciparum* parasites[22] is consistent with the remarkably rapid rise and spread of PPQ-resistance in Cambodia. Conversely, Pfmdr1 de-amplification, consistent with regained susceptibility to mefloquine, occurred in Cambodia in the recent years,[6,8,23] and as shown here is associated with the emergence of PPQ-resistant strains.

Figure 15A:
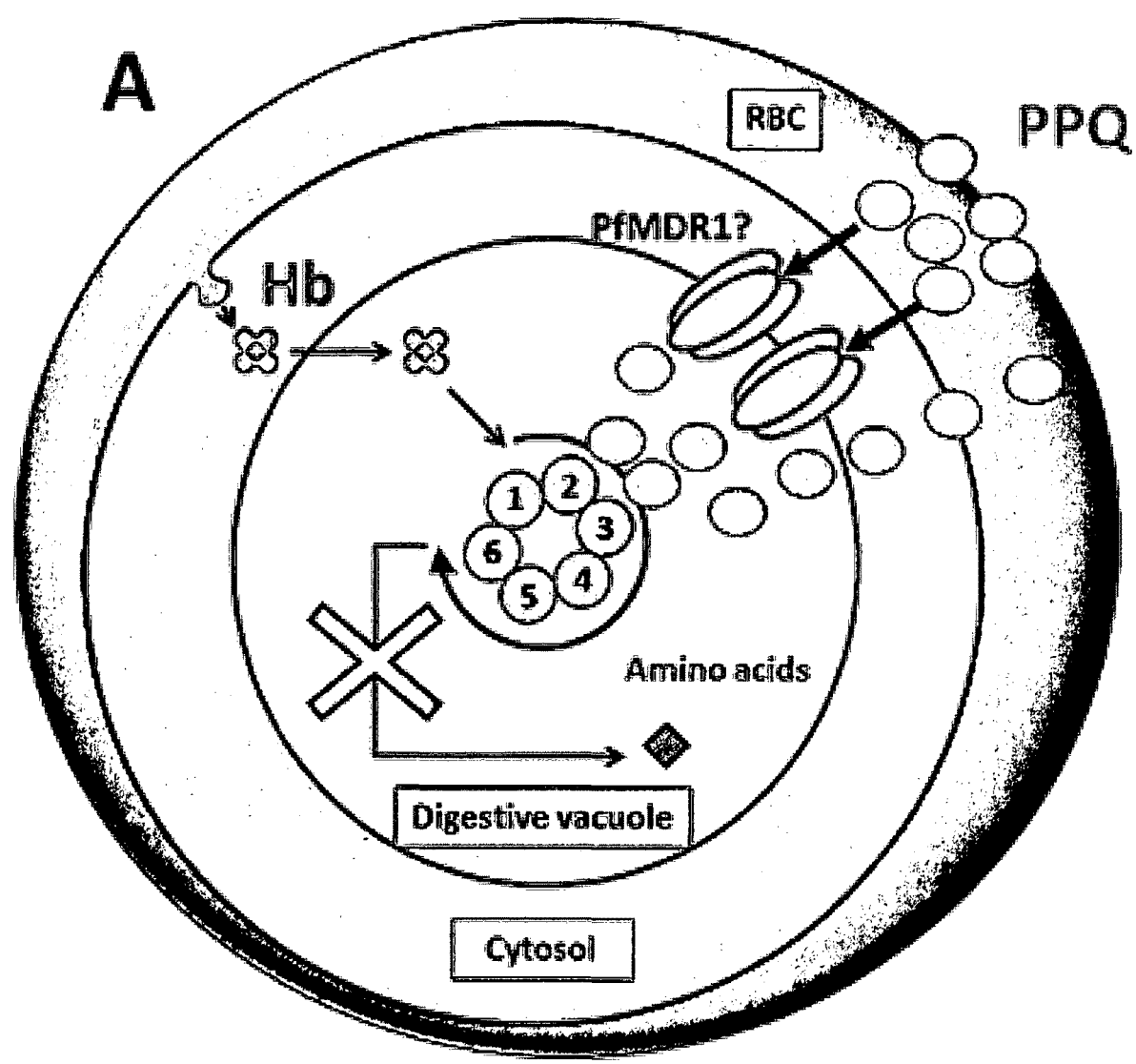
FIGS. 15A and 15 B show a hypothesis supporting the mechanisms of resistance of *P. falciparum* parasites to PPQ through the amplification of PfPM2 and PfPM3 genes, and the deamplification of the Pfmdr1 gene in Cambodia. (A) PPQ-sensitive parasite. PPQ accumulates in the food digestive vacuole via its weak-base properties. PfMDR1 transporter might help concentrate PPQ into the digestive vacuole, explaining the selection against multicopy Pfmdr1. PPQ inhibits hemoglobin degradation leading to the disruption of amino acid production. Parasite death is provoked. (B) PPQ-resistant parasite. Amplification of the PfPM2 and PfPM3 genes and increased production of the PfPM2 and PfPM3 proteases is proposed to compensate for the PPQ inhibition of hemoglobin catabolismrestoring normal globin-derived peptide levels used for amino acid production and promoting parasite survival. PfCRT might play a possible role in the efflux of PPQ from the digestive vacuole in some PPQ-resistant parasites. Hb: hemoglobin; 1: PfPM1; 2: PfPM2; 3: PfPM4; 4: PfFalcipain; 5: PfPM3; 6: PfFalcilysin.
Figure 15B:
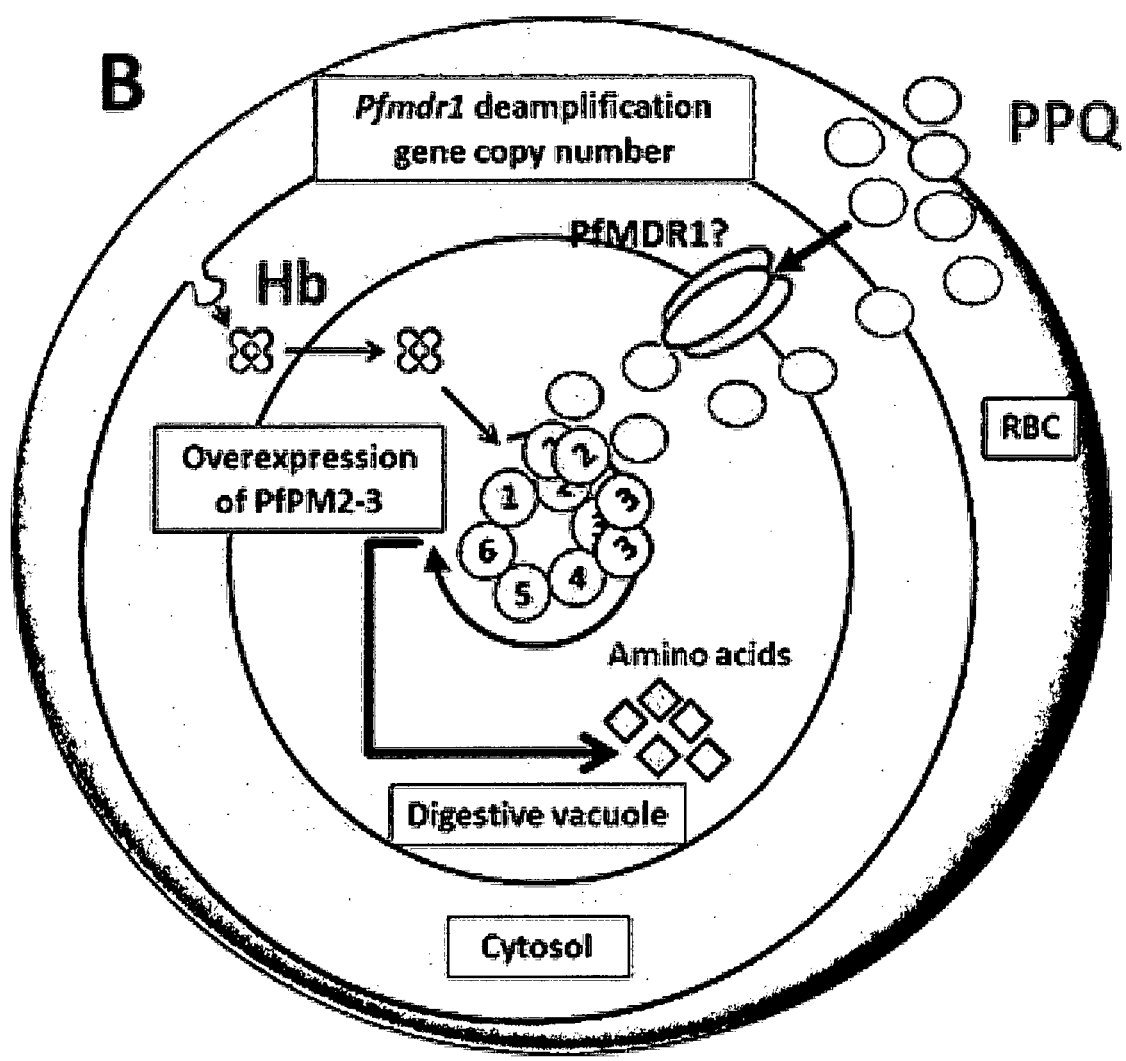

Plasmepsins are expressed during the intra-erythrocytic asexual blood stage cycle as well as by sexual stage gametocytes that can be transmitted to the mosquito vector. All four plasmepsins (PfPM1-4) are located in the digestive vacuole of intra-erythrocytic developmental forms where they engage in different steps of hemoglobin degradation. Studies of parasites disrupted in the PfPM genes pointed to redundancy in the hemoglobin degradation machinery.[24] To the inventors' knowledge, there are no reported studies about the consequences of overexpression of these proteases. The inventors show here that PfPM2 amplification is associated with a notable increase of steady state mRNA and protein levels in two culture-adapted isolates. This observation needs to be confirmed with additional isolates. A reasonable hypothesis is that the amplification of plasmepsins overcomes the inhibitory effect of PPQ on hemoglobin degradation and heme detoxification, possibly by reducing levels of reactive heme species that are preferred substrates for PPQ binding. PPQ-treated trophozoites have been shown to possess large digestive vacuoles containing membrane-bound packets of undigested hemoglobin.[25] The observation that PPQ-resistant parasites have a single Pfmdr1 copy is consistent with this scenario, as maintenance of a single Pfmdr1 copy (or reversion to a single copy) might avoid importing excessive amounts of PPQ into the digestive vacuole (FIG. 15).[26,27]

The inventors note that the association of PPQ resistance with amplification of the PfPM2-3 cluster on chromosome 14 is not proof of causality. The highly structured population of *P. falciparum* parasites in Cambodia 28 might confound the robustness of the association and additional loci might also contribute to PPQ resistance. The present findings should be complemented with laboratory investigations of the cellular consequences of this amplification on the parasite response to PPQ and on parasite fitness and transmissibility. Nonetheless, the current data are timely in providing a molecular tool that predicts the appearance of PPQ resistance in endemic settings.

PPQ is a well-tolerated partner drug currently used in combination with ART derivatives or the ozonide compound arterolane (OZ277).[29] The mechanism of PPQ resistance in the specific context of Cambodia, where ART resistance is nearly fixed and drug pressure is high, may not extrapolate to areas where ART resistance has not yet been documented. Nevertheless, the inventors propose to extend the assessment of PfPM2 gene copy number to areas where PPQ is being used in ACTs at a very large scale, and to combine this assay with K13 sequencing to localize areas of parasite resistance to both components. In Cambodia, where the rapid failure of first-line ACTs is jeopardizing elimination efforts and accelerating the emergence and spread of resistance, the opposing susceptibility between mefloquine and PPQ could be used to implement new strategies based on ACT drug rotation, sequential administration, or triple combinations including both ACT partner drugs. Although challenging to implement, these alternative strategies will help to ensure a long-term efficacy of antimalarials to reach the elimination goal.

It is pointed out that the inventors participated in three studies that have been recently published[30,31,32] wherein protocols identical or similar to those disclosed herein have been used in order to identify molecular signature associated with resistance of *Plasmodium falciparum* to treatments encompassing piperaquine and that said studies confirmed the results provided herein. The results of these studies confirm the present ones.

TABLE 1

Proportion of PCR-corrected *P. falciparum* recrudescences observed at day 42 in 2009-2015 in 12 provinces across Cambodia in patients treated with a 3-day course of DHA-PPQ regimen. Site location and years of collection are provided for isolates with in-vitro and ex-vivo PSA profiles (the map of the location of the study sites is presented Appendix_1).

| Year | Site (province) | No. patients treated and followed up | No. of patients classified as recrudescent (PCR-corrected) (%) | No. isolates with in-vitro PSA survival data | No. isolates with ex-vivo PSA survival data |
|---|---|---|---|---|---|
| 2009 | Pailin | 32 | 3 (9.4) | 0 | 0 |
| | Preah Vihear | 30 | 0 (0) | 0 | 0 |
| 2010 | Pailin | 21 | 4 (19.0) | 0 | 0 |
| | Pursat | 32 | 3 (9.4) | 0 | 0 |
| | Rattanakiri | 30 | 0 (0) | 0 | 0 |
| 2011 | Kratié | 51 | 2 (3.9) | 0 | 0 |
| | Preah Vihear | 34 | 2 (5.9) | 0 | 0 |
| | Pursat | 41 | 7 (17.1) | 0 | 0 |
| 2012 | Battambang | 39 | 12 (30.8) | 19 | 0 |
| | Kampong Speu | 22 | 0 (0) | 4 | 0 |
| | Kampong Thom | 38 | 0 (0) | 2 | 0 |
| | Pursat | 23 | 2 (8.7) | 6 | 0 |
| 2013 | Kampot | 17 | 1 (5.9) | 0 | 0 |
| | Kratié | 22 | 0 (0) | 0 | 0 |
| | Preah Vihear | 16 | 1 (6.3) | 0 | 0 |
| | Rattanakiri | 31 | 1 (3.2) | 0 | 0 |
| 2014 | Mondulkiri | 39 | 4 (10.3) | 0 | 0 |
| | Siemreap | 40 | 25 (62.5) | 0 | 0 |
| | Stungtreng | 33 | 11 (33.3) | 0 | 0 |
| | Rattanakiri | 34 | 5 (14.7) | 0 | 34 |
| 2015 | Mondulkiri | 16 | 4 (25.0) | 0 | 16 |
| | Rattanakiri | 54 | 16 (29.6) | 0 | 54 |
| | Siemreap | 17 | 10 (58.8) | 0 | 17 |
| | Stungtreng | 13 | 6 (46.1) | 0 | 13 |
| Total | | 725 | 119 (16.4) | 31 | 134 |

TABLE 2

Details of the 31 K13-C580Y mutant (and the 3D7 reference line), PPQ-resistant and -sensitive culture-adapted parasites analyzes by whole-genome sequencing. The last column lists the DNA expansion types observed in the region of chromosome 14 encoding the plasmepsin 1-4 hemoglobinases.

| Parasite lines ID | Year | Site location | in-vitro PSA survival rate (%) | in-vitro susceptibility to PPQ* | DNA expansion type |
|---|---|---|---|---|---|
| 3D7 | — | — | 0.1 | Sensitive | No amplification |
| 6273 | 2012 | Kampong Speu | 0.2 | Sensitive | No amplification |
| 6337 | 2012 | Kampong Speu | 0.4 | Sensitive | No amplification |
| 6403 | 2012 | Pursat | 0.5 | Sensitive | No amplification |
| 6267 | 2012 | Kampong Speu | 0.5 | Sensitive | No amplification |
| 6349 | 2012 | Kampong Thom | 0.6 | Sensitive | No amplification |
| 6237 | 2012 | Kampong Thom | 0.8 | Sensitive | No amplification |
| 6410 | 2012 | Battambang | 6.0 | Sensitive | No amplification |
| 6369 | 2012 | Pursat | 6.4 | Sensitive | Type 1 |
| 6395 | 2012 | Battambang | 19.2 | Resistant | No amplification |
| 6341 | 2012 | Pursat | 25.8 | Resistant | Type 1 |
| 6280 | 2012 | Battambang | 28.9 | Resistant | Type 4 |
| 6246 | 2012 | Kampong Speu | 36.9 | Resistant | No amplification |
| 6293 | 2012 | Battambang | 39.3 | Resistant | Type 3 |
| 6391 | 2012 | Battambang | 39.4 | Resistant | Type 1 |
| 6272 | 2012 | Battambang | 40.0 | Resistant | Type 1 |
| 6218 | 2012 | Battambang | 40.8 | Resistant | Type 1 |
| 6302 | 2012 | Battambang | 42.5 | Resistant | Type 1 |
| 6229 | 2012 | Battambang | 46.6 | Resistant | Type 1 |
| 6443 | 2012 | Battambang | 49.6 | Resistant | Type 1 |
| 6430 | 2012 | Battambang | 51.3 | Resistant | Type 1 |
| 6429 | 2012 | Pursat | 51.8 | Resistant | Type 1 |
| 6365 | 2012 | Battambang | 51.8 | Resistant | Type 4 |
| 6394 | 2012 | Battambang | 56.7 | Resistant | Type 1 |
| 6219 | 2012 | Battambang | 58.6 | Resistant | Type 2 |
| 6408 | 2012 | Battambang | 58.7 | Resistant | Type 2 |
| 6224 | 2012 | Pursat | 61.4 | Resistant | Type 1 |
| 6431 | 2012 | Battambang | 61.5 | Resistant | Type 2 |
| 6320 | 2012 | Battambang | 62.1 | Resistant | Type 2 |
| 6261 | 2012 | Pursat | 70.5 | Resistant | Type 1 |
| 6411 | 2012 | Battambang | 71.6 | Resistant | Type 2 |
| 6427 | 2012 | Battambang | 77.4 | Resistant | Type 2 |

*Threshold used to define in-vitro susceptibility to PPQ: sensitive if survival rates were <10% and resistant if survival rates were ≥10%.

REFERENCES

1. Ariey F, Witkowski B, Amaratunga C, et al. A molecular marker of artemisinin-resistant *Plasmodium falciparum* malaria. *Nature* 2014; 505:50-5.
2. Ashley E A, Dhorda M, Fairhurst R M, et al. Spread of artemisinin resistance in *Plasmodium falciparum* malaria. *The New England journal of medicine* 2014; 371:411-23.
3. Takala-Harrison S, Jacob C G, Arze C, et al. Independent emergence of artemisinin resistance mutations among *Plasmodium falciparum* in Southeast Asia. *The Journal of infectious diseases* 2015; 211:670-9.
4. Dondorp A M, Nosten F, Yi P, et al. Artemisinin resistance in *Plasmodium falciparum* malaria. *The New England journal of medicine* 2009; 361:455-67.
5. Noedl H, Se Y, Schaecher K, et al. Evidence of artemisinin-resistant malaria in western Cambodia. *The New England journal of medicine* 2008; 359:2619-20.
6. Amaratunga C, Lim P, Suon S, et al. Dihydroartemisinin-piperaquine resistance in *Plasmodium falciparum* malaria in Cambodia: a multisite prospective cohort study. *The Lancet Infectious diseases* 2016; 16:357-65.
7. Duru V, Khim N, Leang R, et al. *Plasmodium falciparum* dihydroartemisinin-piperaquine failures in Cambodia are associated with mutant K13 parasites presenting high survival rates in novel piperaquine in vitro assays: retrospective and prospective investigations. *BMC medicine* 2015; 13:305.
8. Leang R, Taylor W R, Bouth D M, et al. Evidence of *Plasmodium falciparum* Malaria Multidrug Resistance to Artemisinin and Piperaquine in Western Cambodia: Dihydroartemisinin-Piperaquine Open-Label Multicenter Clinical Assessment. *Antimicrobial agents and chemotherapy* 2015; 59:4719-26.
9. Spring M D, Lin J T, Manning J E, et al. Dihydroartemisinin-piperaquine failure associated with a triple mutant including kelch13 C580Y in Cambodia: an observational cohort study. *The Lancet Infectious diseases* 2015; 15:683-91.
10. Leang R, Barrette A, Bouth D M, et al. Efficacy of dihydroartemisinin-piperaquine for treatment of uncomplicated *Plasmodium falciparum* and *Plasmodium vivax* in Cambodia, 2008 to 2010. *Antimicrobial agents and chemotherapy* 2013; 57:818-26.
11. World Health Organization. Methods for surveillance of antimalarial drug efficacy. Geneva: WHO Press; 2009.
12. Cranmer S L, Magowan C, Liang J, Coppel R L, Cooke B M. An alternative to serum for cultivation of *Plasmodium falciparum* in vitro. *Transactions of the Royal Society of Tropical Medicine and Hygiene* 1997; 91:363-5.
13. World Health Organization. Methods and techniques for clinical trials on antimalarial drug efficacy: genotyping to identify parasite populations. Geneva: WHO Press; 2007.
14. Beghain J, Langlois A C, Legrand E, et al. *Plasmodium* copy number variation scan: gene copy numbers evaluation in haploid genomes. *Malaria journal* 2016; 15:206.

15. Wang S, Dvorkin D, Da Y. SNPEVG: a graphical tool for GWAS graphing with mouse clicks. *BMC bioinformatics* 2012; 13:319.
16. Eastman R T, Dharia N V, Winzeler E A, Fidock D A. Piperaquine resistance is associated with a copy number variation on chromosome 5 in drug-pressured *Plasmodium falciparum* parasites. *Antimicrobial agents and chemotherapy* 2011; 55:3908-16.
17. Veiga M I, Dhingra S K, Henrich P P, et al. Globally prevalent PfMDR1 mutations modulate *Plasmodium falciparum* susceptibility to artemisinin-based combination therapies. *Nature communications* 2016; 7:11553.
18. Cowman A F, Galatis D, Thompson J K. Selection for mefloquine resistance in *Plasmodium falciparum* is linked to amplification of the pfmdr1 gene and cross-resistance to halofantrine and quinine. *Proceedings of the National Academy of Sciences of the United States of America* 1994; 91:1143-7.
19. Price R N, Uhlemann A C, Brockman A, et al. Mefloquine resistance in *Plasmodium falciparum* and increased pfmdr1 gene copy number. *Lancet* 2004; 364:438-47.
20. Sidhu A B, Uhlemann A C, Valderramos S G, Valderramos J C, Krishna S, Fidock D A. Decreasing pfmdr1 copy number in *Plasmodium falciparum* malaria heightens susceptibility to mefloquine, lumefantrine, halofantrine, quinine, and artemisinin. *The Journal of infectious diseases* 2006; 194:528-35.
21. Heinberg A, Siu E, Stern C, et al. Direct evidence for the adaptive role of copy number variation on antifolate susceptibility in *Plasmodium falciparum*. *Molecular microbiology* 2013; 88:702-12.
22. Nair S, Nash D, Sudimack D, et al. Recurrent gene amplification and soft selective sweeps during evolution of multidrug resistance in malaria parasites. *Molecular biology and evolution* 2007; 24:562-73.
23. Lim P, Dek D, Try V, Sreng S, Suon S, Fairhurst R M. Decreasing pfmdr1 copy number suggests that *Plasmodium falciparum* in Western Cambodia is regaining in vitro susceptibility to mefloquine. *Antimicrobial agents and chemotherapy* 2015; 59:2934-7.
24. Bonilla J A, Moura P A, Bonilla T D, Yowell C A, Fidock D A, Dame J B. Effects on growth, hemoglobin metabolism and paralogous gene expression resulting from disruption of genes encoding the digestive vacuole plasmepsins of *Plasmodium falciparum*. *International journal for parasitology* 2007; 37:317-27.
25. Sachanonta N, Chotivanich K, Chaisri U, et al. Ultrastructural and real-time microscopic changes in *P. falciparum*-infected red blood cells following treatment with antimalarial drugs. *Ultrastructural pathology* 2011; 35:214-25.
26. Rohrbach P, Sanchez C P, Hayton K, et al. Genetic linkage of pfmdr1 with food vacuolar solute import in *Plasmodium falciparum*. *The EMBO journal* 2006; 25:3000-11.
27. Sanchez C P, Rotmann A, Stein W D, Lanzer M. Polymorphisms within PfMDR1 alter the substrate specificity for anti-malarial drugs in *Plasmodium falciparum*. *Molecular microbiology* 2008; 70:786-98.
28. Miotto O, Almagro-Garcia J, Manske M, et al. Multiple populations of artemisinin-resistant *Plasmodium falciparum* in Cambodia. *Nature genetics* 2013; 45:648-55.
29. Valecha N, Krudsood S, Tangpukdee N, et al. Arterolane maleate plus piperaquine phosphate for treatment of uncomplicated *Plasmodium falciparum* malaria: a comparative, multicenter, randomized clinical trial. *Clinical infectious diseases* 2012; 55:663-71.
30. Phuc B Q et al Treatment failure of dihydroartemisinin/piperaquine for *Plasmodium falciparum* Malaria, Vietnam *Emerging Infectious Diseases* vol 23, No. 4, April 2017
31. Imwong M et al The spread of artemisinin-resistant *Plasmodium falciparum* in the Greater Mekong subregion: a molecular epidemiology observational study *The Lancet* Vol 17 May 2017:491-497
32. Mukherjee A et al Artemisinin resistance without pfkelch13 mutations in *Plasmodium falciparum* isolates in Cambodia Malar J. (2017) 16:195

We claim:

1. A method for in vitro genotyping and treatment of a *Plasmodium* resistant to piperaquine comprising:
   extracting DNA from a sample containing a *Plasmodium* from a patient infected by a *Plasmodium*,
   measuring the number of copies per genome of PfPM2 and PfPM3 genes, and
   detecting the presence of at least 2 copies per genome of PfPM2 and PfPM3 genes of the *Plasmodium* resistant to piperaquine in the extracted DNA, and
   treating the patient with an anti-malaria treatment without piperaquine if the patient is infected by a *Plasmodium* that has at least 2 copies per genome of PfPM2 and PfPM3 genes.

2. The method of claim 1, wherein the presence of at least 2 copies per genome of PfPM2 and PfPM3 genes of the *Plasmodium* resistant to piperaquine is detected by sequencing.

3. The method of claim 1, wherein the presence of at least 2 copies per genome of PfPM2 and PfPM3 genes of the *Plasmodium* resistant to piperaquine is detected by PCR.

4. The method of claim 3, wherein the presence of at least 2 copies per genome of PfPM2 and PfPM3 genes of the *Plasmodium* resistant to piperaquine is detected by quantitative PCR (qPCR).

5. The method of claim 1, wherein the presence of at least 2 copies per genome of PfPM2 and PfPM3 genes of the *Plasmodium* resistant to piperaquine is detected by nucleic acid hybridization.

6. The method of claim 1, further comprising detecting the presence or absence of a mutated K-13 propeller nucleic acid or protein in the sample to determine if the *Plasmodium* is also resistant to treatment with artemisinin or its derivatives.

7. A method for the in vitro detection and treatment of a *Plasmodium* infection resistant to piperaquine in a patient comprising:
   extracting DNA from a blood sample obtained from a patient,
   measuring the number of copies per genome of PfPM2 and PfPM3 genes, and
   detecting the presence of at least 2 copies per genome of PfPM2 and PfPM3 genes of the *Plasmodium* resistant to piperaquine in the extracted DNA from the blood sample, and
   treating the patient with an anti-malaria treatment without piperaquine if the patient is infected by a *Plasmodium* that has at least 2 copies per genome of PfPM2 and PfPM3 genes.

8. The method of claim 7, wherein the presence of at least 2 copies per genome of PfPM2 and PfPM3 genes of the *Plasmodium* is detected by sequencing.

9. The method of claim 7, wherein the presence of at least 2 copies per genome of PfPM2 and PfPM3 genes of the *Plasmodium* is detected by PCR.

10. The method of claim 9, wherein the presence of at least 2 copies per genome of PfPM2 and PfPM3 genes of the *Plasmodium* is detected by quantitative PCR (qPCR).

11. The method of claim 7, wherein the presence of at least 2 copies per genome of PfPM2 and PfPM3 genes of the *Plasmodium* is detected by nucleic acid hybridization.

12. The method of claim 7, further comprising detecting the presence or absence of a mutated K-13 propeller nucleic acid or protein in the sample to determine if the *Plasmodium* is also resistant to treatment with artemisinin or its derivatives.

13. The method of claim 12, which further comprises administering to a patient infected with the *Plasmodium* resistant to piperaquine a treatment with artemisinin or its derivatives if the *Plasmodium* resistant to piperaquine does not contain a K-13 propeller mutation.

14. The method of claim 1, wherein the presence of at least 2 copies per genome of PfPM2 and PfPM3 genes of the *Plasmodium* resistant to piperaquine is detected by PCR or by qPCR with the following primers:

```
                                                   (SEQ ID NO: 1)
5'-TGGTGATGCAGAAGTTGGAG-3'; and (SEQ ID NO: 2)
5'-TGGGACCCATAAATTAGCAGA-3'.
```

15. The method of claim 7, wherein the presence of at least 2 copies per genome of PfPM2 and PfPM3 genes of the *Plasmodium* resistant to piperaquine is detected by PCR or by qPCR with the following primers:

```
                                                   (SEQ ID NO: 1)
5'-TGGTGATGCAGAAGTTGGAG-3'; and (SEQ ID NO: 2)
5'-TGGGACCCATAAATTAGCAGA-3'.
```

16. The method of claim 1, wherein the presence of at least 2 copies per genome of PfPM2 and PfPM3 genes of the *Plasmodium* resistant to piperaquine is detected by nucleic acid hybridization with a probe comprising the sequence 5'-CAACATTTGATGGTATCCTTGGTTTAGGATGGA-3' (SEQ ID NO:5).

17. The method of claim 7, wherein the presence of at least 2 copies per genome of PfPM2 and PfPM3 genes of the *Plasmodium* is detected by nucleic acid hybridization with a probe comprising the sequence 5'-CAACATTGATGGTATCCTTGGTTTAGGATGGA-3' (SEQ ID NO:5).

\* \* \* \* \*